US010875829B1

(12) United States Patent
Sonesson et al.

(10) Patent No.: US 10,875,829 B1
(45) Date of Patent: Dec. 29, 2020

(54) AZETIDINE DERIVATIVES USEFUL AS MODULATORS OF CORTICAL CATECHOLAMINERGIC NEUROTRANSMISSION

(71) Applicant: Integrative Research Laboratories Sweden AB, Gothenburg (SE)

(72) Inventors: Clas Sonesson, Billdal (SE); Fredrik Pettersson, Gothenburg (SE)

(73) Assignee: INTEGRATIVE RESEARCH LABORATORIES SWEDEN AB, Göteborg (SE)

( * ) Notice: Subject to any disclaimer, the term of this patent is extended or adjusted under 35 U.S.C. 154(b) by 0 days.

(21) Appl. No.: 16/461,086

(22) PCT Filed: Nov. 17, 2017

(86) PCT No.: PCT/EP2017/079666
§ 371 (c)(1),
(2) Date: May 15, 2019

(87) PCT Pub. No.: WO2018/091687
PCT Pub. Date: May 24, 2018

(30) Foreign Application Priority Data

Nov. 18, 2016 (EP) ..................................... 16199545

(51) Int. Cl.
*C07D 205/04* (2006.01)
*A61P 25/28* (2006.01)
(52) U.S. Cl.
CPC ............ *C07D 205/04* (2013.01); *A61P 25/28* (2018.01)
(58) Field of Classification Search
CPC .................................................. C07D 205/04
See application file for complete search history.

(56) References Cited

U.S. PATENT DOCUMENTS

| | | | | |
|---|---|---|---|---|
| 2010/0190771 | A1* | 7/2010 | Claffey | A61P 25/18 514/210.21 |
| 2012/0329777 | A1* | 12/2012 | Claffey | A61K 31/27 514/210.21 |
| 2013/0131035 | A1* | 5/2013 | Bregman | C07D 251/48 514/210.2 |
| 2015/0045348 | A1* | 2/2015 | Svenstrup | A61P 25/00 514/210.21 |
| 2017/0334846 | A1* | 11/2017 | Basinger | A61P 25/00 |
| 2018/0148445 | A1* | 5/2018 | Andrews | A61P 35/00 |

FOREIGN PATENT DOCUMENTS

| EP | 2754653 A2 | 7/2014 |
|---|---|---|
| WO | WO-2004/113297 A2 | 12/2004 |
| WO | WO-2007/148185 A2 | 12/2007 |
| WO | WO 2010/022055 * | 2/2010 |
| WO | WO-2010/022055 A2 | 2/2010 |
| WO | WO-2010/058017 A1 | 5/2010 |
| WO | WO-2010/058018 A1 | 5/2010 |
| WO | WO-2010/084428 A1 | 7/2010 |
| WO | WO-2011/103196 A1 | 8/2011 |
| WO | WO-2012/168817 A1 | 12/2012 |
| WO | WO-2016/030310 A1 | 3/2016 |
| WO | WO-2016/073420 A1 | 5/2016 |
| WO | WO-2016/185032 A1 | 11/2016 |
| WO | WO-2017/045648 A1 | 3/2017 |

OTHER PUBLICATIONS

Abi-Dargham et al., Mechanisms of Action of Second Generation Antipsychotic Drugs in Schizophrenia: Insights from Brain Imaging Studies. Eur Psychiatry. 2005; 20(1):15-27.
Arnsten, Catecholamine Influences on Dorsolateral Prefrontal Cortical Networks. Biol Psych. 2011; 69(12):89-99.
Berge, S.M. et al., Pharmaceutical salts. J Pharm Sci. 1977; 66(1):1-19.
Bramham et al., The Arc of Synaptic Memory. Exp Brain Res. 2010; 200:125-40.
Chomzynski, P. and Sacchi, N., Single-Step Method of RNA Isolation by Acid Guanidinium Thiocyanate-Phenol-Chloroform Extraction. Anal Biochem. 1987; 162(1):156-9.
Claffey, M.M. et al., Application of Structure-Based Drug Design and Parallel Chemistry to Identify Selective, Brain Penetrant, in vivo Active Phosphodiesterase 9A Inhibitors. J Med Chem. 2012; 55(21):9055-68.
Crespi et al., Fluorometric Screening for Metabolism-Based Drug—Drug Interactions. J Pharm Tox Meth. 2000; 44:325-31.
Devoto, P. et al., Evidence for Co-Release of Noradrenaline and Dopamine from Noradrenergic Neurons in the Cerebral Cortex. Mol Psychiatry. 2001; 6(6):657-64.
Hamon et al., Monoamine Neurocircuitry in Depression and Strategies for New Treatment. Progress Neuro Psychopharmocol Biol Psych. 2013; 45:54-63.
Harrison et al., Schizophrenia Genes, Gene Expression, and Neuropathology: on the Matter of Their Convergence. Mol Psych. 2005; 10:40-68.
Kawashima et al., Synaptic Activity-Responsive Element in the Arc/Arg3.1 Promoter Essential for Synapse-to-Nucleus Signaling in Activated Neurons. Proc Natl Acad Sci USA. 2009; 106(1):316-21.

(Continued)

*Primary Examiner* — Valerie Rodriguez-Garcia
(74) *Attorney, Agent, or Firm* — Ballard Spahr LLP

(57) ABSTRACT

The disclosure provides a pharmaceutical composition comprising a therapeutically effective amount of a compound of Formula (I): (I) or an isotope labelled analog thereof, or a pharmaceutically acceptable salt thereof, wherein: each of $R_1$, $R_2$, $R_3$, $R_6$ and $R_7$ represents H or F, $R_4$ represents H or $CH_3$ $R_5$ represents H or $C_1$-$C_4$alkyl, wherein at least two of $R_1$, $R_2$, $R_3$, $R_6$ and $R_7$ represent F, together with at least one pharmaceutically acceptable carrier, excipient and/or diluent.

20 Claims, No Drawings

Specification includes a Sequence Listing.

(56) References Cited

OTHER PUBLICATIONS

Landgren et al., A Novel ARC Gene Polymorphism is Associated with Rediced Risk of Alzheimer's Disease. J Neural Transm (Vienna). 2012; 119(7):833-42.
Langin, D. et al., [$^3$H]RX821002: a New Tool for the Identification of $\alpha_{2A}$-Adrenoceptors. Eur J Pharmacol. 1989; 167:95-104.
Link et al., Somatodentric Expression of an Immediate Early Gene is Regulated by Synaptic Activity. Proc Natl Acad Sci USA. 1995; 92:5734-8.
Lyford et al., Arc, a Growth Factor and Activity-Regulated Gene, Encodes a Novel Cytoskeleton-Associated Protein that is Enriched in Neuronal Dendrites. Neuron. 1995; 14:433-5.
Moghaddam and Bunney, Ionic Composition of Microdialysis Perfusing Solution Alter the Pharmacological Responsiveness and Basal Outflow of Striatal Dopamine. J Neurochem. 1989; 53:652-4.
Pacholczyk, T. et al., Expression Cloning of a Cocaine- and Antidepressant-Sensitive Human Noradrenaline Transporter. Nature. 1991; 350(6316):350-4.
Paulekuhn, G.S. et al., Trends in Active Pharmaceutical Ingredient Salt Selection Based on Analysis of the Orange Book Database. J Med Chem. 2007; 50(26):6665-72.
Paxinos, G. and Watson, C., The Rat Brain in Stereotaxic Coordinates. NY Acad Press. 1986; Figure 8 and Figure 14 (2 pages).
Perrin, C.L. et al., Secondary Deuterium Isotope Effects on the Acidity of Carboxylic Acids and Phenols. J Am Chem Soc. 2007; 129(14):4490-7.
Pristupa, Z.B. et al., Pharmacological Heterogeneity of Cloned and Native Human Dopamine Transporter: Disassociation of [$^3$H]WIN 35,428 and [$^3$H]GBR 12,935 Binding. Mol Pharmacol. 1994; 45(1):125-35.
Rautio et al., Prodrugs: Design and Clinical Applications. Nat Rev Drug Discov. 2008; 7(3):255-70.
Renwick et al., Metabolism of 2,5-Bis(Trifluoromethyl)-7-Bensyloxy-4-Trifluoromethyloco by Human Hepatic CYP Isoforms: Evidence for Selectivity Towards CYP3A4. Xenobiotica. 2001; 31(4):187-204.
Santiago and Westerink. Characterization of the in Vivo Release of Dopamine as Recorded by Different Types of Intracerebral Microdialysis Probes. Naunyn-Schmiedeberg's Arch Pharmacol. 1990; 342:407-14.
Sesack, S.R. et al., Anatomical Substrates of Glutamate-Dopamine Interactions: Evidence for Specificity of Connections and Extrasynaptic Actions. Annal NY Acad Sci. 2003; 1003:36-52.
Steward and Worley, Selective Targeting of Newly Synthesiezed Arc mRNA to Active Synapses Requires NMDA Receptor Activation. Neuron. 2001; 30:227-40.
Tatsumi, M. et al., Pharmacological Profile of Neuroleptics at Human Monoamine Transporters. Eur J Pharmacol. 1999; 368(2-3):277-83.
Trillo et al., Ascending Monoaminergic Systems Alterations in Alzheimer's Disease. Translating Basic Science into Clinical Care. Neurosci Biobehav Rev. 2013; 37:1363-79.
Ungerstedt, U., Microdialysis—Principles and Applications for Studies in Animals and Man. J Intern Med. 1991; 230(4):365-73.
Wang, H. et al., Targeted Pharmacological Treatment of Autism Spectrum Disorders: Fragile X and Rett Syndroms. Front Cell Neurosci. 2015; 9:1-23.
Waters, N. et al., Differential Effects of Dopamine D2 and D3 Receptor Antagonists in Regard to Dopamine Release, in Vivo Receptor Displacement and Behavior. J Neural Transm. 1994; 98(1):39-55.
CAS Registry No. 121876-03-7.
CAS Registry No. 954220-76-9.
CAS Registry No. 1236862-32-0.
CAS Registry No. 1263378-82-0.
CAS Registry No. 1864062-13-4.
CAS Registry No. 1263378-42-2.
CAS Registry No. 954225-05-9.
CAS Registry No. 124675-84-2.
CAS Registry No. 1211876-06-0.
CAS Registry No. 1965310-43-3.
CAS Registry No. 1332301-38-8.
CAS Registry No. 2044975-10-0.
CAS Registry No. 2044975-15-5.
CAS Registry No. 1343963-39-2.
International Search Report and Written Opinion dated Jan. 29, 2018 by the International Searching Authority for Patent Application No. PCT/EP2017/079666, which was filed on Nov. 17, 2017 and published as WO 2018/091687 dated May 24, 2018 (Inventor—Clas Sonesson; Applicant—Integrative Research Laboratories Sweden AB) (11 pages).

\* cited by examiner

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Activity-regulated gene (Arc) (accession number
      U19866) sense primer

<400> SEQUENCE: 1
ggagttcaag aaggagtttc                                                   20

<210> SEQ ID NO 2
<211> LENGTH: 19
<212> TYPE: DNA
<213> ORGANISM: Artificial Sequence
<220> FEATURE:
<223> OTHER INFORMATION: Activity-regulated gene (Arc) (accession number
      U19866) antisense primer

<400> SEQUENCE: 2
ccacatacag tgtctggta                                                    19

<210> SEQ ID NO 3
<211> LENGTH: 20
<212> TYPE: DNA
<213> ORGANISM: Artificial Sequence
<220> FEATURE:
<223> OTHER INFORMATION: Activity-regulated gene (Arc) (accession number
      U19866) probe

<400> SEQUENCE: 3
ccgcttacgc cagaggaact                                                   20

<210> SEQ ID NO 4
<211> LENGTH: 20
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) sense primer 01

<400> SEQUENCE: 4
agggatttga atcatgtttg                                                   20

<210> SEQ ID NO 5
<211> LENGTH: 19
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) antisense primer 01

<400> SEQUENCE: 5
ctgctagttc tttactggc                                                    19

<210> SEQ ID NO 6
<211> LENGTH: 23
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) probe 01

<400> SEQUENCE: 6
tgtagattca acttgccgct gtc                                               23

-continued

```
<210> SEQ ID NO 7
<211> LENGTH: 18
<212> TYPE: DNA
<213> ORGANISM: Artificial Sequence
<220> FEATURE:
<223> OTHER INFORMATION: Cyclophilin A (cyclo) (accession number M19533)
      sense primer 01

<400> SEQUENCE: 7
ctggaccaaa cacaaatg                                                  18

<210> SEQ ID NO 8
<211> LENGTH: 18
<212> TYPE: DNA
<213> ORGANISM: Artificial Sequence
<220> FEATURE:
<223> OTHER INFORMATION: Cyclophilin A (cyclo) (accession number M19533)
      antisense primer 01

<400> SEQUENCE: 8
atgccttctt tcaccttc                                                  18

<210> SEQ ID NO 9
<211> LENGTH: 20
<212> TYPE: DNA
<213> ORGANISM: Artificial Sequence
<220> FEATURE:
<223> OTHER INFORMATION: Cyclophilin A (cyclo) (accession number M19533)
      probe 01

<400> SEQUENCE: 9
ttgccatcca gccactcagt                                                20

<210> SEQ ID NO 10
<211> LENGTH: 22
<212> TYPE: DNA
<213> ORGANISM: Artificial Sequence
<220> FEATURE:
<223> OTHER INFORMATION: Brain Derived Neurotrophic Factor (bdnf)
      (accession number NM_012513) sense primer

<400> SEQUENCE: 10
aaattacctg gatgccgcaa ac                                             22

<210> SEQ ID NO 11
<211> LENGTH: 22
<212> TYPE: DNA
<213> ORGANISM: Artificial Sequence
<220> FEATURE:
<223> OTHER INFORMATION: Brain Derived Neurotrophic Factor (bdnf)
      (accession number NM_012513) antisense primer

<400> SEQUENCE: 11
tgtgacccac tcgctaatac tg                                             22

<210> SEQ ID NO 12
<211> LENGTH: 23
<212> TYPE: DNA
<213> ORGANISM: Artificial Sequence
<220> FEATURE:
<223> OTHER INFORMATION: Brain Derived Neurotrophic Factor (bdnf)
      (accession number NM_012513) probe

<400> SEQUENCE: 12
cacacacgct cagctcccca cgg                                            23
```

<210> SEQ ID NO 13
<211> LENGTH: 18
<212> TYPE: DNA
<213> ORGANISM: Artificial Sequence
<220> FEATURE:
<223> OTHER INFORMATION: Rattus norvegicus proto-oncogen (c-fos)
      (accession number DQ089699) sense primer

<400> SEQUENCE: 13
cagagcatcg gcagaagg                                                 18

<210> SEQ ID NO 14
<211> LENGTH: 21
<212> TYPE: DNA
<213> ORGANISM: Artificial Sequence
<220> FEATURE:
<223> OTHER INFORMATION: Rattus norvegicus proto-oncogen (c-fos)
      (accession number DQ089699) antisense primer

<400> SEQUENCE: 14
agttgatctg tctccgcttg g                                             21

<210> SEQ ID NO 15
<211> LENGTH: 26
<212> TYPE: DNA
<213> ORGANISM: Artificial Sequence
<220> FEATURE:
<223> OTHER INFORMATION: Rattus norvegicus proto-oncogen (c-fos)
      (accession number DQ089699) probe

<400> SEQUENCE: 15
tctgtcagct ccctcctccg attccg                                        26

<210> SEQ ID NO 16
<211> LENGTH: 22
<212> TYPE: DNA
<213> ORGANISM: Artificial Sequence
<220> FEATURE:
<223> OTHER INFORMATION: Glutamic acid decarboxylase (GAD 67) (accession
      number 34445) sense primer

<400> SEQUENCE: 16
ctgtttatgg agcgtttgat cc                                            22

<210> SEQ ID NO 17
<211> LENGTH: 22
<212> TYPE: DNA
<213> ORGANISM: Artificial Sequence
<220> FEATURE:
<223> OTHER INFORMATION: Glutamic acid decarboxylase (GAD 67) (accession
      number 34445) antisense primer

<400> SEQUENCE: 17
gactgagact gacctttcta tg                                            22

<210> SEQ ID NO 18
<211> LENGTH: 22
<212> TYPE: DNA
<213> ORGANISM: Artificial Sequence
<220> FEATURE:
<223> OTHER INFORMATION: Glutamic acid decarboxylase (GAD 67) (accession
      number 34445) probe

<400> SEQUENCE: 18
gactgaattg gcccttttcta tg                                           22

-continued

```
<210> SEQ ID NO 19
<211> LENGTH: 19
<212> TYPE: DNA
<213> ORGANISM: Artificial Sequence
<220> FEATURE:
<223> OTHER INFORMATION: Glutamate dehydrogenase (glud) (accession
      number NM_012570) sense primer

<400> SEQUENCE: 19
agcctctcct tccccatcc                                              19

<210> SEQ ID NO 20
<211> LENGTH: 20
<212> TYPE: DNA
<213> ORGANISM: Artificial Sequence
<220> FEATURE:
<223> OTHER INFORMATION: Glutamate dehydrogenase (glud) (accession
      number NM_012570) antisense primer

<400> SEQUENCE: 20
cgccttcacc tcatccacac                                             20

<210> SEQ ID NO 21
<211> LENGTH: 21
<212> TYPE: DNA
<213> ORGANISM: Artificial Sequence
<220> FEATURE:
<223> OTHER INFORMATION: Glutamate dehydrogenase (glud) (accession
      number NM_012570) probe

<400> SEQUENCE: 21
agcacagcca gcaccgcacg c                                           21

<210> SEQ ID NO 22
<211> LENGTH: 19
<212> TYPE: DNA
<213> ORGANISM: Artificial Sequence
<220> FEATURE:
<223> OTHER INFORMATION: Preproenkephalin (penk) (accession number
      NM_017139.1) sense primer

<400> SEQUENCE: 22
catgtgctgc ttgtgctgt                                              19

<210> SEQ ID NO 23
<211> LENGTH: 19
<212> TYPE: DNA
<213> ORGANISM: Artificial Sequence
<220> FEATURE:
<223> OTHER INFORMATION: Preproenkephalin (penk) (accession number
      NM_017139.1) antisense primer

<400> SEQUENCE: 23
cagttgggtt cacgggttt                                              19

<210> SEQ ID NO 24
<211> LENGTH: 24
<212> TYPE: DNA
<213> ORGANISM: Artificial Sequence
<220> FEATURE:
<223> OTHER INFORMATION: Preproenkephalin (penk) (accession number
      NM_017139.1) probe

<400> SEQUENCE: 24
tgccctcgtg gtctggataa ctgc                                        24

<210> SEQ ID NO 25
```

```
<211> LENGTH: 21
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) sense primer 02

<400> SEQUENCE: 25
ggccagactt tgttggattt g                                              21

<210> SEQ ID NO 26
<211> LENGTH: 20
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) antisense primer 02

<400> SEQUENCE: 26
ccgctgtctt ttaggctttg                                                20

<210> SEQ ID NO 27
<211> LENGTH: 28
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) probe 02

<400> SEQUENCE: 27
tttccacttt cgctgatgac acaaacat                                       28

<210> SEQ ID NO 28
<211> LENGTH: 20
<212> TYPE: DNA
<213> ORGANISM: Artificial Sequence
<220> FEATURE:
<223> OTHER INFORMATION: Cyclophilin A (cyclo) (accession number M19533)
      sense primer 02

<400> SEQUENCE: 28 gtctctttc gccgcttgct                                                 20

<210> SEQ ID NO 29
<211> LENGTH: 25
<212> TYPE: DNA
<213> ORGANISM: Artificial Sequence
<220> FEATURE:
<223> OTHER INFORMATION: Cyclophilin A (cyclo) (accession number M19533)
      antisense primer 02

<400> SEQUENCE: 29
tctgctgtct ttggaacttt gtctg                                          25

<210> SEQ ID NO 30
<211> LENGTH: 28
<212> TYPE: DNA
<213> ORGANISM: Artificial Sequence
<220> FEATURE:
<223> OTHER INFORMATION: Cyclophilin A (cyclo) (accession number M19533)
      probe 02

<400> SEQUENCE: 30
atggtcaacc ccaccgtgtt cttcgaca                                       28
```

AZETIDINE DERIVATIVES USEFUL AS MODULATORS OF CORTICAL CATECHOLAMINERGIC NEUROTRANSMISSION

CROSS-REFERENCE TO RELATED APPLICATIONS

This application is a U.S. National Phase Application of International Application No. PCT/EP2017/079666, filed Nov. 17, 2017, which claims priority to European Application No. 16199545.1, filed Nov. 18, 2016, each of which are hereby incorporated by reference in their entirety.

REFERENCE TO SEQUENCE LISTING

The Sequence Listing submitted Mar. 27, 2020, as a text file named "37441_0050 U1_seq," created on Mar. 27, 2020, and having a size of 7,835 bytes is hereby incorporated by reference pursuant to 37 C.F.R. § 1.52(e)(5).

TECHNICAL FIELD

The present disclosure relates to novel 3-phenoxy-azetidine derivatives, useful for modulating levels of monoamines, such as dopamine, norepinephrine and serotonin, in cerebral cortical areas of the mammalian brain, and more specifically for the treatment of central nervous system disorders. The present disclosure also relates to the use of these compounds in a method for therapy and to pharmaceutical compositions comprising the compounds of the present disclosure.

BACKGROUND

The cerebral cortex encompasses several major regions that are involved in higher functions such as thought, feelings, memory and planning. Monoamines, such as dopamine, norepinephrine and serotonin, are important as neurotransmitters for mammalian cortical function. The ascending serotonergic and noradrenergic pathways innervate virtually all regions of the brain including the cerebral cortex. The dopaminergic neurons of the CNS have more distinct projections, including the meso-cortical pathway primarily innervating the frontal cortex, in addition to a number of specific subcortical pathways. Primary or secondary dysfunctions in the activity of the monoamine pathways innervating the cerebral cortex lead to aberrations of the activity at cortical dopamine, norepinephrine and serotonin receptors and subsequently to manifestations of psychiatric and neurological symptoms.

The monoamines of the cortex modulate several aspects of cortical functions controlling affect, anxiety, motivation, cognition, attention, arousal and wakefulness. Thus, the catecholamines dopamine and norepinephrine exert strong influence on the frontal cortical areas, the integrity of which is essential for the so-called executive cognitive functions, related to e.g. attention, planning of actions and impulse control. Norepinephrine is a major part in the circuitry regulating anxiety and fear and is thus believed to be dysregulated in anxiety disorders such as panic disorders, generalized anxiety disorder (GAD) and specific phobias. Concerning mood and affective functions, the usefulness of compounds facilitating particularly norepinephrine and serotonin neurotransmission in the treatment of depression and anxiety has strongly contributed to the widely-accepted concept that these neuro-transmitters are both involved in the regulation of affective functions.

Hamon et al. (Prog Neuro-Psychopharm & Bio Psych, 2013, 45, 54-63) discloses that compounds specifically affecting the transmission of monoamines, more precisely norepinephrine, dopamine and serotonin, are successfully used to alleviate the affective, cognitive, or attentional symptoms in patients suffering from e.g. depression, anxiety and attention deficit hyperactivity disorder (ADHD). In addition, Arnsten (Biol Psych, 2011, 69(12); 89-99) discloses that all current pharmacological treatments for ADHD facilitate catecholamine transmission. Furthermore, Wang (Front Cell Neurosci, 2015, 9; 1-23) discloses that modulation of monoaminergic transmission has been suggested as a promising principle for the treatment of autism spectrum disorders.

Trillo et al. (Neurosci & Biobehav Rev, 2013, 37; 1363-79) discloses that in Alzheimer's disease, progressive degeneration of ascending monoamine systems have been linked to cognitive as well as non-cognitive symptoms, and pharmacological interventions leading to enhanced monoamine transmission have been suggested as a strategy both for symptomatic and disease-modifying treatments of Alzheimer's disease.

Furthermore, the monoamine systems in the cortex are known to be directly or indirectly involved in the core symptoms of schizophrenia. It has been proposed that this disorder emerges as various pathological etiologies converge upon cortical synaptic processes leading to dysregulation of the cortical micro-circuitry, which is clinically manifested as the symptoms of schizophrenia (Harrison et al., Mol Psych, 2005, 10; 40-68). This cortical microcircuitry is regulated by several neurotransmitters, including glutamate, GABA, and dopamine. It has further been proposed that pharmacological enhancement of cortical dopamine transmission could restore the function of this microcircuitry, providing a useful strategy for improved treatment of schizophrenia (Abi-Dargham et al., Eur Psych, 2005, 20; 15-27).

WO 2004/113297 discloses aza-ring derivatives and their use as monoamine neurotransmitter re-uptake inhibitors. The compound 3-(3,4-dichlorophenoxy)azetidine in salt form and non-salt from, respectively, is one of the derivatives being exemplified.

EP 2754653 discloses azetidine derivatives and their use as monoamine neurotransmitter re-uptake inhibitors.

WO 2010/022055 and WO 2011/103196 disclose certain 3-phenoxy-azetidine derivatives as synthetic intermediates in the synthesis of inhibitors of voltage-gated sodium channels. Among the disclosed compounds in the former application are 3-(2,3-difluorophenoxy)-azetidine and 3-(2,6-difluorophenoxy)azetidine in their neutral form and among the ones in the latter application are 3-(2,3,4-trifluorophenoxy) azetidine and 3-(2,5-difluorophenoxy)azetidine, also in their neutral form. Furthermore, 3-(3,4-difluorophenoxy)azetidine and 3-(2,4-difluorophenoxy)azetidine in their neutral form are among the synthetic intermediates disclosed in both of the above mentioned applications.

WO 2007/148185 discloses 3-(3,4-difluorophenoxy)azetidine as one of the synthetic intermediates used in the synthesis of dipeptidyl peptidase 4 inhibitors.

WO 2010/084438 discloses certain 3-phenoxy-azetidine derivatives as synthetic intermediates in the synthesis of inhibitors of phosphodiesterase type 9. Among the disclosed compounds is the hydrochloric acid salt of 3-(3,4-difluorophenoxy)azetidine.

Claffey et al. (J Med Chem, 2012, 55, 9055-9068) discloses certain azetidine derivatives as synthetic intermediates in the synthesis of inhibitors of phosphodiesterase type 9. Among the disclosed compounds is 3-(2,5-difluorophenoxy)azetidine in its neutral form.

The database SciFinder discloses the compounds 3-(2,3-difluorophenoxy)azetidine, difluorophenoxy)azetidine, 3-(3,5-difluorophenoxy)azetidine, 3-(2,5-difluorophenoxy)azetidine, 3-(2,4-difluorophenoxy)azetidine, 3-(2,6-difluorophenoxy)azetidine, 3-(2,3,4-trifluorophenoxy)azetidine and 3-(2,3,4,5,6-pentafluorophenoxy)azetidine in their non-salt forms, respectively in the form of chemicals that are commercially available. Further, 3-(3,4-difluorophenoxy)azetidine, 3-(3,5-difluorophenoxy)azetidine, 3-(2,4-difluorophenoxy)azetidine and 3-(2,6-difluorophenoxy)azetidine as their hydrochloric acid salts are also provided as chemicals that are commercially available.

WO 2010/058018 discloses 3-phenyl-3-methoxypyrrolidine derivatives as modulators of cortical catecholaminergic neurotransmission.

WO 2010/058017 discloses 3-phenyl azetine derivatives useful as modulators of cortical cathecolaminergic neurotransmission.

WO 2016/030310 discloses substituted azetidine derivatives as TAAR (trace amine associated receptors) ligands.

SUMMARY

An object of the present disclosure is to provide novel therapeutically active compounds, especially useful in treatment of disorders in the central nervous system. A further object is the provision of compounds for modulation of dopamine and norepinephrine neurotransmission in the mammalian brain, including human brain. A still further object is the provision of novel compounds with a cortical enhancer profile. A further object is to provide compounds with therapeutic effects after oral administration. A still further object is the provision of compounds with more optimal pharmacodynamic and pharmacokinetic properties such as e.g. plasma half-life, bioavailability, solubility and in vitro and in vivo efficacy. A further object is to provide compounds being superior to presently known compounds in the treatment of several disorders related to dysfunctions of the CNS, in terms of efficacy and/or side effects.

The present disclosure concerns the compounds as disclosed herein displaying certain effects on monoamines in the cerebral cortex, and the use of these compounds in the treatment for certain CNS disorders. Unexpectedly, it has been found that compounds of the present disclosure produce regionally selective increases in catecholamine levels in the frontal cortex. Due to the specific modulatory effects by the monoamines on cortical functions related to cognition, attention and affect, compounds as disclosed herein can be used in the treatment of disorders characterized by impairment of such functions. Thus, compounds as disclosed herein can be used in the treatment of cognitive, affective, and anxiety disorders. The compounds can also be used to treat symptoms of schizophrenia, which is characterized by dysfunctions of the cerebral cortex manifested in cognitive impairment and psychosis.

It is known that the alpha 2 receptor antagonist idazoxan increases the release of dopamine and norepinephrine in prefrontal cortex via blockade of the alpha-2 receptor (see Devoto et al, Molecular Psychiatry (2001), 6(6), 657-664). While not wishing to be bound by any specific theory, it is believed that the compounds of the present disclosure may at least partly act by blocking the alpha 2 adrenergic receptor.

Further, compounds of the present disclosure have surprisingly been found not to bind with high affinity to human serotonin (5-HT), norepinephrine and dopamine transporters (i.e. do not inhibit the monoamine neurotransmitter up-take).

The present disclosure provides a pharmaceutical composition comprising a therapeutically effective amount of a compound of Formula I:

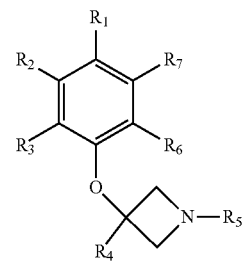

Formula I or an isotope labelled analog thereof, or a pharmaceutically acceptable salt thereof, wherein:

each of $R_1$, $R_2$, $R_3$, $R_6$ and $R_7$ represents H or F, $R_4$ represents H or $CH_3$ $R_5$ represents H or $C_1$-$C_4$alkyl, wherein at least two of $R_1$, $R_2$, $R_3$, $R_6$ and $R_7$ represent F, together with at least one pharmaceutically acceptable carrier, excipient and/or diluent.

Further, there is provided a compound of Formula I as described herein, or an isotope labelled analog thereof, or a pharmaceutically acceptable salt thereof, for use as a medicament. The medicament may be a medicament for the treatment and/or prevention of a disease, disorder and/or condition in which disease, disorder or condition is responsive to modulation of monoamines in the cerebral cortex.

There is also provided a compound of Formula I as described herein, or an isotope labelled analog thereof, or a pharmaceutically acceptable salt thereof, for use in the treatment and/or prevention of a disease, disorder and/or condition in which disease, disorder or condition is responsive to modulation of monoamines in the cerebral cortex.

There is also provided a use of a compound of Formula I as described herein, or an isotope labelled analog thereof, or a pharmaceutically acceptable salt thereof, for the manufacture of a medicament for the use in the treatment and/or prevention of a disease, disorder and/or condition in which disease, disorder or condition is responsive to modulation of monoamines in the cerebral cortex.

There is also provided a method for treatment and/or prevention or alleviation of a disease, disorder and/or condition of a human, which disorder, disease or condition is responsive to modulation of monoamines in the cerebral cortex, which method comprises the step of administering to a human in need thereof a therapeutically effective amount of a compound of Formula I as described herein, or an isotope labelled analog thereof, or a pharmaceutically acceptable salt thereof, or therapeutically active metabolites of compounds as disclosed herein.

There is also provided a compound of Formula I:

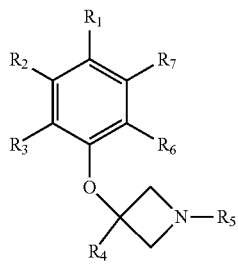

Formula I or an isotope labelled analog thereof, or a pharmaceutically acceptable salt thereof,
wherein:
each of $R_1$, $R_2$, $R_3$, $R_6$ and $R_7$ represents H or F,
$R_4$ represents H or $CH_3$
$R_5$ represents H or $C_1$-$C_4$alkyl,
wherein at least two of $R_1$, $R_2$, $R_3$, $R_6$ and $R_7$ represent F,
with the proviso that the compound of Formula I is not:
3-(2,3-difluorophenoxy)azetidine in non-salt form, or
3-(2,3,4-trifluorophenoxy)azetidine in non-salt form, or
3-(2,3,4,5,6-pentafluorophenoxy)azetidine in non-salt form, or
3-(2,4-difluorophenoxy)azetidine in non-salt form, or
3-(2,4-difluorophenoxy)azetidine hydrochloric acid salt, or
3-(2,5-difluorophenoxy)azetidine in non-salt form, or
3-(2,6-difluorophenoxy)azetidine in non-salt form, or
3-(2,6-difluorophenoxy)azetidine hydrochloric acid salt, or
3-(3,4-difluorophenoxy)azetidine in non-salt form, or
3-(3,4-difluorophenoxy)azetidine hydrochloric acid salt, or
3-(3,5-difluorophenoxy)azetidine in non-salt form, or
3-(3,5-difluorophenoxy)azetidine hydrochloric acid salt, or
3-(2,4,6-trifluorophenoxy)azetidine in non-salt form, or
3-(2,4,5-trifluorophenoxy)azetidine in non-salt form.

There is also provided a compound of Formula I:

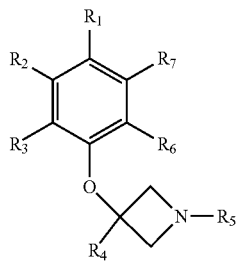

Formula I which is an isotope labelled analog of or a pharmaceutically acceptable salt of at least one of the following compounds:
3-(2,3-difluorophenoxy)azetidine,
3-(2,3,5-trifluorophenoxy)azetidine,
3-(2,3,5,6-tetrafluorophenoxy)-azetidine,
3-(2,3,6-trifluorophenoxy)azetidine,
3-(2,4,6-Trifluorophenoxy)azetidine,
3-(3,4,5-Trifluorophenoxy)azetidine,
3-(2,4,5-Trifluorophenoxy)azetidine,
3-(3,5-difluorophenoxy)azetidine,
with the proviso that the compound of Formula I is not 3-(3,5-difluorophenoxy)azetidine hydrochloric acid salt.

Other aspects of the present disclosure will be apparent to the person skilled in the art from the following detailed description and examples.

DETAILED DESCRIPTION OF THE DISCLOSURE

The present disclosure provides a pharmaceutical composition comprising a therapeutically effective amount of a compound of Formula I:

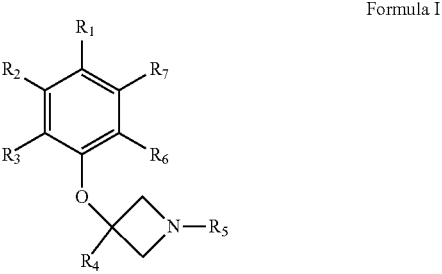

Formula I or an isotope labelled analog thereof, or a pharmaceutically acceptable salt thereof,
wherein:
each of $R_1$, $R_2$, $R_3$, $R_6$ and $R_7$ represents H or F,
$R_4$ represents H or $CH_3$
$R_5$ represents H or $C_1$-$C_4$alkyl,
wherein at least two of $R_1$, $R_2$, $R_3$, $R_6$ and $R_7$ represent F,
together with at least one pharmaceutically acceptable carrier, excipient and/or diluent.

The compound of Formula I of the pharmaceutical composition described herein may have the following values for $R_1$, $R_2$, $R_3$, $R_4$, $R_5$, $R_6$ and $R_7$.

At least one of $R_1$, $R_2$, $R_3$, and $R_7$ may represent F, and $R_6$ may represent F.

Alternatively,
at least one of $R_1$, $R_2$, $R_3$, and $R_6$ may represent F, and $R_7$ may represent F.

$R_4$ may be H. Alternatively, $R_4$ may be $CH_3$.

$R_5$ may be H. Alternatively, $R_5$ may be $C_1$-$C_4$alkyl optionally substituted with 0, 1, 2, 3 or 4 F. Examples of $C_1$-$C_4$alkyl include methyl, ethyl, n-propyl, isopropyl, n-butyl, sec-butyl and tert-butyl.

There is provided a pharmaceutical composition as described herein, wherein the compound of Formula I is a compound of Formula Ia.

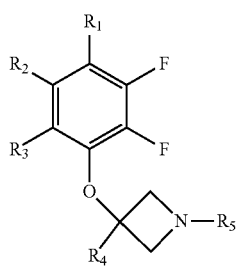

Formula Ia or an isotope labelled analog thereof, or a pharmaceutically acceptable salt thereof, wherein:
each of $R_1$, $R_2$ and $R_3$ independently represents H or F,
$R_4$ represents H or $CH_3$, and
$R_5$ represents H or $C_1$-$C_4$alkyl.

For the compound of Formula Ia, at least one of $R_1$, $R_2$ and $R_3$ may represent F.

Further, for the compound of Formula I such as in the compound of Formula Ia, $R_1$ may be H. For instance, when $R_1$ is H at least two of $R_2$, $R_3$, $R_6$ and $R_7$ may be F. In an example, $R_1$ is H, $R_6$ is F, $R_7$ is F, $R_2$ is H or F and $R_3$ is H or F. In a further example $R_1$ is H, $R_6$ is F, $R_7$ is H, $R_2$ is H or F and $R_3$ is H or F. In still a further example, $R_1$ is H, $R_6$ is H, $R_7$ is F, $R_2$ is H or F and $R_3$ is H or F. For these examples, $R_4$ and $R_5$ may have the values described herein.

There is provided a pharmaceutical composition as described herein wherein the compound of Formula I is not:
3-(2,3-difluorophenoxy)azetidine in non-salt form, or
3-(2,3,4-trifluorophenoxy)azetidine in non-salt form, or
3-(2,3,4,5,6-pentafluorophenoxy)azetidine in non-salt form.

Further, there is provided a pharmaceutical composition as described herein wherein the compound of Formula I is not:
3-(2,3-difluorophenoxy)azetidine or a salt thereof, or
3-(2,3,4-trifluorophenoxy)azetidine or a salt thereof, or
3-(2,3,4,5,6-pentafluorophenoxy)azetidine or a salt thereof.

There is also provided a pharmaceutical composition as described herein wherein the compound of Formula I is not:
3-(2,3-difluorophenoxy)azetidine in non-salt form, or
3-(2,3,4-trifluorophenoxy)azetidine in non-salt form, or
3-(2,3,4,5,6-pentafluorophenoxy)azetidine in non-salt form, or
3-(2,4-difluorophenoxy)azetidine in non-salt form, or
3-(2,4-difluorophenoxy)azetidine hydrochloric acid salt, or
3-(2,5-difluorophenoxy)azetidine in non-salt form, or
3-(2,6-difluorophenoxy)azetidine in non-salt form, or
3-(2,6-difluorophenoxy)azetidine hydrochloric acid salt, or
3-(3,4-difluorophenoxy)azetidine in non-salt form, or
3-(3,4-difluorophenoxy)azetidine hydrochloric acid salt, or
3-(3,5-difluorophenoxy)azetidine in non-salt form, or
3-(3,5-difluorophenoxy)azetidine hydrochloric acid salt, or
3-(2,4,6-trifluorophenoxy)azetidine in non-salt form, or
3-(2,4,5-trifluorophenoxy)azetidine in non-salt form.

There is also provided a pharmaceutical composition as described herein wherein the compound of Formula I is not:
3-(2,3-difluorophenoxy)azetidine or a salt thereof, or
3-(2,3,4-trifluorophenoxy)azetidine or a salt thereof, or
3-(2,3,4,5,6-pentafluorophenoxy)azetidine or a salt thereof, or
3-(2,4-difluorophenoxy)azetidine or a salt thereof, or
3-(2,5-difluorophenoxy)azetidine or a salt thereof, or
3-(2,6-difluorophenoxy)azetidine or a salt thereof, or
3-(3,4-difluorophenoxy)azetidine or a salt thereof, or
3-(3,5-difluorophenoxy)azetidine or a salt thereof, or
3-(2,4,6-trifluorophenoxy)azetidine or a salt thereof, or
3-(2,4,5-trifluorophenoxy)azetidine or a salt thereof.

There is also provided a pharmaceutical composition as described herein, wherein the compound of Formula I is at least one of the following:
3-(2,3-difluorophenoxy)azetidine,
3-(2,3,5-trifluorophenoxy)azetidine,
3-(2,3,5,6-tetrafluorophenoxy)-azetidine,
3-methyl-3-(2,3,5-trifluoro-phenoxy)azetidine,
3-(2,3-difluorophenoxy)-1-methylazetidine,
3-(2,3-difluorophenoxy)-1-ethylazetidine,
3-(2,3-difluorophenoxy)-3-methylazetidine,
3-(2,3-difluorophenoxy)-1,3-dimethylazetidine,
3-(2,3-difluorophenoxy)-1-ethyl-3-methylazetidine,
3-(2,3,4-trifluorophenoxy)azetidine,
1-methyl-3-(2,3,4-trifluoro-phenoxy)azetidine,
1-ethyl-3-(2,3,4-trifluoro-phenoxy)azetidine,
3-methyl-3-(2,3,4-trifluoro-phenoxy)azetidine,
1,3-dimethyl-3-(2,3,4-trifluorophenoxy)azetidine,
1-ethyl-3-methyl-3-(2,3,4-trifluorophenoxy)azetidine,
1-methyl-3-(2,3,5-trifluoro-phenoxy)azetidine,
1-ethyl-3-(2,3,5-trifluoro-phenoxy)azetidine,
1,3-dimethyl-3-(2,3,5-trifluorophenoxy)azetidine,
1-ethyl-3-methyl-3-(2,3,5-trifluorophenoxy)azetidine,
3-(2,3,6-trifluorophenoxy)azetidine,
1-methyl-3-(2,3,6-trifluoro-phenoxy)azetidine,
1-ethyl-3-(2,3,6-trifluoro-phenoxy)azetidine,
3-methyl-3-(2,3,6-trifluoro-phenoxy)azetidine,
1,3-dimethyl-3-(2,3,6-trifluoro-phenoxy)azetidine,
1-ethyl-3-methyl-3-(2,3,6-trifluorophenoxy)azetidine,
3-(2,3,4,5-tetrafluoro-phenoxy)azetidine,
1-methyl-3-(2,3,4,5-tetrafluoro-phenoxy)azetidine,
1-ethyl-3-(2,3,4,5-tetrafluoro-phenoxy)azetidine,
3-methyl-3-(2,3,4,5-tetrafluorophenoxy)azetidine,
1,3-dimethyl-3-(2,3,4,5-tetrafluorophenoxy)azetidine,
1-ethyl-3-methyl-3-(2,3,4,5-tetrafluorophenoxy)azetidine,
3-(2,3,4,6-tetrafluorophenoxy)-azetidine,
1-methyl-3-(2,3,4,6-tetrafluorophenoxy)azetidine,
1-ethyl-3-(2,3,4,6-tetrafluoro-phenoxy)azetidine,
3-methyl-3-(2,3,4,6-tetrafluorophenoxy)azetidine,
1,3-dimethyl-3-(2,3,4,6-tetrafluorophenoxy)azetidine,
1-ethyl-3-methyl-3-(2,3,4,6-tetrafluorophenoxy)azetidine,
1-methyl-3-(2,3,5,6-tetrafluorophenoxy)azetidine,
1-ethyl-3-(2,3,5,6-tetrafluorophenoxy)azetidine,
3-methyl-3-(2,3,5,6-tetrafluorophenoxy)azetidine,
1,3-dimethyl-3-(2,3,5,6-tetrafluorophenoxy)azetidine,
1-ethyl-3-methyl-3-(2,3,5,6-tetrafluorophenoxy)azetidine,
3-(2,3,4,5,6-pentafluorophenoxy)azetidine,
1-methyl-3-(2,3,4,5,6-pentafluorophenoxy)azetidine,
1-ethyl-3-(2,3,4,5,6-pentafluorophenoxy)azetidine,
3-methyl-3-(2,3,4,5,6-pentafluorophenoxy)azetidine,
1,3-dimethyl-3-(2,3,4,5,6-pentafluorophenoxy)azetidine,
1-ethyl-3-methyl-3-(2,3,4,5,6-pentafluorophenoxy)azetidine,
3-(2,4,6-trifluorophenoxy)azetidine,
3-(3,4,5-trifluorophenoxy)azetidine,
3-(2,4,5-trifluorophenoxy)azetidine,
3-(3,5-difluorophenoxy)azetidine,
3-(2,4,6-trifluorophenoxy)-1-ethylazetidine,
3-(2,3,6-trifluorophenoxy)-1-propylazetidine,
3-(3,5-difluorophenoxy)-1-methylazetidine,
3-(3,5-difluorophenoxy)-1-ethylazetidine,
3-(3,5-difluorophenoxy)-3-methylazetidine,
3-(3,5-difluorophenoxy)-1,3-dimethylazetidine,
3-(3,5-difluorophenoxy)-1-ethyl-3-methylazetidine,
3-(2,3-difluorophenoxy)-1-($^2H_3$)methylazetidine,
3-(2,3-difluorophenoxy)-1-[(1,1,2,2,2-$^2H_5$)ethyl]azetidine,
3-(2,3-difluorophenoxy)(3-$^2H$)azetidine,
3-(2,3-difluorophenoxy)(2,2,4,4-$^2H_4$)azetidine,
3-(2,3-difluorophenoxy)(2,2,3,4,4-$^2H_5$)azetidine,
3-[2,3-difluoro(4,6-$^2H_2$)phenoxy]azetidine,
3-[2,3-difluoro(4,6-$^2H_2$)phenoxy](3-$^2H$)azetidine,
3-[2,3-difluoro(4,6-$^2H_2$)phenoxy](2,2,4,4-$^2H_4$)azetidine,
3-[2,3-difluoro(4,6-$^2H_2$)phenoxy](2,2,3,4,4-$^2H_5$)azetidine,
3-(3,5-difluorophenoxy)-1-($^2H_3$)methylazetidine,
3-(3,5-difluorophenoxy)-1-[(1,1,2,2,2-$^2H_5$)ethyl]azetidine,
3-(3,5-difluorophenoxy)(3-$^2H$)azetidine,
3-(3,5-difluorophenoxy)(2,2,4,4-$^2H_4$)azetidine,
3-(3,5-difluorophenoxy)(2,2,3,4,4-$^2H_5$)azetidine,
3-[3,5-difluoro(2,4,6-$^2H_3$)phenoxy]azetidine,
3-[3,5-difluoro(2,4,6-$^2H_3$)phenoxy](3-$^2H$)azetidine, 3-[3,5-difluoro(2,4,6-$^2$H$_3$)phenoxy](2,2,4,4-$^2$H$_4$)azetidine,
3-[3,5-difluoro(2,4,6-$^2$H$_3$)phenoxy](2,2,3,4,4-$^2$H$_5$)azetidine,
1-($^2$H$_3$)methyl-3-(2,3,5,6-tetrafluorophenoxy)azetidine,
1-[(1,1,2,2,2-$^2$H$_5$)ethyl]-3-(2,3,5,6-tetrafluorophenoxy)azetidine,
3-(2,3,5,6-tetrafluorophenoxy)(3-$^2$H)azetidine,
3-(2,3,5,6-tetrafluorophenoxy)(2,2,4,4-$^2$H$_4$)azetidine,
3-(2,3,5,6-tetrafluorophenoxy)(2,2,3,4,4-$^2$H$_5$)azetidine,
3-[2,3,5,6-tetrafluoro(4-$^2$H)phenoxy]azetidine,
3-[2,3,5,6-tetrafluoro(4-$^2$H)phenoxy](3-$^2$H)azetidine,
3-[2,3,5,6-tetrafluoro(4-$^2$H)phenoxy](2,2,4,4-$^2$H$_4$)azetidine,
3-[2,3,5,6-tetrafluoro(4-$^2$H)phenoxy](2,2,3,4,4-$^2$H$_5$)azetidine,
1-($^2$H$_3$)methyl-3-(2,3,6-trifluorophenoxy)azetidine,
1-[(1,1,2,2,2-$^2$H$_5$)ethyl]-3-(2,3,6-trifluorophenoxy)azetidine,
3-(2,3,6-trifluorophenoxy)(3-$^2$H)azetidine,
3-(2,3,6-trifluorophenoxy)(2,2,4,4-$^2$H$_4$)azetidine,
3-(2,3,6-trifluorophenoxy)(2,2,3,4,4-$^2$H$_5$)azetidine,
3-[2,3,6-trifluoro(4-$^2$H)phenoxy]azetidine,
3-[2,3,6-trifluoro(4-$^2$H)phenoxy](3-$^2$H)azetidine,
3-[2,3,6-trifluoro(4-$^2$H)phenoxy](2,2,4,4-$^2$H$_4$)azetidine,
3-[2,3,6-trifluoro(4-$^2$H)phenoxy](2,2,3,4,4-$^2$H$_5$)azetidine,
1-($^2$H$_3$)methyl-3-(2,3,5-trifluorophenoxy)azetidine,
1-[(1,1,2,2,2-$^2$H$_5$)ethyl]-3-(2,3,5-trifluorophenoxy)azetidine,
3-(2,3,5-trifluorophenoxy)(3-$^2$H)azetidine,
3-(2,3,5-trifluorophenoxy)(2,2,4,4-$^2$H$_4$)azetidine,
3-(2,3,5-trifluorophenoxy)(2,2,3,4,4-$^2$H$_5$)azetidine,
3-[2,3,5-trifluoro(4-$^2$H)phenoxy]azetidine,
3-[2,3,5-trifluoro(4-$^2$H)phenoxy](3-$^2$H)azetidine,
3-[2,3,5-trifluoro(4-$^2$H)phenoxy](2,2,4,4-$^2$H$_4$)azetidine,
3-[2,3,5-trifluoro(4-$^2$H)phenoxy](2,2,3,4,4-$^2$H$_5$)azetidine,
or an isotope labelled analog thereof, or a pharmaceutically acceptable salt thereof.

There is also provided a pharmaceutical composition as described herein, wherein the compound of Formula I is at least one of the following:
3-(2,3,5-trifluorophenoxy)azetidine,
3-(2,3,5,6-tetrafluorophenoxy)-azetidine,
3-methyl-3-(2,3,5-trifluoro-phenoxy)azetidine,
3-(2,3-difluorophenoxy)-1-methylazetidine,
3-(2,3-difluorophenoxy)-1-ethylazetidine,
3-(2,3-difluorophenoxy)-3-methylazetidine,
3-(2,3-difluorophenoxy)-1,3-dimethylazetidine,
3-(2,3-difluorophenoxy)-1-ethyl-3-methylazetidine,
1-methyl-3-(2,3,4-trifluoro-phenoxy)azetidine,
1-ethyl-3-(2,3,4-trifluoro-phenoxy)azetidine,
3-methyl-3-(2,3,4-trifluoro-phenoxy)azetidine,
1,3-dimethyl-3-(2,3,4-trifluorophenoxy)azetidine,
1-ethyl-3-methyl-3-(2,3,4-trifluorophenoxy)azetidine,
1-methyl-3-(2,3,5-trifluoro-phenoxy)azetidine,
1-ethyl-3-(2,3,5-trifluoro-phenoxy)azetidine,
1,3-dimethyl-3-(2,3,5-trifluorophenoxy)azetidine,
1-ethyl-3-methyl-3-(2,3,5-trifluorophenoxy)azetidine,
3-(2,3,6-trifluorophenoxy)azetidine,
1-methyl-3-(2,3,6-trifluoro-phenoxy)azetidine,
1-ethyl-3-(2,3,6-trifluoro-phenoxy)azetidine,
3-methyl-3-(2,3,6-trifluoro-phenoxy)azetidine,
1,3-dimethyl-3-(2,3,6-trifluoro-phenoxy)azetidine,
1-ethyl-3-methyl-3-(2,3,6-trifluorophenoxy)azetidine,
3-(2,3,4,5-tetrafluoro-phenoxy)azetidine,
1-methyl-3-(2,3,4,5-tetrafluoro-phenoxy)azetidine,
1-ethyl-3-(2,3,4,5-tetrafluoro-phenoxy)azetidine,
3-methyl-3-(2,3,4,5-tetrafluorophenoxy)azetidine,
1,3-dimethyl-3-(2,3,4,5-tetrafluorophenoxy)azetidine,
1-ethyl-3-methyl-3-(2,3,4,5-tetrafluorophenoxy)azetidine,
3-(2,3,4,6-tetrafluorophenoxy)-azetidine,
1-methyl-3-(2,3,4,6-tetrafluorophenoxy)azetidine,
1-ethyl-3-(2,3,4,6-tetrafluoro-phenoxy)azetidine,
3-methyl-3-(2,3,4,6-tetrafluorophenoxy)azetidine,
1,3-dimethyl-3-(2,3,4,6-tetrafluorophenoxy)azetidine,
1-ethyl-3-methyl-3-(2,3,4,6-tetrafluorophenoxy)azetidine,
1-methyl-3-(2,3,5,6-tetrafluorophenoxy)azetidine,
1-ethyl-3-(2,3,5,6-tetrafluorophenoxy)azetidine,
3-methyl-3-(2,3,5,6-tetrafluorophenoxy)azetidine,
1,3-dimethyl-3-(2,3,5,6-tetrafluorophenoxy)azetidine,
1-ethyl-3-methyl-3-(2,3,5,6-tetrafluorophenoxy)azetidine,
3-(2,3,4,5,6-pentafluorophenoxy)azetidine,
1-methyl-3-(2,3,4,5,6-pentafluorophenoxy)azetidine,
1-ethyl-3-(2,3,4,5,6-pentafluorophenoxy)azetidine,
3-methyl-3-(2,3,4,5,6-pentafluorophenoxy)azetidine,
1,3-dimethyl-3-(2,3,4,5,6-pentafluorophenoxy)azetidine,
1-ethyl-3-methyl-3-(2,3,4,5,6-pentafluorophenoxy)azetidine,
3-(3,4,5-trifluorophenoxy)azetidine,
3-(2,4,5-trifluorophenoxy)azetidine,
3-(2,4,6-trifluorophenoxy)-1-ethylazetidine,
3-(2,3,6-trifluorophenoxy)-1-propylazetidine,
3-(3,5-difluorophenoxy)-1-methylazetidine,
3-(3,5-difluorophenoxy)-1-ethylazetidine,
3-(3,5-difluorophenoxy)-3-methylazetidine,
3-(3,5-difluorophenoxy)-1,3-dimethylazetidine,
3-(3,5-difluorophenoxy)-1-ethyl-3-methylazetidine,
3-(2,3-difluorophenoxy)-1-($^2$H$_3$)methylazetidine,
3-(2,3-difluorophenoxy)-1-[(1,1,2,2,2-$^2$H$_5$)ethyl]azetidine,
3-(2,3-difluorophenoxy)(3-$^2$H)azetidine,
3-(2,3-difluorophenoxy)(2,2,4,4-$^2$H$_4$)azetidine,
3-(2,3-difluorophenoxy)(2,2,3,4,4-$^2$H$_5$)azetidine,
3-[2,3-difluoro(4,6-$^2$H$_2$)phenoxy]azetidine,
3-[2,3-difluoro(4,6-$^2$H$_2$)phenoxy](3-$^2$H)azetidine,
3-[2,3-difluoro(4,6-$^2$H$_2$)phenoxy](2,2,4,4-$^2$H$_4$)azetidine,
3-[2,3-difluoro(4,6-$^2$H$_2$)phenoxy](2,2,3,4,4-$^2$H$_5$)azetidine,
3-(3,5-difluorophenoxy)-1-($^2$H$_3$)methylazetidine,
3-(3,5-difluorophenoxy)-1-[(1,1,2,2,2-$^2$H$_5$)ethyl]azetidine,
3-(3,5-difluorophenoxy)(3-$^2$H)azetidine;
3-(3,5-difluorophenoxy)(2,2,4,4-$^2$H$_4$)azetidine,
3-(3,5-difluorophenoxy)(2,2,3,4,4-$^2$H$_5$)azetidine,
3-[3,5-difluoro(2,4,6-$^2$H$_3$)phenoxy]azetidine,
3-[3,5-difluoro(2,4,6-$^2$H$_3$)phenoxy](3-$^2$H)azetidine,
3-[3,5-difluoro(2,4,6-$^2$H$_3$)phenoxy](2,2,4,4-$^2$H$_4$)azetidine,
3-[3,5-difluoro(2,4,6-$^2$H$_3$)phenoxy](2,2,3,4,4-$^2$H$_5$)azetidine,
1-($^2$H$_3$)methyl-3-(2,3,5,6-tetrafluorophenoxy)azetidine,
1-[(1,1,2,2,2-$^2$H$_5$)ethyl]-3-(2,3,5,6-tetrafluorophenoxy)azetidine,
3-(2,3,5,6-tetrafluorophenoxy)(3-2H)azetidine,
3-(2,3,5,6-tetrafluorophenoxy)(2,2,4,4-$^2$H$_4$)azetidine,
3-(2,3,5,6-tetrafluorophenoxy)(2,2,3,4,4-$^2$H$_5$)azetidine,
3-[2,3,5,6-tetrafluoro(4-$^2$H)phenoxy]azetidine,
3-[2,3,5,6-tetrafluoro(4-$^2$H)phenoxy](3-$^2$H)azetidine,
3-[2,3,5,6-tetrafluoro(4-$^2$H)phenoxy](2,2,4,4-$^2$H$_4$)azetidine,
3-[2,3,5,6-tetrafluoro(4-$^2$H)phenoxy](2,2,3,4,4-$^2$H$_5$)azetidine,
1-($^2$H$_3$)methyl-3-(2,3,6-trifluorophenoxy)azetidine,
1-[(1,1,2,2,2-$^2$H$_5$)ethyl]-3-(2,3,6-trifluorophenoxy)azetidine,
3-(2,3,6-trifluorophenoxy)(3-$^2$H)azetidine,
3-(2,3,6-trifluorophenoxy)(2,2,4,4-$^2$H$_4$)azetidine,
3-(2,3,6-trifluorophenoxy)(2,2,3,4,4-$^2$H$_5$)azetidine,
3-[2,3,6-trifluoro(4-$^2$H)phenoxy]azetidine,
3-[2,3,6-trifluoro(4-$^2$H)phenoxy](3-$^2$H)azetidine,
3-[2,3,6-trifluoro(4-$^2$H)phenoxy](2,2,4,4-$^2$H$_4$)azetidine, 3-[2,3,6-trifluoro(4-$^2$H)phenoxy](2,2,3,4,4-$^2$H$_5$)azetidine,
1-($^2$H$_3$)methyl-3-(2,3,5-trifluorophenoxy)azetidine,
1-[(1,1,2,2,2-$^2$H$_5$)ethyl]-3-(2,3,5-trifluorophenoxy)azetidine,
3-(2,3,5-trifluorophenoxy)(3-$^2$H)azetidine,
3-(2,3,5-trifluorophenoxy)(2,2,4,4-$^2$H$_4$)azetidine,
3-(2,3,5-trifluorophenoxy)(2,2,3,4,4-$^2$H$_5$)azetidine,
3-[2,3,5-trifluoro(4-$^2$H)phenoxy]azetidine,
3-[2,3,5-trifluoro(4-$^2$H)phenoxy](3-$^2$H)azetidine,
3-[2,3,5-trifluoro(4-$^2$H)phenoxy](2,2,4,4-$^2$H$_4$)azetidine,
3-[2,3,5-trifluoro(4-$^2$H)phenoxy](2,2,3,4,4-$^2$H$_5$)azetidine,
or an isotope labelled analog thereof, or a pharmaceutically acceptable salt thereof.

There is also provided a pharmaceutical composition as described herein, wherein the compound of Formula I is at least one of the following:
3-(2,3-difluorophenoxy)azetidine,
3-(2,3,5-trifluorophenoxy)azetidine,
3-(2,3,5,6-tetrafluorophenoxy)-azetidine,
3-methyl-3-(2,3,5-trifluoro-phenoxy)azetidine,
3-(2,3-difluorophenoxy)-1-methylazetidine,
3-(2,3,4-trifluorophenoxy)azetidine,
3-(2,3,6-trifluorophenoxy)azetidine,
1-ethyl-3-(2,3,6-trifluoro-phenoxy)azetidine,
1-methyl-3-(2,3,5,6-tetrafluorophenoxy)azetidine,
1-ethyl-3-(2,3,5,6-tetrafluorophenoxy)azetidine,
3-(2,3,4,5,6-pentafluorophenoxy)azetidine,
3-(2,4,6-trifluorophenoxy)azetidine,
3-(3,4,5-trifluorophenoxy)azetidine,
3-(2,4,5-trifluorophenoxy)azetidine,
3-(3,5-difluorophenoxy)azetidine,
3-(2,4,6-trifluorophenoxy)-1-ethylazetidine,
3-(2,3,6-trifluorophenoxy)-1-propylazetidine,
3-(3,5-difluorophenoxy)-1-methylazetidine,
3-(2,3-difluorophenoxy)-1-($^2$H$_3$)methylazetidine,
3-(3,5-difluorophenoxy)-1-($^2$H$_3$)methylazetidine,
3-[3,5-difluoro(2,4,6-$^2$H$_3$)phenoxy]azetidine oxalic acid salt,
1-[(1,1,2,2,2-$^2$H$_5$)ethyl]-3-(2,3,6-trifluorophenoxy)azetidine,
or an isotope labelled analog thereof, or a pharmaceutically acceptable salt thereof.

There is also provided a pharmaceutical composition as described herein, wherein the compound of Formula I is at least one of the following:
3-(2,3,5-trifluorophenoxy)azetidine,
3-(2,3,5,6-tetrafluorophenoxy)-azetidine,
3-methyl-3-(2,3,5-trifluoro-phenoxy)azetidine,
3-(2,3-difluorophenoxy)-1-methylazetidine,
3-(2,3,6-trifluorophenoxy)azetidine,
1-ethyl-3-(2,3,6-trifluoro-phenoxy)azetidine,
1-methyl-3-(2,3,5,6-tetrafluorophenoxy)azetidine,
1-ethyl-3-(2,3,5,6-tetrafluorophenoxy)azetidine,
3-(3,4,5-trifluorophenoxy)azetidine,
3-(2,4,6-trifluorophenoxy)-1-ethylazetidine,
3-(2,3,6-trifluorophenoxy)-1-propylazetidine,
3-(3,5-difluorophenoxy)-1-methylazetidine,
3-(2,3-difluorophenoxy)-1-($^2$H$_3$)methylazetidine,
3-(3,5-difluorophenoxy)-1-($^2$H$_3$)methylazetidine,
3-[3,5-difluoro(2,4,6-$^2$H$_3$)phenoxy]azetidine oxalic acid salt,
1-[(1,1,2,2,2-$^2$H$_5$)ethyl]-3-(2,3,6-trifluorophenoxy)azetidine,
or an isotope labelled analog thereof, or a pharmaceutically acceptable salt thereof.

There is also provided a pharmaceutical composition as described herein, wherein the compound of Formula I is at least one of the following:
3-(2,3-difluorophenoxy)azetidine,
3-(2,3,5-trifluorophenoxy)azetidine,
3-(2,3,5,6-tetrafluorophenoxy)-azetidine,
3-(2,3,6-trifluorophenoxy)azetidine,
3-(2,4,6-Trifluorophenoxy)azetidine,
3-(3,4,5-Trifluorophenoxy)azetidine,
3-(2,4,5-Trifluorophenoxy)azetidine,
3-(3,5-difluorophenoxy)azetidine.

There is also provided a pharmaceutical composition as described herein, wherein the compound of Formula I is at least one of the following:
3-(2,3-difluorophenoxy)azetidine,
3-(2,3,5,6-tetrafluorophenoxy)azetidine,
3-(3,5-difluorophenoxy)azetidine,
or an isotope labelled analog thereof, or a pharmaceutically acceptable salt thereof.

The present disclosure also provides a pharmaceutically acceptable salt of an isotope labelled analog of the compound of Formula I such as the compound of Formula Ia described herein. The isotope labelled analog may be a deuterated analog. The isotope labelled analog of the compound of Formula I such as the compound of Formula Ia may form part of the pharmaceutical composition described herein.

The present disclosure also provides a compound of Formula I:

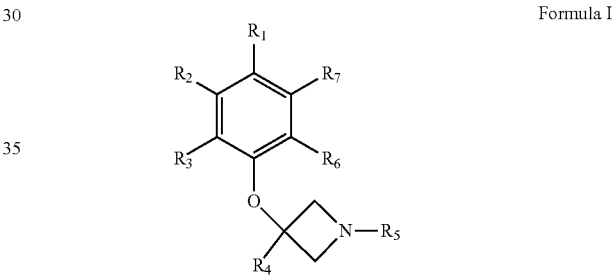

Formula I or an isotope labelled analog thereof, or a pharmaceutically acceptable salt thereof,
wherein:
each of $R_1$, $R_2$, $R_3$, $R_6$ and $R_7$ represents H or F,
$R_4$ represents H or $CH_3$
$R_5$ represents H or $C_1$-$C_4$alkyl,
wherein at least two of $R_1$, $R_2$, $R_3$, $R_6$ and $R_7$ represent F, with the proviso that the compound of Formula I is not:
3-(2,3-difluorophenoxy)azetidine in non-salt form, or
3-(2,3,4-trifluorophenoxy)azetidine in non-salt form, or
3-(2,3,4,5,6-pentafluorophenoxy)azetidine in non-salt form, or
3-(2,4-difluorophenoxy)azetidine in non-salt form, or
3-(2,4-difluorophenoxy)azetidine hydrochloric acid salt, or
3-(2,5-difluorophenoxy)azetidine in non-salt form, or
3-(2,6-difluorophenoxy)azetidine in non-salt form, or
3-(2,6-difluorophenoxy)azetidine hydrochloric acid salt, or
3-(3,4-difluorophenoxy)azetidine in non-salt form, or
3-(3,4-difluorophenoxy)azetidine hydrochloric acid salt, or
3-(3,5-difluorophenoxy)azetidine in non-salt form, or
3-(3,5-difluorophenoxy)azetidine hydrochloric acid salt, or
3-(2,4,6-trifluorophenoxy)azetidine in non-salt form, or
3-(2,4,5-trifluorophenoxy)azetidine in non-salt form.

Further, there is provided a compound of Formula I as described herein, or an isotope labelled analog thereof, or a pharmaceutically acceptable salt thereof, with the proviso that the compound of Formula I is not:
3-(2,3-difluorophenoxy)azetidine or a salt thereof, or
3-(2,3,4-trifluorophenoxy)azetidine or a salt thereof, or
3-(2,3,4,5,6-pentafluorophenoxy)azetidine or a salt thereof, or
3-(2,4-difluorophenoxy)azetidine or salt thereof, or
3-(2,5-difluorophenoxy)azetidine or a salt thereof, or
3-(2,6-difluorophenoxy)azetidine or salt thereof, or
3-(3,4-difluorophenoxy)azetidine or a salt thereof, or
3-(3,5-difluorophenoxy)azetidine or a salt thereof, or
3-(2,4,6-trifluorophenoxy)azetidine or a salt thereof, or
3-(2,4,5-trifluorophenoxy)azetidine or a salt thereof.

The compound of Formula I described herein may have the following values for $R_1$, $R_2$, $R_3$, $R_4$, $R_5$, $R_6$ and $R_7$.

At least one of $R_1$, $R_2$, $R_3$, and $R_7$ may represent F, and $R_6$ may represent F.

Alternatively, at least one of $R_1$, $R_2$, $R_3$, and $R_6$ may represent F, and
$R_7$ may represent F.

$R_4$ may be H. Alternatively, $R_4$ may be $CH_3$.

$R_5$ may be H. Alternatively, $R_5$ may be $C_1$-$C_4$alkyl substituted with 0, 1, 2, 3 or 4 F. Examples of $C_1$-$C_4$alkyl include methyl, ethyl, n-propyl, isopropyl, n-butyl, sec-butyl and tert-butyl.

In the compound of Formula I, both $R_6$ and $R_7$ may be F thereby providing
a compound of Formula Ia having the following chemical structure:

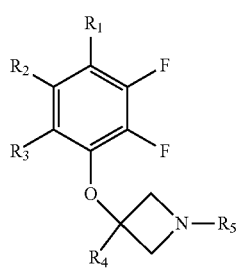

Formula Ia or a pharmaceutically acceptable salt thereof,
wherein
each $R_1$, $R_2$ and $R_3$ independently represents H or F,
$R_4$ is H or $CH_3$, and
$R_5$ is H or $C_1$-$C_4$alkyl
with the proviso that the compound is not:
3-(2,3-difluorophenoxy)azetidine in non-salt form, or
3-(2,3,4-trifluorophenoxy)azetidine in non-salt form, or
3-(2,3,4,5,6-pentafluorophenoxy)azetidine in non-salt form.

Thus, it will be appreciated that the scope defining the compound of Formula Ia as described herein may not include the non-salt form of the following compounds: 3-(2,3-difluorophenoxy)azetidine, 3-(2,3,4-trifluorophenoxy)azetidine, and 3-(2,3,4,5,6-pentafluorophenoxy)azetidine. Additionally, 3-(2,4,6-trifluorophenoxy)azetidine and 3-(2,4,5-trifluorophenoxy)azetidine in non-salt form may be excluded. However, the scope defining the compound of Formula Ia as described herein may include a pharmaceutically acceptable salt of the following compounds: 3-(2,3-difluorophenoxy)azetidine, 3-(2,3,4-trifluorophenoxy)azetidine, and 3-(2,3,4,5,6-pentafluorophenoxy)azetidine, and optionally 3-(2,4,6-trifluorophenoxy)azetidine and/or 3-(2,4,5-trifluorophenoxy)azetidine.

The compounds of Formula I such as the compound of Formula Ia as described herein are 3-phenoxy-azetidine derivatives.

In a further example, there is provided a compound of Formula I as described herein wherein the compounds 3-(2,3-difluorophenoxy)azetidine, 3-(2,3,4-trifluorophenoxy)azetidine, 3-(2,3,4,5,6-pentafluorophenoxy)azetidine are excluded, i.e. these compounds are excluded as such, i.e. in salt and/or non-salt form. Additionally, 3-(2,4,6-trifluorophenoxy)azetidine and 3-(2,4,5-trifluorophenoxy)azetidine may be excluded as such, in salt and/or non-salt form.

There is also provided a compound of Formula Ia as described herein, or an isotope labelled analog thereof, or a pharmaceutically acceptable salt thereof,
wherein:
at least one of $R_1$, $R_2$ and $R_3$ represents F.

There is also provided a compound of Formula I as described herein, or an isotope labelled analog thereof, or a pharmaceutically acceptable salt thereof,
wherein:
$R_1$ is H.

For instance, when $R_1$ is H at least two of $R_2$, $R_3$, $R_6$ and $R_7$ may be F. In an example, $R_1$ is H, $R_6$ is F, $R_7$ is F, $R_2$ is H or F and $R_3$ is H or F. In a further example $R_1$ is H, $R_6$ is F, $R_7$ is H, $R_2$ is H or F and $R_3$ is H or F. In still a further example, $R_1$ is H, $R_6$ is H, $R_7$ is F, $R_2$ is H or F and $R_3$ is H or F. For these examples, $R_4$ and $R_5$ may have the values described herein.

There is also provided a compound of Formula I, or an isotope labelled analog thereof, or a pharmaceutically acceptable salt thereof, which is at least one of the following:
3-(2,3,5-trifluorophenoxy)azetidine,
3-(2,3,5,6-tetrafluorophenoxy)-azetidine,
3-methyl-3-(2,3,5-trifluoro-phenoxy)azetidine,
3-(2,3-difluorophenoxy)-1-methylazetidine,
3-(2,3-difluorophenoxy)-1-methylazetidine,
3-(2,3-difluorophenoxy)-1-ethylazetidine,
3-(2,3-difluorophenoxy)-3-methylazetidine,
3-(2,3-difluorophenoxy)-1,3-dimethylazetidine,
3-(2,3-difluorophenoxy)-1-ethyl-3-methylazetidine,
1-methyl-3-(2,3,4-trifluoro-phenoxy)azetidine,
1-ethyl-3-(2,3,4-trifluoro-phenoxy)azetidine,
3-methyl-3-(2,3,4-trifluoro-phenoxy)azetidine,
1,3-dimethyl-3-(2,3,4-trifluorophenoxy)azetidine,
1-ethyl-3-methyl-3-(2,3,4-trifluorophenoxy)azetidine,
1-methyl-3-(2,3,5-trifluoro-phenoxy)azetidine,
1-ethyl-3-(2,3,5-trifluoro-phenoxy)azetidine,
1,3-dimethyl-3-(2,3,5-trifluorophenoxy)azetidine,
1-ethyl-3-methyl-3-(2,3,5-trifluorophenoxy)azetidine,
3-(2,3,6-trifluorophenoxy)azetidine,
1-methyl-3-(2,3,6-trifluoro-phenoxy)azetidine,
1-ethyl-3-(2,3,6-trifluoro-phenoxy)azetidine,
3-methyl-3-(2,3,6-trifluoro-phenoxy)azetidine,
1,3-dimethyl-3-(2,3,6-trifluoro-phenoxy)azetidine,
1-ethyl-3-methyl-3-(2,3,6-trifluorophenoxy)azetidine,
3-(2,3,4,5-tetrafluoro-phenoxy)azetidine,
1-methyl-3-(2,3,4,5-tetrafluoro-phenoxy)azetidine,
1-ethyl-3-(2,3,4,5-tetrafluoro-phenoxy)azetidine,
3-methyl-3-(2,3,4,5-tetrafluorophenoxy)azetidine,
1,3-dimethyl-3-(2,3,4,5-tetrafluorophenoxy)azetidine,
1-ethyl-3-methyl-3-(2,3,4,5-tetrafluorophenoxy)azetidine,
3-(2,3,4,6-tetrafluorophenoxy)-azetidine,
1-methyl-3-(2,3,4,6-tetrafluoro-phenoxy)azetidine,
1-ethyl-3-(2,3,4,6-tetrafluoro-phenoxy)azetidine,
3-methyl-3-(2,3,4,6-tetrafluorophenoxy)azetidine,
1,3-dimethyl-3-(2,3,4,6-tetrafluorophenoxy)azetidine, 1-ethyl-3-methyl-3-(2,3,4,6-tetrafluorophenoxy)azetidine,
1-methyl-3-(2,3,5,6-tetrafluorophenoxy)azetidine,
1-ethyl-3-(2,3,5,6-tetrafluorophenoxy)azetidine,
3-methyl-3-(2,3,5,6-tetrafluorophenoxy)azetidine,
1,3-dimethyl-3-(2,3,5,6-tetrafluorophenoxy)azetidine,
1-ethyl-3-methyl-3-(2,3,5,6-tetrafluorophenoxy)azetidine,
1-methyl-3-(2,3,4,5,6-pentafluorophenoxy)azetidine,
1-ethyl-3-(2,3,4,5,6-pentafluorophenoxy)azetidine,
3-methyl-3-(2,3,4,5,6-pentafluorophenoxy)azetidine,
1,3-dimethyl-3-(2,3,4,5,6-pentafluorophenoxy)azetidine,
1-ethyl-3-methyl-3-(2,3,4,5,6-pentafluorophenoxy)azetidine,
3-(3,4,5-trifluorophenoxy)azetidine,
3-(2,4,6-trifluorophenoxy)-1-ethylazetidine,
3-(2,3,6-trifluorophenoxy)-1-propylazetidine,
3-(3,5-difluorophenoxy)-1-methylazetidine,
3-(3,5-difluorophenoxy)-1-ethylazetidine,
3-(3,5-difluorophenoxy)-3-methylazetidine,
3-(3,5-difluorophenoxy)-1,3-dimethylazetidine,
3-(3,5-difluorophenoxy)-1-ethyl-3-methylazetidine,
3-(2,3-difluorophenoxy)-1-($^2H_3$)methylazetidine,
3-(2,3-difluorophenoxy)-1-[(1,1,2,2,2-$^2H_5$)ethyl]azetidine,
3-(2,3-difluorophenoxy)(3-$^2H$)azetidine,
3-(2,3-difluorophenoxy)(2,2,4,4-$^2H_4$)azetidine,
3-(2,3-difluorophenoxy)(2,2,3,4,4-$^2H_5$)azetidine,
3-[2,3-difluoro(4,6-$^2H_2$)phenoxy]azetidine,
3-[2,3-difluoro(4,6-$^2H_2$)phenoxy](3-$^2H$)azetidine,
3-[2,3-difluoro(4,6-$^2H_2$)phenoxy](2,2,4,4-$^2H_4$)azetidine,
3-[2,3-difluoro(4,6-$^2H_2$)phenoxy](2,2,3,4,4-$^2H_5$)azetidine,
3-(3,5-difluorophenoxy)-1-($^2H_3$)methylazetidine,
3-(3,5-difluorophenoxy)-1-[(1,1,2,2,2-$^2H_5$)ethyl]azetidine,
3-(3,5-difluorophenoxy)(3-$^2H$)azetidine;
3-(3,5-difluorophenoxy)(2,2,4,4-$^2H_4$)azetidine,
3-(3,5-difluorophenoxy)(2,2,3,4,4-$^2H_5$)azetidine,
3-[3,5-difluoro(2,4,6-$^2H_3$)phenoxy]azetidine,
3-[3,5-difluoro(2,4,6-$^2H_3$)phenoxy](3-$^2H$)azetidine,
3-[3,5-difluoro(2,4,6-$^2H_3$)phenoxy](2,2,4,4-$^2H_4$)azetidine,
3-[3,5-difluoro(2,4,6-$^2H_3$)phenoxy](2,2,3,4,4-$^2H_5$)azetidine,
1-($^2H_3$)methyl-3-(2,3,5,6-tetrafluorophenoxy)azetidine,
1-[(1,1,2,2,2-$^2H_5$)ethyl]-3-(2,3,5,6-tetrafluorophenoxy)azetidine,
3-(2,3,5,6-tetrafluorophenoxy)(3-$^2H$)azetidine,
3-(2,3,5,6-tetrafluorophenoxy)(2,2,4,4-$^2H_4$)azetidine,
3-(2,3,5,6-tetrafluorophenoxy)(2,2,3,4,4-$^2H_5$)azetidine,
3-[2,3,5,6-tetrafluoro(4-2H)phenoxy]azetidine,
3-[2,3,5,6-tetrafluoro(4-$^2H$)phenoxy](3-$^2H$)azetidine,
3-[2,3,5,6-tetrafluoro(4-$^2H$)phenoxy](2,2,4,4-$^2H_4$)azetidine,
3-[2,3,5,6-tetrafluoro(4-$^2H$)phenoxy](2,2,3,4,4-$^2H_5$)azetidine,
1-($^2H_3$)methyl-3-(2,3,6-trifluorophenoxy)azetidine,
1-[(1,1,2,2,2-$^2H_5$)ethyl]-3-(2,3,6-trifluorophenoxy)azetidine,
3-(2,3,6-trifluorophenoxy)(3-$^2H$)azetidine,
3-(2,3,6-trifluorophenoxy)(2,2,4,4-$^2H_4$)azetidine,
3-(2,3,6-trifluorophenoxy)(2,2,3,4,4-$^2H_5$)azetidine,
3-[2,3,6-trifluoro(4-$^2H$)phenoxy]azetidine,
3-[2,3,6-trifluoro(4-$^2H$)phenoxy](3-$^2H$)azetidine,
3-[2,3,6-trifluoro(4-$^2H$)phenoxy](2,2,4,4-$^2H_4$)azetidine,
3-[2,3,6-trifluoro(4-$^2H$)phenoxy](2,2,3,4,4-$^2H_5$)azetidine,
1-($^2H_3$)methyl-3-(2,3,5-trifluorophenoxy)azetidine,
1-[(1,1,2,2,2-$^2H_5$)ethyl]-3-(2,3,5-trifluorophenoxy)azetidine,
3-(2,3,5-trifluorophenoxy)(3-$^2H$)azetidine,
3-(2,3,5-trifluorophenoxy)(2,2,4,4-$^2H_4$)azetidine,
3-(2,3,5-trifluorophenoxy)(2,2,3,4,4-$^2H_5$)azetidine,
3-[2,3,5-trifluoro(4-$^2H$)phenoxy]azetidine,
3-[2,3,5-trifluoro(4-$^2H$)phenoxy](3-$^2H$)azetidine,
3-[2,3,5-trifluoro(4-$^2H$)phenoxy](2,2,4,4-$^2H_4$)azetidine,
3-[2,3,5-trifluoro(4-$^2H$)phenoxy](2,2,3,4,4-$^2H_5$)azetidine.

There is also provided a compound of Formula I, or an isotope labelled analog thereof, or a pharmaceutically acceptable salt thereof, which is at least one of the following:
3-(2,3,5-trifluorophenoxy)azetidine,
3-(2,3,5,6-tetrafluorophenoxy)-azetidine,
3-methyl-3-(2,3,5-trifluoro-phenoxy)azetidine,
3-(2,3-difluorophenoxy)-1-methylazetidine,
3-(2,3,6-trifluorophenoxy)azetidine,
1-ethyl-3-(2,3,6-trifluoro-phenoxy)azetidine,
1-methyl-3-(2,3,5,6-tetrafluorophenoxy)azetidine,
1-ethyl-3-(2,3,5,6-tetrafluorophenoxy)azetidine,
3-(3,4,5-trifluorophenoxy)azetidine,
3-(2,4,6-trifluorophenoxy)-1-ethylazetidine,
3-(2,3,6-trifluorophenoxy)-1-propylazetidine,
3-(3,5-difluorophenoxy)-1-methylazetidine,
3-(2,3-difluorophenoxy)-1-($^2H_3$)methylazetidine,
3-(3,5-difluorophenoxy)-1-($^2H_3$)methylazetidine,
3-[3,5-difluoro(2,4,6-$^2H_3$)phenoxy]azetidine oxalic acid salt,
1-[(1,1,2,2,2-$^2H_3$)ethyl]-3-(2,3,6-trifluorophenoxy)azetidine.

There is also provided a compound of Formula I,

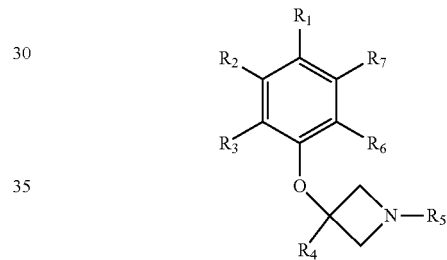

Formula I which is an isotope labelled analog of or a pharmaceutically acceptable salt of at least one of the following compounds:
3-(2,3-difluorophenoxy)azetidine,
3-(2,3,5-trifluorophenoxy)azetidine,
3-(2,3,5,6-tetrafluorophenoxy)-azetidine,
3-(2,3,6-trifluorophenoxy)azetidine,
3-(2,4,6-Trifluorophenoxy)azetidine,
3-(3,4,5-Trifluorophenoxy)azetidine,
3-(2,4,5-Trifluorophenoxy)azetidine,
3-(3,5-difluorophenoxy)azetidine,
with the proviso that the compound of Formula I is not 3-(3,5-difluorophenoxy)azetidine hydrochloric acid salt.

In an example, the compound of Formula I is an isotope labelled analog of or a pharmaceutically acceptable salt of 3-(2,3-difluorophenoxy)azetidine. The pharmaceutically acceptable salt may be a HCl salt. Alternatively, the pharmaceutically acceptable salt be a salt other than a HCl salt, i.e. the pharmaceutically acceptable salt does not include a HCl salt.

In a further example, there is provided an isotope labelled analog of or a pharmaceutically acceptable salt of 3-(3,5-difluorophenoxy)azetidine
with the proviso that the compound of Formula I is not 3-(3,5-difluorophenoxy)azetidine hydrochloric acid salt.

In still a further example, the compound of Formula I as described herein may be an isotope labelled analog of or a pharmaceutically acceptable salt of at least one of the following compounds:

3-(2,3,5,6-tetrafluorophenoxy)-azetidine,
3-(2,3,6-trifluorophenoxy)azetidine,
3-(3,4,5-Trifluorophenoxy)azetidine.

In still a further example, there is provided 3-(2,3,5,6-tetrafluorophenoxy)-azetidine, or an isotope labelled analog thereof or a pharmaceutically acceptable salt thereof.

The present disclosure also provides a compound of Formula I as described herein which is a pharmaceutically acceptable salt of a isotope labelled analog of said compound of Formula I. The isotope labelled analog may be a deuterated analog.

There is also provided a compound of Formula I as described herein, or an isotope labelled analog thereof, or a pharmaceutically acceptable salt thereof, for use as a medicament in therapy. For instance, the compound of Formula I may be at least one of the following:
3-(2,3,5-trifluorophenoxy)azetidine,
3-(2,3,5,6-tetrafluorophenoxy)-azetidine,
3-methyl-3-(2,3,5-trifluoro-phenoxy)azetidine,
3-(2,3-difluorophenoxy)-1-methylazetidine,
3-(2,3-difluorophenoxy)-1-ethylazetidine,
3-(2,3-difluorophenoxy)-3-methylazetidine,
3-(2,3-difluorophenoxy)-1,3-dimethylazetidine,
3-(2,3-difluorophenoxy)-1-ethyl-3-methylazetidine,
1-methyl-3-(2,3,4-trifluoro-phenoxy)azetidine,
1-ethyl-3-(2,3,4-trifluoro-phenoxy)azetidine,
3-methyl-3-(2,3,4-trifluoro-phenoxy)azetidine,
1,3-dimethyl-3-(2,3,4-trifluorophenoxy)azetidine,
1-ethyl-3-methyl-3-(2,3,4-trifluorophenoxy)azetidine,
1-methyl-3-(2,3,5-trifluoro-phenoxy)azetidine,
1-ethyl-3-(2,3,5-trifluoro-phenoxy)azetidine,
1,3-dimethyl-3-(2,3,5-trifluorophenoxy)azetidine,
1-ethyl-3-methyl-3-(2,3,5-trifluorophenoxy)azetidine,
3-(2,3,6-trifluorophenoxy)azetidine,
1-methyl-3-(2,3,6-trifluoro-phenoxy)azetidine,
1-ethyl-3-(2,3,6-trifluoro-phenoxy)azetidine,
3-methyl-3-(2,3,6-trifluoro-phenoxy)azetidine,
1,3-dimethyl-3-(2,3,6-trifluoro-phenoxy)azetidine,
1-ethyl-3-methyl-3-(2,3,6-trifluorophenoxy)azetidine,
3-(2,3,4,5-tetrafluoro-phenoxy)azetidine,
1-methyl-3-(2,3,4,5-tetrafluoro-phenoxy)azetidine,
1-ethyl-3-(2,3,4,5-tetrafluoro-phenoxy)azetidine,
3-methyl-3-(2,3,4,5-tetrafluorophenoxy)azetidine,
1,3-dimethyl-3-(2,3,4,5-tetrafluorophenoxy)azetidine,
1-ethyl-3-methyl-3-(2,3,4,5-tetrafluorophenoxy)azetidine,
3-(2,3,4,6-tetrafluorophenoxy)-azetidine,
1-methyl-3-(2,3,4,6-tetrafluorophenoxy)azetidine,
1-ethyl-3-(2,3,4,6-tetrafluoro-phenoxy)azetidine,
3-methyl-3-(2,3,4,6-tetrafluorophenoxy)azetidine,
1,3-dimethyl-3-(2,3,4,6-tetrafluorophenoxy)azetidine,
1-ethyl-3-methyl-3-(2,3,4,6-tetrafluorophenoxy)azetidine,
1-methyl-3-(2,3,5,6-tetrafluorophenoxy)azetidine,
1-ethyl-3-(2,3,5,6-tetrafluorophenoxy)azetidine,
3-methyl-3-(2,3,5,6-tetrafluorophenoxy)azetidine,
1,3-dimethyl-3-(2,3,5,6-tetrafluorophenoxy)azetidine,
1-ethyl-3-methyl-3-(2,3,5,6-tetrafluorophenoxy)azetidine,
1-methyl-3-(2,3,4,5,6-pentafluorophenoxy)azetidine,
1-ethyl-3-(2,3,4,5,6-pentafluorophenoxy)azetidine,
3-methyl-3-(2,3,4,5,6-pentafluorophenoxy)azetidine,
1,3-dimethyl-3-(2,3,4,5,6-pentafluorophenoxy)azetidine,
1-ethyl-3-methyl-3-(2,3,4,5,6-pentafluorophenoxy)azetidine,
3-(3,4,5-trifluorophenoxy)azetidine,
3-(2,4,6-trifluorophenoxy)-1-ethylazetidine,
3-(2,4,6-trifluorophenoxy)-1-propylazetidine,
3-(3,5-difluorophenoxy)-1-methylazetidine,
3-(3,5-difluorophenoxy)-1-ethylazetidine,
3-(3,5-difluorophenoxy)-3-methylazetidine,
3-(3,5-difluorophenoxy)-1,3-dimethylazetidine,
3-(3,5-difluorophenoxy)-1-ethyl-3-methylazetidine,
3-(2,3-difluorophenoxy)-1-($^2H_3$)methylazetidine,
3-(2,3-difluorophenoxy)-1-[(1,1,2,2,2-$^2H_5$)ethyl]azetidine,
3-(2,3-difluorophenoxy)(3-$^2H$)azetidine,
3-(2,3-difluorophenoxy)(2,2,4,4-$^2H_4$)azetidine,
3-(2,3-difluorophenoxy)(2,2,3,4,4-$^2H_5$)azetidine,
3-[2,3-difluoro(4,6-$^2H_2$)phenoxy]azetidine,
3-[2,3-difluoro(4,6-$^2H_2$)phenoxy](3-$^2H$)azetidine,
3-[2,3-difluoro(4,6-$^2H_2$)phenoxy](2,2,4,4-$^2H_4$)azetidine,
3-[2,3-difluoro(4,6-$^2H_2$)phenoxy](2,2,3,4,4-$^2H_5$)azetidine,
3-(3,5-difluorophenoxy)-1-($^2H_3$)methylazetidine,
3-(3,5-difluorophenoxy)-1-[(1,1,2,2,2-$^2H_5$)ethyl]azetidine,
3-(3,5-difluorophenoxy)(3-$^2H$)azetidine;
3-(3,5-difluorophenoxy)(2,2,4,4-$^2H_4$)azetidine,
3-(3,5-difluorophenoxy)(2,2,3,4,4-$^2H_5$)azetidine,
3-[3,5-difluoro(2,4,6-$^2H_3$)phenoxy]azetidine,
3-[3,5-difluoro(2,4,6-$^2H_3$)phenoxy](3-$^2H$)azetidine,
3-[3,5-difluoro(2,4,6-$^2H_3$)phenoxy](2,2,4,4-$^2H_4$)azetidine,
3-[3,5-difluoro(2,4,6-$^2H_3$)phenoxy](2,2,3,4,4-$^2H_5$)azetidine,
1-($^2H_3$)methyl-3-(2,3,5,6-tetrafluorophenoxy)azetidine,
1-[(1,1,2,2,2-$^2H_5$)ethyl]-3-(2,3,5,6-tetrafluorophenoxy)azetidine,
3-(2,3,5,6-tetrafluorophenoxy)(3-$^2H$)azetidine,
3-(2,3,5,6-tetrafluorophenoxy)(2,2,4,4-$^2H_4$)azetidine,
3-(2,3,5,6-tetrafluorophenoxy)(2,2,3,4,4-$^2H_5$)azetidine,
3-[2,3,5,6-tetrafluoro(4-$^2H$)phenoxy]azetidine,
3-[2,3,5,6-tetrafluoro(4-$^2H$)phenoxy](3-$^2H$)azetidine,
3-[2,3,5,6-tetrafluoro(4-$^2H$)phenoxy](2,2,4,4-$^2H_4$)azetidine,
3-[2,3,5,6-tetrafluoro(4-$^2H$)phenoxy](2,2,3,4,4-$^2H_5$)azetidine,
1-($^2H_3$)methyl-3-(2,3,6-trifluorophenoxy)azetidine,
1-[(1,1,2,2,2-$^2H_5$)ethyl]-3-(2,3,6-trifluorophenoxy)azetidine,
3-(2,3,6-trifluorophenoxy)(3-$^2H$)azetidine,
3-(2,3,6-trifluorophenoxy)(2,2,4,4-$^2H_4$)azetidine,
3-(2,3,6-trifluorophenoxy)(2,2,3,4,4-$^2H_5$)azetidine,
3-[2,3,6-trifluoro(4-$^2H$)phenoxy]azetidine,
3-[2,3,6-trifluoro(4-$^2H$)phenoxy](3-$^2H$)azetidine,
3-[2,3,6-trifluoro(4-$^2H$)phenoxy](2,2,4,4-$^2H_4$)azetidine,
3-[2,3,6-trifluoro(4-$^2H$)phenoxy](2,2,3,4,4-$^2H_5$)azetidine,
1-($2H_3$)methyl-3-(2,3,5-trifluorophenoxy)azetidine,
1-[(1,1,2,2,2-$^2H_5$)ethyl]-3-(2,3,5-trifluorophenoxy)azetidine,
3-(2,3,5-trifluorophenoxy)(3-$^2H$)azetidine,
3-(2,3,5-trifluorophenoxy)(2,2,4,4-$^2H_4$)azetidine,
3-(2,3,5-trifluorophenoxy)(2,2,3,4,4-$^2H_5$)azetidine,
3-[2,3,5-trifluoro(4-$^2H$)phenoxy]azetidine,
3-[2,3,5-trifluoro(4-$^2H$)phenoxy](3-$^2H$)azetidine,
3-[2,3,5-trifluoro(4-$^2H$)phenoxy](2,2,4,4-$^2H_4$)azetidine,
3-[2,3,5-trifluoro(4-$^2H$)phenoxy](2,2,3,4,4-$^2H_5$)azetidine,
or an isotope labelled analog thereof, or a pharmaceutically acceptable salt thereof. In a further
example, the compound of Formula I may be at least one of the following:
3-(2,3,5-trifluorophenoxy)azetidine,
3-(2,3,5,6-tetrafluorophenoxy)-azetidine,
3-methyl-3-(2,3,5-trifluoro-phenoxy)azetidine,
3-(2,3-difluorophenoxy)-1-methylazetidine,
3-(2,3,6-trifluorophenoxy)azetidine,
1-ethyl-3-(2,3,6-trifluoro-phenoxy)azetidine,
1-methyl-3-(2,3,5,6-tetrafluorophenoxy)azetidine,
1-ethyl-3-(2,3,5,6-tetrafluorophenoxy)azetidine,
3-(3,4,5-trifluorophenoxy)azetidine,
3-(2,3,6-trifluorophenoxy)azetidine, 3-(2,4,6-trifluorophenoxy)-1-ethylazetidine,
3-(2,3,6-trifluorophenoxy)-1-propylazetidine,
3-(3,5-difluorophenoxy)-1-methylazetidine,
3-(2,3-difluorophenoxy)-1-($^2$H$_3$)methylazetidine,
3-(3,5-difluorophenoxy)-1-($^2$H$_3$)methylazetidine,
3-[3,5-difluoro(2,4,6-$^2$H$_3$)phenoxy]azetidine oxalic acid salt,
1-[(1,1,2,2,2-$^2$H$_5$)ethyl]-3-(2,3,6-trifluorophenoxy)azetidine,
or an isotope labelled analog thereof, or a pharmaceutically acceptable salt thereof.

The present disclosure provides a compound of Formula I as described herein, or an isotope labelled analog thereof, or a pharmaceutically acceptable salt thereof, for use in the treatment and/or prevention of a disease, disorder and/or condition which is responsive to modulation of monoamines in the cerebral cortex.

The compounds disclosed herein may be in the form of a pharmaceutically acceptable salt. Thus, there is provided a pharmaceutically acceptable salt of compound of Formula I as described herein.

In an example, there is provided at least one of the following:
a pharmaceutically acceptable salt of 3-(2,3-difluorophenoxy)azetidine,
a pharmaceutically acceptable salt of 3-(2,3,4-trifluorophenoxy)azetidine,
a pharmaceutically acceptable salt of 3-(2,3,4,5,6-pentafluorophenoxy)azetidine,
a pharmaceutically acceptable salt of 3-(2,5-difluorophenoxy)azetidine,
a pharmaceutically acceptable salt of 3-(2,4,6-trifluorophenoxy)azetidine,
a pharmaceutically acceptable salt of 3-(2,4,5-trifluorophenoxy)azetidine.

The pharmaceutically acceptable salt may include a HCl salt. Alternatively, the pharmaceutically acceptable salt may be a salt which is not a HCl salt.

In a further example, there is provided at least one of the following at least one of the following:
a pharmaceutically acceptable salt of 3-(2,4-difluorophenoxy)azetidine,
a pharmaceutically acceptable salt of 3-(2,6-difluorophenoxy)azetidine,
a pharmaceutically acceptable salt of 3-(3,4-difluorophenoxy)azetidine,
a pharmaceutically acceptable salt of 3-(3,5-difluorophenoxy)azetidine,
with the proviso that the pharmaceutically acceptable salt is not a HCl salt.

In a further example, the pharmaceutically acceptable salt may be a hydrochloric acid salt.

Accordingly, there is provided a compound of Formula I which is selected from the group consisting of:
3-(2,3-difluorophenoxy)azetidine hydrochloride,
3-(2,3,5-trifluorophenoxy)azetidine hydrochloride,
3-(2,3,5,6-tetrafluorophenoxy)-azetidine,
3-(2,3,6-trifluorophenoxy)azetidine hydrochloric acid salt,
3-methyl-3-(2,3,5-trifluorophenoxy)azetidine hydrochloride,
1-methyl-3-(2,3,5,6-tetrafluorophenoxy)azetidine hydrochloric acid salt,
1-ethyl-3-(2,3,5,6-tetrafluorophenoxy)azetidine hydrochloric acid salt,
3-(2,3,4,5,6-pentafluoro-phenoxy)azetidine hydrochloric acid salt,
3-(2,4,6-trifluorophenoxy)azetidine hydrochloric acid salt,
3-(3,4,5-trifluorophenoxy)azetidine hydrochloric acid salt, and
3-(2,4,5-trifluorophenoxy)azetidine hydrochloric acid salt.

It shall be understood that as used herein all references to compounds of the present disclosure are intended to include all possible pharmaceutically acceptable salts, co-crystals, solvates, hydrates, polymorphs, and stereoisomers thereof.

In addition, compounds as described herein may be administered in the form of a prodrug. A prodrug is a compound which may have little or no pharmacological activity itself, but when such compound is administered into or onto the body of a patient, it is converted into a compound of Formula I having the desired activity. Various prodrugs are known within the art (e.g. Rautio et al., Nat Rev Drug Discov, 2008, 7(3); 255-70).

Also included within the scope of the present disclosure are metabolites of compounds as described herein that is compounds formed in vivo upon administration of compounds of Formula I as described herein.

It is believed that compounds of the present disclosure possess satisfactory pharmacological profile and promising biopharmaceutical properties, such as toxicological profile, metabolism and pharmacokinetic properties, solubility and permeability, in particular for providing a satisfactory bioavailability upon oral administration thereof.

Compounds of the present disclosure may have advantageous properties compared to compounds of prior art, such as enhanced potency and/or enhanced selectivity. Such advantages may provide for corresponding useful properties in practice. For example, when used as a medicament, compounds of the present disclosure may have a lower daily clinical dose, longer duration of action and/or an improved side effect profile compared to compounds of prior art.

Pharmaceutically Acceptable Salts

Compounds of the present disclosure may be provided in any form suitable for the intended administration. Suitable forms include pharmaceutically (i.e. physiologically) acceptable salts of a compound as disclosed herein (Paulekuhn G S et al., J Med Chem, 2007, 50; 6665-72 and Berge S M et al., J Pharm Sci, 1977, 66; 1-19). As used herein "pharmaceutically acceptable salt", where such salts are possible, includes salts prepared from pharmaceutically acceptable non-toxic acids, i.e. pharmaceutically acceptable acid addition salts.

Examples of pharmaceutically acceptable salts include, without limitation, non-toxic inorganic and organic acid addition salts such as hydrochloride, hydrobromide, borate, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, propionate, salicylate, sorbate, stearate, succinate, tartrate, toluene-p-sulphonate, and the like. Hemisalts of acids may also be formed, for example, hemisulphate. Such salts may be formed by procedures well known and described in the art. In a further example, the pharmaceutically acceptable salts do not include hydrochloride salts, i.e. do not include salts of hydrochloric acid.

Other acids such as oxalic acid, which may not be considered pharmaceutically acceptable, may be useful in the preparation of salts useful as intermediates in obtaining a compound of the present disclosure and its pharmaceutically acceptable acid addition salt.

Co-Crystals

In a salt, proton transfer may occur between the active pharmaceutical ingredient and the counter ion of the salt.

However, in some cases there is no or only partial proton transfer and the solid is therefore not a true salt. It is accepted that the proton transfer is in fact a continuum, and can change with temperature, and therefore the point at which a salt is better described as a "co-crystal" may be subjective. The term "co-crystal" as used herein refers to multicomponent system in which there exists a host molecule or molecules (active pharmaceutical ingredient) and a guest (or co-former) molecule or molecules. The guest or co-former molecule is defined as existing as a solid at room temperature in order to distinguish the co-crystal from solvates. However, a co-crystal may itself form solvates. In a co-crystal there is generally predominance for interaction through non-ionic forces, such as hydrogen bonding.

Solvates

It is also to be understood that certain compounds of the present disclosure may exist in solvated forms, including solvates of the free compounds or solvates of a salt of the compound, as well as in unsolvated forms. The term "solvate" is used herein to describe a molecular complex comprising the compound of the present disclosure and one or more pharmaceutically acceptable solvent molecules, for example, ethanol. The term "hydrate" is employed when said solvent is water. Thus, solvated forms may include hydrated forms such as monohydrate, dihydrate, hemihydrate, trihydrate, tetrahydrate, and the like.

Polymorphs

Compounds of the present disclosure may exist in a continuum of solid states ranging from fully amorphous to fully crystalline. Thus, it is to be understood that all polymorphs, such as mixtures of different polymorphs, are included within the scope of the claimed compounds.

Labelled Compounds

Compounds of the present disclosure may be used in their labelled or unlabelled form. In the context of this present disclosure the labelled compound has one or more atoms replaced by an atom having an atomic mass or mass number different from the atomic mass or mass number usually found in nature. The labelling will allow easy quantitative detection of said compound.

Labelled compounds of the present disclosure may be useful as diagnostic tools, radio tracers, or monitoring agents in various diagnostic methods, and for in vivo receptor imaging.

Labelled compounds of the present disclosure may contain at least one radio-nuclide as a label. Positron emitting radionuclides are all candidates for usage. In the context of this present disclosure the radionuclide may be selected from isotopes of hydrogen, carbon, nitrogen, fluorine and oxygen, such as $^2H$ (deuterium), $^3H$ (tritium), $^{11}C$, $^{13}C$, $^{14}C$, $^{18}O$, $^{17}O$, $^{19}F$ and $^{18}F$. It is known that substitution with heavier isotopes, such as substitution of one or more hydrogen atoms with deuterium ($^2H$) might provide pharmacological advantages in some instances, such as increased metabolic stability.

The physical method for detecting a labelled compound of the present disclosure may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

Compounds of the present disclosure may be prepared by conventional methods for chemical synthesis, e.g. those described in the examples section. The starting materials for the processes described in the present application are known or may readily be prepared by conventional methods from commercially available chemicals.

Also, one compound of the present disclosure can be converted to another compound of the present disclosure using conventional methods such as for instance converting a compound of the present disclosure to its N-alkylated derivative utilizing alkylation techniques that are well known in the art.

The end products of the reactions described herein may be isolated by conventional techniques, e.g. by extraction, crystallization, distillation, chromatography, or the like.

Persons skilled in the art will appreciate that, in order to obtain compounds of the present disclosure in an alternative—and in some occasions, more convenient manner—the individual process steps mentioned hereinbefore may be performed in a different order, and/or the individual reactions may be performed at different stage in the overall route (i.e. chemical transformations may be performed upon different intermediates to those associated hereinbefore with a particular reaction).

Description of Animal Models Used

The change in turnover of dopamine in the terminal areas of the ascending dopaminergic projections of the mammalian brain can be illustrated by measuring of changes in biochemical indices in the brain e.g. changes in concentrations of dopamine metabolites such as 3,4-dihydroxyphenylacetic acid (DOPAC) in the striatum and frontal cortex.

The measurement of the tissue content of DOPAC is well established in the field of research since the 1960's. In short, male Sprague-Dawley rats are administered the test compound 60 minutes prior to decapitation. The brain is rapidly taken out and dissected. The striatum is rapidly frozen and subsequently quantitatively analyzed with respect to its content of DOPAC by means of HPLC and electrochemical detection. The number of animals used for each test compound/vehicle is 5/group.

The microdialysis technique is a well-established technique for measuring extracellular levels of neurotransmitters (Ungerstedt, J Int Med, 1991, 230; 365-73). The microdialysis technique was used to measure the effect of compounds disclosed herein upon the efflux of monoamine transmitters (NA, DA and 5-HT) in striatum and frontal cortex in conscious, freely moving rats.

Sesack et al. (Anatom Substr Glut-Dopamine Inter. Annals of NY AcadSci, 2003, 1003; 36-52) discloses that the dopaminergic systems of the brain interact strongly with central glutamate neurotransmission. To investigate potential effects of compounds as disclosed herein on cortical and striatal NMDA type glutamate receptor related synaptic signaling, Arc mRNA induction was assessed upon acute administration. Arc (Arc/Arg3.1-activity regulated cytoskeleton-associated protein/activity-regulated gene 3.1; (Link W et al., Proc Natl Acad Sci, USA, 1995, 92; 5734-8 and Lyford G L et al., Neuron, 1995, 14; 433-45), is an immediate early gene (IEG), induced by synaptic activity, whose expression and localization at synaptic sites is triggered specifically by NMDA receptor activation and strongly related to neural plasticity (Steward and Worley, Neuron, 2001, 30; 227-40, Kawashima et al., PNAS, 2009, 106(1); 316-21 and Bramham et al., Exp Brain Res, 2010, 200; 125-40).

The effect of compounds in the present disclosure on locomotor activity in drug-naïve rats was also investigated. The animals were placed in the motility meters immediately after drug administration and locomotor activity was recorded for 60 minutes (counts/60 min±SEM). The results are presented as percent of control.

Biological Activity

A serotonin-norepinephrine-dopamine reuptake inhibitor (SNDRI), also known as a triple reuptake inhibitor (TRI), is a type of drug that acts as a combined reuptake inhibitor of the monoamine neurotransmitters serotonin, norepinephrine, and dopamine. It does this by concomitantly inhibiting the serotonin transporter (SERT), norepinephrine transporter (NET), and dopamine transporter (DAT), respectively. Inhibition of the reuptake of these neurotransmitters increases their extracellular concentrations and, therefore, results in an increase in serotonergic, adrenergic, and dopaminergic neurotransmission across the brain. However, the use of triple re-uptake inhibitors (especially the inhibition of DAT) in humans are of potential concern due to abuse liability. Cocaine is the most well-known triple-uptake inhibitor and is widely encountered as a drug of abuse. Compounds of the present disclosure have surprisingly been found to not bind with high affinity to human serotonin (5-HT), norepinephrine and dopamine transporters (i.e. do not inhibit the monoamine neurotransmitter up-take). In this document, a high affinity to SERT, NET and/or DAT is understood to mean that the affinity is equal to or higher than about 75% such as about 80% or about 90% using the assays described herein, wherein the concentration of each tested compound in such assay is 10 µM. One assay to measure affinity of said compounds as described herein may be the percent inhibition from radioligand binding assay using cells expressing human transporters and receptors (Table 5), wherein the concentration of each tested compound in such assay is 10 µM. Alternatively other assays known to the skilled person may be used to measure the affinity of said compounds, wherein the concentration of each tested compound in such assay is 10 µM. Thus, the compounds of the present disclosure bind with an affinity less than about 75% to SERT, NET and/or DAT, when tested according to an assay as disclosed herein and the concentration of each tested compound in such assay is 10 µM. Further the compounds of the present disclosure bind with an affinity less than about 60% to SERT, NET and/or DAT, when tested according to the assay as disclosed herein and the concentration of each tested compound in such assay is 10 µM. Some compounds of the present disclosure bind with an affinity less than about 50% to SERT, NET and/or DAT, when tested according to the assay as disclosed herein and the concentration of each tested compound in such assay is 10 µM. Some compounds of the present disclosure bind with an affinity less than about 30%, about 25% or about 20% to SERT, NET and/or DAT, when tested according to the assay as disclosed herein and the concentration of each tested compound in such assay is 10 µM. Some compounds of the present disclosure bind with an affinity less than about 15%, about 10% or about 5% to SERT, NET and/or DAT, when tested according to an assay as disclosed herein and the concentration of each tested compound in such assay is 10 µM. Some compounds of the present disclosure bind with an affinity less than about 5% or less than about 0% to SERT, NET and/or DAT, when tested according to the assay as disclosed herein and the concentration of each tested compound in such assay is 10 µM.

Locomotor activity can be tested by means of monitoring behavioural activity as described herein or by means corresponding to the assay described herein, wherein behavioural activity is monitored before and after treatment with any compound to be evaluated. Some compounds as disclosed herein have surprisingly been found to not increase locomotor activity in a dose dependent manner when compared to a control group treated with saline solution. Some compounds as disclosed herein have surprisingly been found to not increase locomotor activity in a dose dependent manner when compared to a control group treated with saline solution or to reference compounds known in the art. Some compounds as disclosed herein have surprisingly been shown to reduce the locomotor activity in a dose dependent manner relative to control means (i.e. saline solution). Some compounds as disclosed herein have surprisingly been shown to reduce the locomotor activity in a dose dependent manner relative to control means (i.e. saline solution) and also relative to reference compounds known in the art. Some compounds as disclosed herein decrease locomotor activity to about 60-70% of the locomotor activity of saline treated controls. Some compounds as disclosed herein decrease locomotor activity to about 60-70% or less of the locomotor activity of saline treated controls. Some compounds as disclosed herein decrease locomotor activity to about 20-25% or less of the locomotor activity of saline treated controls. Some of the compounds have a low affinity to DAT and show a significant reduced locomotor activity.

Further, compounds as disclosed herein possess modulating effects on monoamines in cerebral cortex and both they and their pharmaceutical compositions are useful in treating numerous central nervous system disorders such as psychiatric disorders. Particularly, compounds as disclosed herein and their pharmaceutical compositions are useful in the treatment of CNS disorders where the cortical monoaminergic systems are dysfunctional due to direct or indirect causes. Compounds according to the present disclosure can be used to treat affective disorders and cognitive disorders such as neurodegenerative and neurodevelopmental disorders and/or diseases. Also, compounds with modulating effects on dopaminergic systems may be used to improve motor functions in patients suffering from movement disorders.

Compounds with modulating effects on monoamines in cerebral cortex may be used to improve motor and cognitive functions and in the treatment of emotional disturbances related to ageing, neurodegenerative disorders and/or diseases (e.g. Alzheimer's disease, frontotemporal dementia, age-related cognitive impairment and vascular dementia) and developmental disorders (such as Autism spectrum disorders, ADHD, Cerebral Palsy, Gilles de la Tourette's syndrome) as well as after brain injury. Such brain injury may be induced by traumatic, inflammatory, infectious, neoplastic, vascular, hypoxic or metabolic causes or by toxic reactions to exogenous chemicals, wherein the exogenous chemicals are selected from the group consisting of substances of abuse, pharmaceutical compounds, environmental compounds and pharmaceutical compositions according to the present disclosure may also be used in behavioural disorders usually first diagnosed in infancy, childhood, or adolescence as well as in impulse control disorders.

Mood and anxiety disorders, depression and obsessive-compulsive disease may also be treated with compounds and compositions according to the present disclosure.

Compounds of the present disclosure may be used for treating substance abuse disorders as well as disorders characterized by misuse of food. Compounds of the present disclosure are further useful for treatment of a condition selected from the group consisting of sleep disorders, sexual disorders, eating disorders, obesity, and headaches and other pains in conditions characterized by increased muscular tone.

Neurological indications include the use of compounds disclosed herein and their pharmaceutical compositions to improve mental and motor function in Parkinson's disease, and in related parkinsonian syndromes, dyskinesias (such as L-DOPA induced dyskinesias) and dystonias. Compounds disclosed herein may also be used to ameliorate tics and tremor of different origins. Moreover, compounds disclosed herein may be used to relieve pain in conditions characterized by increased muscle tone.

The compounds disclosed herein can also be used in the treatment of Huntington's disease and other movement disorders as well as movement disorders induced by drugs. Restless legs and related disorders as well as narcolepsy may also be treated with compounds according to the present disclosure.

Compounds disclosed herein are considered useful for the treatment and/or prevention of all forms of psychosis, such as schizophrenia and schizophreniform and bipolar disorders as well as drug induced psychotic disorders. Iatrogenic and non-iatrogenic psychoses and hallucinoses may also be treated.

Pharmaceutical Compositions

There is also provided a pharmaceutical composition comprising a therapeutically effective amount of a compound of the present disclosure, or a pharmaceutically acceptable salt thereof, and at least one pharmaceutically acceptable carrier, excipient or diluent.

As used herein, the term "therapeutically effective amount" means an amount of a compound as disclosed herein that is sufficient to induce the desired therapeutic effect in a patient to which the compound is administered.

The present disclosure relates to a pharmaceutical composition comprising a compound of the present invention, and its use in treating CNS disorders. Both organic and inorganic acids can be employed to form non-toxic, pharmaceutically acceptable, acid addition salts of compounds according to the present disclosure. Suitable acid addition salts of compounds of the present disclosure include those formed with pharmaceutically acceptable salts such as those mentioned above. The pharmaceutical composition comprising a compound according to the present disclosure may also comprise excipients used to facilitate the production of the pharmaceutical preparation or the administration of the preparations. Such excipients are well known to people skilled in the art and may for instance be pharmaceutically acceptable adjuvants, diluents, carriers and preservatives.

In clinical practice, compounds according to the present disclosure will normally be administered orally, rectally, nasally or by injection, in the form of a pharmaceutical preparation comprising the active ingredient either as a free base or as a pharmaceutically acceptable non-toxic salt, such as an acid addition salt, e.g. hydrochloride, lactate, acetate or sulfamate salt, in association with a pharmaceutically acceptable carrier, excipient or diluent. The carrier, excipient or diluent may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing a compound according to the present disclosure in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinyl-pyrrolidine, and a lubricant such as magnesium stearate, calcium stearate, polyethylene glycol, waxes, paraffin, and the like, and then compressed into tablets. If coated tablets are required, the cores (prepared as described above) may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the compound may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semi-solids of the drug can be filled into hard gelatine capsules.

Examples of immediate release tablet and capsule formulations suitable for oral administration are given below:

| Tablet I | mg/tablet |
|---|---|
| Compound | 100 |
| Lactose Ph.Eur | 182.75 |
| Croscarmellose sodium | 2.0 |
| Maize starch paste (5% w/v paste) | 2.25 |
| Magnesium stearate | 3.0 |
| Tablet II | mg/tablet |
| Compound | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| Tablet III | mg/tablet |
| Compound | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| Capsule | mg/capsule |
| Compound | 10 |
| Lactose Ph.Eur | 488.5 |
| Magnesium | 1.5 |

Dosage units for rectal application can be solutions or suspensions or can be prepared in the form of suppositories comprising the active substance in a mixture with a neutral fatty base, or gelatin rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also containing stabilizing agents and/ or buffering agents and may conveniently be provided in various dosage unit ampoules. The use and administration to a patient to be treated would be readily apparent to an ordinary skill in the art.

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. Compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve that delivers a measured amount of active compound.

Compounds of the present disclosure may also be administered in a controlled release formulation. The compound is then released at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. The compounds may also be formulated in controlled release formulations in which release of the active compound is targeted. For example, release of the compound may be limited to a specific region of the digestive system through the pH sensitivity of the formulation. Such formulations are well known to persons skilled in the art.

Depending upon the disorder and patient to be treated and the route of administration, the compositions may be administered at varying doses. The dosing will also depend upon the relation of potency to absorbability and the frequency and route of administration. Such doses may be administered once, twice or three or more times daily. The compounds of this invention can be administered to subjects in doses ranging from 0.01 mg to 500 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of diseases. Alternatively, the dosage level is such that a serum concentration of between 0.1 nM to 10 µM of the compound is obtained.

The present disclosure also provides a compound as disclosed herein for use as a medicament.

Further, there is provided a compound as disclosed herein and/or the specific compounds as exemplified herein, or a pharmaceutically acceptable salt thereof, for use in the treatment and/or prevention of a disease, disorder and/or condition which is responsive to modulation of monoamines in the cerebral cortex. Alternatively or additionally, the disease, disorder and/or condition may be as described elsewhere in this document.

There is also provided a use of a compound disclosed herein and/or the specific compounds as exemplified herein, or a pharmaceutically acceptable salt thereof, for the manufacture of a medicament for the treatment and/or prevention of a disease, disorder and/or condition which is responsive to modulation of monoamines in the cerebral cortex. Alternatively or additionally, the disease, disorder and/or condition may be as described elsewhere in this document.

There is also provided a method for treatment and/or prevention of a disease, disorder and/or condition which is responsive to modulation of monoamines in the cerebral cortex, which method comprises the step of administering a therapeutically effective amount of a compound as disclosed herein and/or the specific compounds as exemplified herein, or a pharmaceutically acceptable salt thereof, to a patient in need thereof. Alternatively or additionally, the disease, disorder and/or condition may be as described elsewhere in this document.

For instance, the disease, disorder and/or condition may be selected from the group consisting of dementia, age-related cognitive impairment, cognitive impairment associated with neurodegenerative disorders and/or diseases, autism spectrum disorders, attention deficit hyperactivity disorder (ADHD), affective disorders, schizophrenia, anxiety disorders and movement disorders. Examples of dementia include Alzheimer's disease and frontotemporal dementia. Examples of autism spectrum disorders include autism and Asperger's syndrome. Examples of affective disorders include major depression disorder, bipolar disorder and depression. Examples of anxiety disorders include panic disorder, generalized Anxiety Disorder (GAD) and social phobia. Examples of movement disorders include Parkinson's disease and Huntington's disease. Alternatively or additionally, the disease, disorder and/or condition may be as described elsewhere in this document.

In a further example, the disease, disorder and/or condition may be selected from the group consisting of dementia, age-related cognitive impairment, cognitive impairment associated with neurodegenerative disorders and/or diseases, autism spectrum disorders, affective disorders, schizophrenia, anxiety disorders, attention deficit hyperactivity disorder (ADHD) and movement disorders. In still a further example, the disease, disorder and/or condition may be selected from the group consisting of dementia, age-related cognitive impairment and schizophrenia.

In this document, treatment and/or prevention of a disease, disorder and/or condition may involve alleviation of symptoms associated with said disease, disorder and/or condition. For instance, the alleviation of symptoms may be reduction of the symptoms or rendering the symptoms less difficult.

Combination Therapy

One or more compounds as described herein may be combined with at least one other therapeutically active agent, said therapeutically active agent being is useful in the treatment and/or prevention of a disease, disorder and/or a condition which is responsive to modulation of monoamines in the cerebral cortex. For instance, the disease, disorder or condition may be selected from the group consisting of dementia, age-related cognitive impairment, neurodegenerative related cognitive disorders and/or diseases, autism spectrum disorders, attention deficit hyperactivity disorder (ADHD), affective disorders, depression, schizophrenia, anxiety disorders, and panic disorder. Alternatively or additionally, the disease, disorder and/or condition may be as described elsewhere in this document.

The combination of one or more compounds as disclosed herein with the at least one other therapeutically active agent may be provided as a single composition. Alternatively, the combination may be provided as a kit of parts.

Thus, there is provided a kit of parts comprising or consisting of:
(i) a compound as disclosed herein, and
(ii) a therapeutically active agent, said therapeutically active agent being is useful in the treatment, prevention or alleviation of a disease or a disorder or a condition which is responsive to modulation of monoamines in the cerebral cortex.

The compound of component (i) of the kit of parts may be provided together with a pharmaceutically acceptable carrier, excipient and/or diluent. Further, the therapeutically active agent of component (ii) of the kit of parts may be provided together with a pharmaceutically acceptable carrier, excipient and/or diluent.

The kit of parts may further comprise instructions for use, such as instructions for simultaneous, sequential or separate administration of the compound of component (i) and the therapeutically active agent of component (ii) of the kit of parts.

There is also provided a combination such as a single composition or a kit of parts as disclosed herein for use as a medicament.

Further, there is provided a combination such as a single composition or a kit of parts as disclosed herein for use in the treatment and/or prevention of a disease, disorder or condition which is responsive to modulation of monoamines in the cerebral cortex.

Further, there is provided a combination such as a single composition or a kit of parts as disclosed herein for use in the manufacture of a medicament for the treatment of a disease, disorder and/or condition which is responsive to modulation of monoamines in the cerebral cortex.

Further, there is provided a method of treatment of a disease, disorder and/or condition which is responsive to modulation of monoamines in the cerebral cortex, said method comprising the administration of an effective amount of such as a single composition or the components of a kit of parts as disclosed herein to a patient in need thereof.

It will be appreciated that the compound of component (i), and the therapeutically agent of component (ii) of the kit of parts disclosed herein may be administered simultaneously, sequentially or separately.

Further, it will be appreciated in the context of the combination such as the single composition or the kit of parts disclosed herein that the disease, disorder and/or condition may be selected from the group consisting of dementia, age-related cognitive impairment, neurodegenerative related cognitive disorders and/or diseases, autism spectrum disorders, attention deficit hyperactivity disorder (ADHD), affective disorders, depression, schizophrenia, anxiety disorders, and panic disorder. Alternatively or additionally, the disease, disorder or condition may be as described elsewhere in this document.

EXAMPLES

The invention is further illustrated in the examples below and as outlined below, which in no way are intended to limit the scope of the invention. The following general experimental procedures were used:
(i) Low resolution mass spectra were recorded on a HP 5970A instrument operating at an ionization potential of 70 eV. The mass detector was interfaced with a HP5700 gas chromatograph equipped with a HP-5MS UI GC column (15 m, 0.25 mm, 0.25 μm) with He gas flow 40 cm/s.
(ii) Liquid chromatography-mass spectra (LC MS) were acquired using a HP-Agilent 1100 MSD system using an aqueous solution of acetic acid as mobile phase (0.03% acetic acid).
(iii) NMR experiments were run on a Oxford 800 magnet, Bruker Avance III HD spectrometer with 4 channels, 5 mm TXO cold probe and ASTM 13C S/N 3300 or, using a Varian Mercury 400 MHz spectrometer.
(iv) Melting points were determined by a Buchi B-545 and are uncorrected.
(v) For flash chromatography, Biotage Isolera Vers 1.2 with SNAP Cartridge KP-Sil, mobile phase gradient mixtures of isooctane/ethyl acetate/methanol was used.
(vi) Evaporation of solvents was performed using a Laborota 4000 connected to a Vario PC2001 vacuum pump.

The naming of compounds as disclosed herein were made using the software package J Chem for Excel, ver. 16.10.1700.3473. In this document, if the chemical name and the chemical structure are inconsistent the chemical structure should be considered to be correct.

Abbreviations

The following abbreviations are employed herein:
NA norepinephrine (noradrenaline)
NM normetanephrine
DA dopamine
DOPAC 3,4-dihydroxyphenylacetic acid
3-MT 3-methoxytyramine
5-HT serotonin (5-hydroxytryptamine)
$Cs_2CO_3$ Caesium carbonate
DCM dichloromethane
DEAD diethylazodicarboxylate
$Et_2O$ diethyl ether
EtOH ethanol
EtOAc ethyl acetate
GC MS Gas Chromatography Mass Spectrometry
bp base peak
HCl hydrogen chloride
LC MS Liquid Chromatography Mass Spectrometry
MTBE methyl tert-butyl ether
MeOH methanol
m.p. melting point
NaOH sodium hydroxide
$Na_2SO_4$ sodium sulfate
TFA trifluoroacetic acid
SERT serotonin transporter
NET norepinephrine transporter (noradrenaline transporter)
DAT dopamine transporter
SNDRI serotonin-norepinephrine-dopamine reuptake inhibitor
TRI triple reuptake inhibitor
FC frontal cortex
Stri striatum
M molar
nM nanomolar
General

PROPHETIC EXAMPLES

The compounds of the prophetic examples form part of the present disclosure and may be prepared in analogy with the procedures described for Examples 1-4 using appropriate starting materials and reagents. All prophetic examples are indicated as being prophetic prior to the Example number.

N-Alkylation

Also, an optional N-alkylation reaction may be performed by using alkylation techniques that are well known for the skilled person. For instance, a compound according to Formula I, wherein $R_5$ is H, may be alkylated in a solvent, such as, THF, by adding a base, such as triethylamine, followed by an alkylating agent, such as for instance methyl iodide or ethyl iodide. Alternatively, the alkylation reaction may be a reductive alkylation reaction. Thus, a compound according to Formula I, wherein $R_5$ is H, may be alkylated in a solvent, such as DCM, by adding an appropriate aldehyde, such as formaldehyde or acetaldehyde, followed by a reducing agent, such as, for instance, sodium triacetoxyborohydride. Optionally, such a reductive alkylation reaction may be performed in the presence of an acid, such as, for instance, acetic acid.

Isotope Labelled Compounds

Isotope labelled compounds may be prepared by using commercially available isotope labelled starting materials or by standard procedures well known in the art. For instance, one, two or three deuterium atoms may be introduced into the 2,4 and/or 6-position of the aromatic ring of the compounds of the invention by treating the appropriate phenol starting material with a strong acid comprising acidic deuterium atoms (see e.g. Perrin et al., J. Am. Chem. Soc. 2007, 129, 4490-4497). Such a procedure provides a starting material comprising one, two or three deuterium atoms in the ortho and/or para positions of the phenol. Alternatively, or additionally, one deuterium atom may be introduced into the azetidine ring of the compounds of the invention by treating commercially available tert-butyl 3-oxoazetidine-1-carboxylate with a reducing agent comprising deuterium, such as, for instance, sodium borodeuteride ($NaBD_4$) in an organic solvent, such as for instance a lower alcohol for example deuterated ethanol. Such a procedure provides tert-butyl 3-hydroxy-3-($^2$H)azetidine-1-carboxylate as a starting material. Furthermore, five deuterium atoms may be introduced into the azetidine ring of the compounds of the invention by a procedure using commercially available deuterated epichlorohydrine (see for instance page 76 of WO 2012/168817). Such a procedure provides 1-(diphenylmethyl)($^2$H$_5$)azetidine-3-yl methanesulfonate as a starting material. Said sulfonate derivative can then be used in an alkylation reaction where the appropriate phenol starting material is being O-alkylated in a similar fashion as is described hereinafter in Preparation 2 and Preparation 3. Deprotection of the diphenylmethyl group can be accomplished by a procedure as described in Example 4. Furthermore, four deuterium atoms may be introduced in the azetidine ring of the compounds of invention by using procedures disclosed in WO 2017/045648. Such procedures would provide compounds of the invention having four deuterium atoms in the 2 and 4-positions of the azetidine ring. Finally, deuterium atoms can be introduced in the optional alkyl group $R_5$ of Formula I by alkylating the nitrogen atom of the azetidine ring with a commercially available deuterated alkylating agent.

Example 1A 3-(2,3-difluorophenoxy)azetidine hydrochloric acid salt

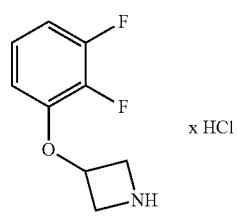 [SMILES: Fc1cccc(OC2CNC2)c1F]

To a solution of tert-butyl 3-(2,3-difluorophenoxy)azetidine-1-carboxylate (Preparation 1) (3.00 g, 10.5 mmol) in DCM (10 mL) was added TFA (5.00 mL, 67.0 mmol). The solution was stirred for 24 h and the solvent was evaporated. The residue was partitioned between EtOAc and water and the aqueous phase was made alkaline using an aqueous NaOH solution (0.1 M). The layers were separated and the aqueous phase extracted with EtOAc. The combined organic solutions were dried ($Na_2SO_4$) and the solvent was evaporated. The product was purified by chromatography on silica gel using a mixture of EtOAc and MeOH as eluent (gradient, 0%-100% MeOH). There was obtained 1.43 g (73%) of the non-salt form of 3-(2,3-difluorophenoxy)azetidine. Part of the material (0.80 g, 4.32 mmol) was then dissolved in MeOH and to the solution was added HCl (1.25 M in EtOH). The mixture was concentrated and then repeatedly co-evaporated with EtOH. The residue was dissolved in a small amount of MeOH and a mixture of $Et_2O$ and diisopropyl ether (9:1) was added until the solution became cloudy. The mixture was placed in a refrigerator and after some time a solid material precipitated. The solid was isolated by filtration, the filter cake washed with $Et_2O$ and then dried at 60-75° C. There was obtained 0.70 g (73%) of title compound as a white solid with a m.p. of 134.5° C. $^1$H NMR (400 Mz, methanol-$d_4$): δ 4.25 (m, 2H), 4.61 (m, 2H), 5.24 (m, 1H), 6.78 (m, 1H), 6.99 (m, 1H), 7.14 (m, 1H).

Example 1B 3-(2,3-difluorophenoxy)azetidine fumaric acid salt

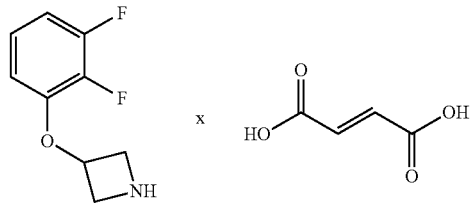 [SMILES: Fc1cccc(OC2CNC2)c1F ; O=C(O)/C=C/C(=O)O]

The non-salt form of 3-(2,3-difluorophenoxy)azetidine (234 mg, 1.26 mmol) that had been obtained from tert-butyl 3-(2,3-difluorophenoxy)azetidine-1-carboxylate (Preparation 1) in a similar fashion as is described in Example 1A was dissolved in EtOH (5 mL). To the resultant solution was added fumaric acid (145 mg, 1.25 mmol) and the mixture was heated to reflux until almost all of the acid was dissolved when the desired product started to precipitate. The slurry was stirred at room temperature over night and the solid was isolated by filtration. The crystals were dried in vacuo at room temperature for one hour and then in an oven at 70° C. for 2 h. There was obtained 250 mg (65%) of title compound as a white solid with a m.p. of 138.8° C. $^1$H NMR (800 Mz, methanol-$d_4$): δ 4.22 (m, 2H), 4.57 (m, 2H), 5.22 (m, 1H), 6.71 (s, 2H), 6.75 (m, 1H), 6.97 (m, 1H), 7.12 (m, 1H). LC MS m/z 115 [M−H]$^−$ and 186 [M+H]$^+$.

Example 2

3-(2,3,5-trifluorophenoxy)azetidine hydrochloric acid salt

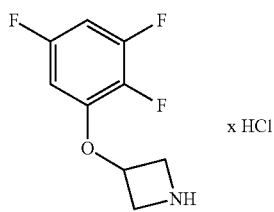 [SMILES: Fc1cc(F)c(F)c(OC2CNC2)c1]

To a solution of tert-butyl 3-(2,3,5-trifluorophenoxy)azetidine-1-carboxylate (Preparation 2) (0.80 g, 2.64 mmol) in DCM (5 mL) was added dropwise TFA (1.00 mL, 13.4 mmol). The solution was stirred for 48 h. The solvent was evaporated and then repeatedly co-evaporated with MeOH. The residue was dried in vacuum for 2 h and then dissolved in MeOH (10 mL). To the solution was added a concentrated aqueous solution of NaOH (0.12 g, 3 mmol) and the product was purified on a Biotage Isolute SCX-3 SPE column, washing with MeOH, then eluting with ammonia/MeOH (1.8 M). The volatiles were removed by evaporation and the residue re-dissolved in EtOH. HCl (1.25 M in EtOH, 2 mL) was added and the solution was concentrated until most of the solvent was removed. Et$_2$O was added dropwise until the solution became cloudy and the mixture was stirred at ambient temperature for 4 h. After filtration, the solid was dried under reduced pressure for one hour and then at normal pressure at 70° C. for 2 h. There was obtained 0.37 g (58%) of the title compound as a white solid with a m.p. of 153.7° C. $^1$H NMR (800 Mz, DMSO-d$_6$): δ 4.04 (m, 2H), 4.47 (m, 2H), 5.18 (m, 1H), 6.94 (m, 1H), 7.18 (m, 1H), 9.60 (s, 2H). LC MS m/z 204 [M+H]$^+$.

Example 3

3-(2,3,5,6-tetrafluorophenoxy)-azetidine hydrochloric acid salt

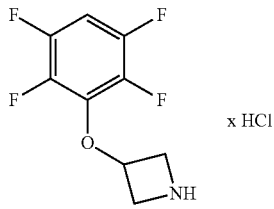 [SMILES: Fc1cc(F)c(F)c(OC2CNC2)c1F]

To a solution of tert-butyl 3-(2,3,5,6-tetrafluorophenoxy)azetidine-1-carboxylate (Preparation 3) (0.60 g, 1.87 mmol) in DCM (5 mL) was added dropwise TFA (1.00 mL, 13.4 mmol). The solution was stirred for 20 h. The solvent was removed by evaporation. The residue was repeatedly co-evaporated with MeOH, dried in vacuum for 2 h and then dissolved in MeOH (10 mL). To the solution was added an aqueous solution of NaOH (2 M, 1 mL) and the product was purified on a Biotage Isolute SCX-3 SPE column washing with MeOH and then eluting with ammonia/MeOH (1.8 M). The solvent was removed by evaporation and the residue (0.25 g) was dissolved in EtOH. HCl (1.25 M in EtOH, 2 mL) was added dropwise and the solution was concentrated until most of the solvent was removed. Et$_2$O was added dropwise until the solution became cloudy and the mixture was stirred at ambient temperature for 3 days. After decantation, the solid was dried under reduced pressure for one hour and then at normal pressure at 70° C. for 2 h. There was obtained 0.25 g (52%) of the title compound as a white solid with a m.p. of 152.7° C. $^1$H NMR (800 Mz, DMSO-d$_6$): δ 4.14 (m, 2H), 4.33 (m, 2H), 5.20 (m, 1H), 7.69 (m, 1H), 9.54 (s, 2H). LC MS m/z 222 [M+H]$^+$.

Example 4

3-methyl-3-(2,3,5-trifluoro-phenoxy)azetidine hydrochloric acid salt

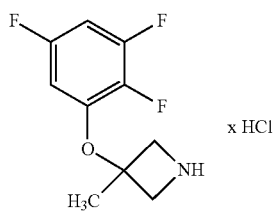

While cooling with an ice bath, 1-chloroethyl chloroformate (0.50 mL, 4.60 mmol) was added dropwise to a solution of 1-(diphenylmethyl)-3-methyl-3-(2,3,5-trifluorophenoxy)azetidine (Preparation 4) (1.30 g, 3.40 mmol) in DCM (20 mL). The mixture was stirred with cooling for one hour, at ambient temperature for 16 h and then the volatiles were removed by evaporation. The residue was dissolved in MeOH (20 mL) and the solution was heated to reflux for 4 h. The solvent was removed by evaporation and the residue was partitioned between DCM and an aqueous Na$_2$CO$_3$ solution (10%). The aqueous layer was extracted with DCM (3×30 mL) and the combined organic solutions were dried (Na$_2$SO$_4$) and evaporated. Purification by chromatography on silica gel eluting with EtOAc and MeOH (1:1) gave an oil (0.45 g) that was dissolved in EtOH (20 mL). HCl (1.25 M in EtOH, 1.5 mL) was added dropwise and the solution was concentrated until most of the solvent was removed. Et$_2$O was added dropwise until the solution became cloudy and the mixture was stirred at ambient temperature overnight. After the formed precipitate was collected by filtration, the filter cake was washed with Et$_2$O and the solid was dried under reduced pressure for one hour and then further dried at normal pressure at 70° C. for 2 h. There was obtained 0.32 g (37%) of the title compound as a white solid with a m.p. of 164.7° C. $^1$H NMR (800 Mz, DMSO-d$_6$): δ 1.67 (s, 3H), 4.17 (d, 2H), 4.24 (d, 2H), 6.85 (m, 1H), 7.21 (m, 1H), 9.46 (s, 2H). LC MS m/z 218 [M+H]$^+$.

Example 5

3-(2,3-difluorophenoxy)-1-methylazetidine

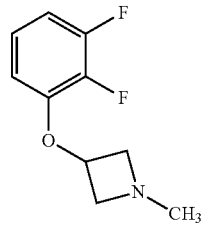

The non-salt form of 3-(2,3-difluorophenoxy)azetidine (0.35 g, 1.89 mmol) that had been obtained from Preparation 1 in a similar fashion as described in Example 1A was dissolved in dry DCM (10 mL) together with acetic acid (0.21 mL, 3.78 mmol). To the solution was added an aqueous solution of formaldehyde (37%, 0.42 mL, 5.67 mmol) and the mixture was stirred for 15 min at room temperature. Sodium triacetoxyborohydride (1.2 g, 5.67 mmol) was added portion-wise and the mixture was stirred for one hour. An aqueous solution of $Na_2CO_3$ (10%) was added and the mixture was extracted with DCM. The organic solution was dried ($Na_2SO_4$) and then the volatiles were removed by evaporation. The residue (0.34 g) was purified by column chromatography on silica-gel using a gradient of MeOH/EtOAc (0-20% MeOH) to provide 240 mg (63%) of the non-salt form of 3-(2,3-difluorophenoxy)-1-methylazetidine. GC MS m/z (relative intensity, 70 eV). 199 (6), 157 (9), 156 (bp), 155 (15), 138 (2), 137 (19), 136 (18), 131 (5), 130 (72), 128 (14), 127 (75), 113 (4), 110 (3), 109 (7), 108 (12), 102 (4), 101 (12), 82 (10), 81 (4), 75 (6), 70 (20), 69 (2), 68 (6), 63 (9), 58 (4), 57 (8), 51 (3).

Prophetic Example 6

3-(2,3-difluorophenoxy)-1-ethylazetidine

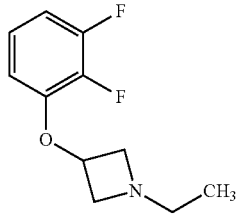

Prophetic Example 7

3-(2,3-difluorophenoxy)-3-methylazetidine

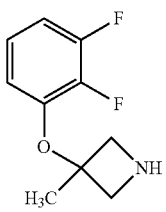

Prophetic Example 8

3-(2,3-difluorophenoxy)-1,3-dimethylazetidine

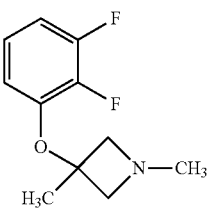

Prophetic Example 9

3-(2,3-difluorophenoxy)-1-ethyl-3-methylazetidine

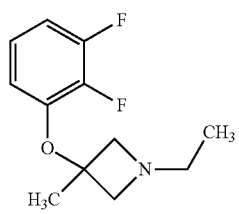 [SMILES: CCN1CC(C)(Oc2cccc(F)c2F)C1]

Example 10

3-(2,3,4-trifluoro-phenoxy)azetidine fumaric acid salt

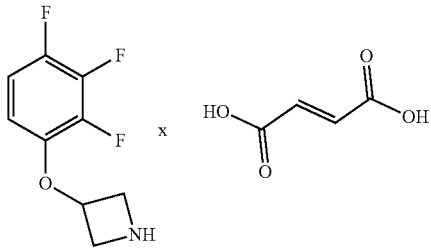 [SMILES: Fc1ccc(OC2CNC2)c(F)c1F ; O=C(O)/C=C/C(=O)O]

To a solution of tert-butyl 3-(2,3,4-trifluorophenoxy)azetidine-1-carboxylate (Preparation 5) (0.66 g, 2.20 mmol) in DCM (10 mL) was added TFA (1.5 mL, 20 mmol). The solution was stirred for 24 h. Evaporation removed the volatiles and the resultant residue was co-evaporated with DCM and then partitioned between DCM and an aqueous $Na_2CO_3$ solution (10%). The organic solution was filtered through a phase separator and then concentrated under reduced pressure to give 390 mg of the non-salt form of 3-(2,3,4-trifluoro-phenoxy)azetidine as an oil. A part of that preparation (300 mg, 1.5 mmol) was dissolved in EtOH and to the solution was added fumaric acid (170 mg, 1.5 mmol). The mixture was heated to 75° C. for 15 min and then stirred at RT for 2 h. After filtration, the solid was dried under vacuum for one hour and then at normal pressure at 70° C. for 2 h. There was obtained 0.21 g (39%) of the title compound as a white solid with a m.p. of 153.0° C. $^1$H NMR (800 Mz, DMSO-d$_6$): δ 3.96 (m, 2H), 4.30 (m, 2H), 5.14 (m, 1H), 6.50 (s, 2H), 6.86 (m, 1H), 7.26 (m, 1H). LC MS m/z 204 [M+H]$^+$.

Prophetic Example 11

1-methyl-3-(2,3,4-trifluoro-phenoxy)azetidine

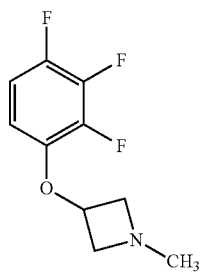

Prophetic Example 12

1-ethyl-3-(2,3,4-trifluoro-phenoxy)azetidine

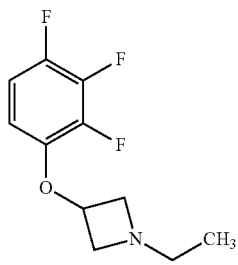 [SMILES: CCN1CC(Oc2ccc(F)c(F)c2F)C1]

Prophetic Example 13

3-methyl-3-(2,3,4-trifluoro-phenoxy)azetidine

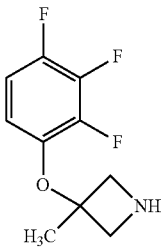

Prophetic Example 14

1,3-dimethyl-3-(2,3,4-trifluorophenoxy)azetidine

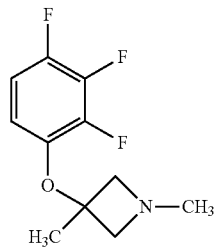 [SMILES: CN1CC(C)(Oc2ccc(F)c(F)c2F)C1]

Prophetic Example 15

1-ethyl-3-methyl-3-(2,3,4-trifluorophenoxy)azetidine

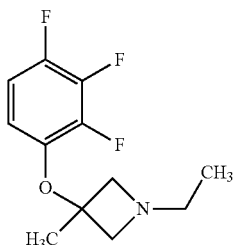

Prophetic Example 16

1-methyl-3-(2,3,5-trifluoro-phenoxy)azetidine

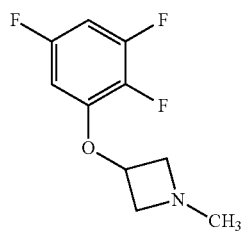

Prophetic Example 17

1-ethyl-3-(2,3,5-trifluoro-phenoxy)azetidine

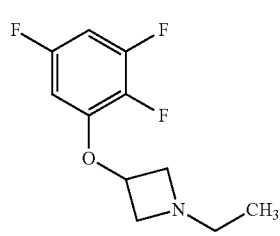 [SMILES: CCN1CC(Oc2cc(F)cc(F)c2F)C1]

Prophetic Example 18

1,3-dimethyl-3-(2,3,5-trifluorophenoxy)azetidine

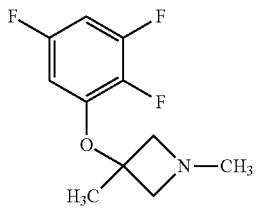

Prophetic Example 19

1-ethyl-3-methyl-3-(2,3,5-trifluorophenoxy)azetidine

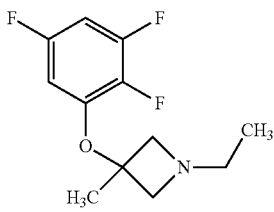 [SMILES: CCN1CC(C)(Oc2cc(F)cc(F)c2F)C1]

Example 20

3-(2,3,6-trifluorophenoxy)azetidine hydrochloric acid salt

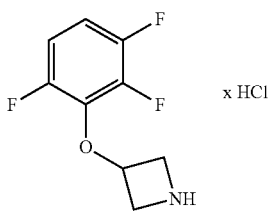 [SMILES: Fc1ccc(F)c(OC2CNC2)c1F]

To a solution of tert-butyl 3-(2,3,6-trifluorophenoxy)azetidine-1-carboxylate (Preparation 6) (1.40 g, 4.61 mmol) in DCM (25 mL) was added TFA (3.0 mL, 39 mmol). The solution was stirred for 24 h. The volatiles were removed by evaporation. The residue was co-evaporated with DCM and then partitioned between DCM and an aqueous $Na_2CO_3$ solution (10%). The organic solution was filtered through a phase separator and then concentrated under reduced pressure to give the non-salt form of 3-(2,3,6-trifluorophenoxy)azetidine (0.78 g). The residue was dissolved in EtOH (25 mL) together with HCl (1.25 M in EtOH, 4 mL). The mixture was concentrated under reduced pressure and drop-wise to the residue was added diisopropyl ether (15 mL). The resultant slurry was stirred at 0° C. for one hour and then the solid was isolated by filtration. The filter cake was dried under vacuum for one hour and then at normal pressure at 70° C. for 2 h. There was obtained 0.63 g (56%) of the title compound as a white solid with a m.p. of 113.9° C. $^1$H NMR (800 Mz, DMSO-$d_6$): δ 4.12 (m, 2H), 4.32 (m, 2H), 5.12 (m, 1H), 7.27 (m, 2H), 9.44 (s, 2H). LC MS m/z 204 [M+H]$^+$.

Prophetic Example 21

1-methyl-3-(2,3,6-trifluoro-phenoxy)azetidine

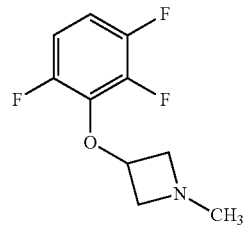

Example 22

1-ethyl-3-(2,3,6-trifluoro-phenoxy)azetidine oxalic acid salt

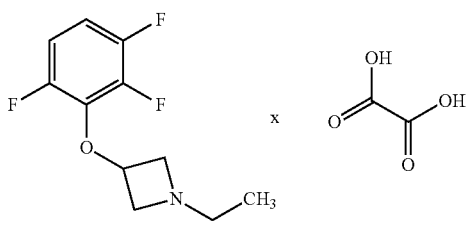 [SMILES: CCN1CC(Oc2c(F)ccc(F)c2F)C1 ; O=C(O)C(=O)O]

The non-salt form of 3-(2,3,6-trifluorophenoxy)azetidine (0.500 g, 2.46 mmol) that had been obtained from tert-butyl 3-(2,3,6-trifluorophenoxy)azetidine-1-carboxylate (Preparation 6) in a similar fashion as described in Example 20 was dissolved in dry THF (10 mL). To the resultant solution was added triethylamine (1.0 mL, 7.38 mmol) and iodoethane (0.25 mL, 3.2 mmol). The mixture was stirred for 24 h and then the volatiles were removed by evaporation. The residue was partitioned between MTBE (20 mL) and an aqueous solution of HCl (10%, 20 mL). The phases were separated and the aqueous solution was pH-adjusted to a pH over 10 by portion-wise addition of solid $Na_2CO_3$. The mixture was extracted with DCM (3×25 mL) and the combined organic solutions were dried ($Na_2SO_4$) and evaporated. The residue was purified by column chromatography on silica-gel using a gradient of MeOH/EtOAc (0-20% MeOH) to provide the non-salt form of the title compound as an oil (0.31 g). The residue was dissolved in ethanol and to the resulting solution was added an ethanol solution of oxalic acid dihydrate (169 mg, 1.34 mmol). The mixture was concentrated and the residue was dissolved in hot methanol. After cooling to room temperature, diethyl ether was added drop-wise until the mixture became cloudy. On allowing to stand overnight a precipitate formed that was isolated by filtration. The crystals were air-dried in the hood and then in an oven at 70° C. for 2 h. There was obtained 0.31 g (41%) of title compound as a white solid with a m.p. of 154.1° C. $^1$H NMR (800 Mz, methanol-$d_4$): δ 1.28 (t, 3H), 3.37 (m, 2H), 4.37 (s, 2H), 4.62 (s, 2H), 5.15 (m, 1H), 7.09 (m, 2H). LC MS m/z 232 [M+H]$^+$.

41

Prophetic Example 23

3-methyl-3-(2,3,6-trifluoro-phenoxy)azetidine

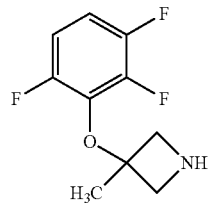

Prophetic Example 24

1,3-dimethyl-3-(2,3,6-trifluoro-phenoxy)azetidine

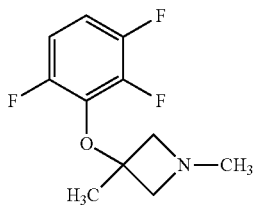 [SMILES: CN1CC(C)(Oc2c(F)ccc(F)c2F)C1]

Prophetic Example 25

1-ethyl-3-methyl-3-(2,3,6-trifluorophenoxy)azetidine

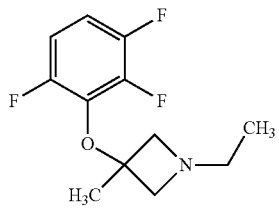 [SMILES: CCN1CC(C)(Oc2c(F)ccc(F)c2F)C1]

Prophetic Example 26

3-(2,3,4,5-tetrafluoro-phenoxy)azetidine

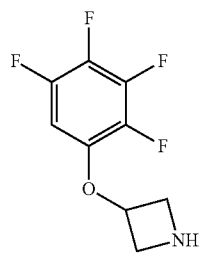

42

Prophetic Example 27

1-methyl-3-(2,3,4,5-tetrafluoro-phenoxy)azetidine

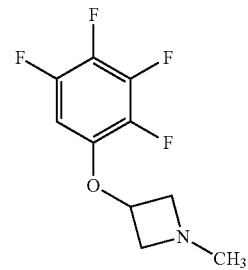

Prophetic Example 28

1-ethyl-3-(2,3,4,5-tetrafluoro-phenoxy)azetidine

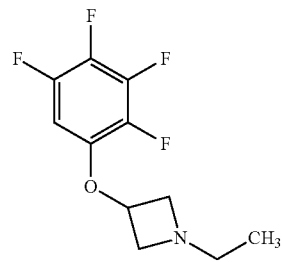 [SMILES: CCN1CC(Oc2cc(F)c(F)c(F)c2F)C1]

Prophetic Example 29

3-methyl-3-(2,3,4,5-tetrafluorophenoxy)azetidine

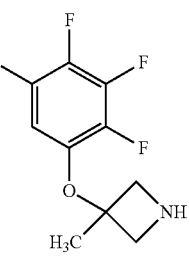

Prophetic Example 30
1,3-dimethyl-3-(2,3,4,5-tetrafluorophenoxy)azetidine
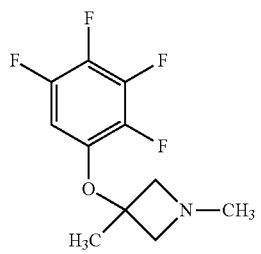 [SMILES: CN1CC(C)(Oc2cc(F)c(F)c(F)c2F)C1]
Prophetic Example 31
1-ethyl-3-methyl-3-(2,3,4,5-tetrafluorophenoxy)azetidine
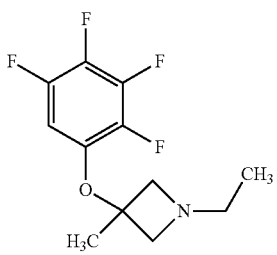 [SMILES: CCN1CC(C)(Oc2cc(F)c(F)c(F)c2F)C1]
Prophetic Example 32
3-(2,3,4,6-tetrafluorophenoxy)-azetidine
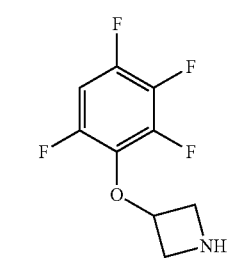 [SMILES: Fc1cc(F)c(OC2CNC2)c(F)c1F]
Prophetic Example 33
1-methyl-3-(2,3,4,6-tetrafluorophenoxy)azetidine
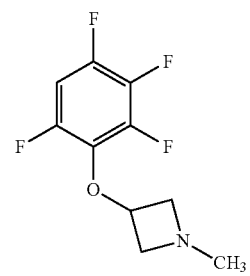
Prophetic Example 34
1-ethyl-3-(2,3,4,6-tetrafluoro-phenoxy)azetidine
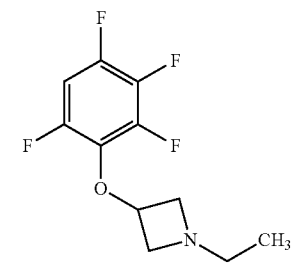 [SMILES: CCN1CC(Oc2c(F)cc(F)c(F)c2F)C1]
Prophetic Example 35
3-methyl-3-(2,3,4,6-tetrafluorophenoxy)azetidine
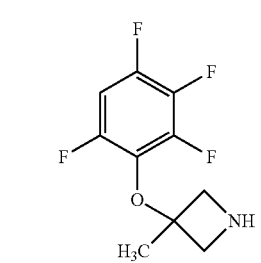 [SMILES: CC1(Oc2c(F)cc(F)c(F)c2F)CNC1]

Prophetic Example 36

1,3-dimethyl-3-(2,3,4,6-tetrafluorophenoxy)azetidine

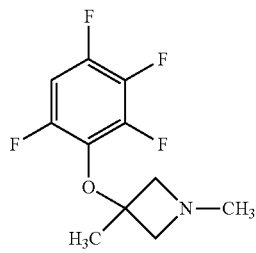 [SMILES: CN1CC(C)(Oc2c(F)cc(F)c(F)c2F)C1]

Prophetic Example 37

1-ethyl-3-methyl-3-(2,3,4,6-tetrafluorophenoxy)azetidine

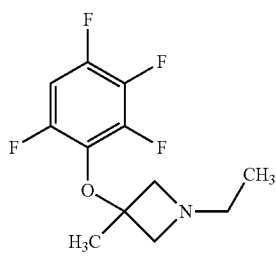 [SMILES: CCN1CC(C)(Oc2c(F)cc(F)c(F)c2F)C1]

Example 38

1-methyl-3-(2,3,5,6-tetrafluorophenoxy)azetidine hydrochloric acid salt

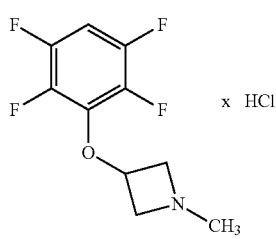 [SMILES: CN1CC(Oc2c(F)c(F)cc(F)c2F)C1]

To a solution of 3-(2,3,5,6-tetrafluorophenoxy)azetidine (Preparation 7) (0.34 g, 1.52 mmol) and triethylamine (0.7 mL, 5.0 mmol) in dry THF (10 mL) was added iodomethane (0.1 mL, 1.6 mmol). The mixture was stirred for 16 h and then the volatiles were removed by evaporation. The residue was partitioned between MTBE (10 mL) and an aqueous solution of HCl (10%, 10 mL). The phases were separated and the aqueous solution was pH-adjusted to a pH of 10-11 by portion-wise addition of solid $Na_2CO_3$. The mixture was extracted with DCM (3×10 mL) and the combined organic solutions were filtered through a phase-separator, then concentrated under reduced pressure. The resulting residue was purified by column chromatography on silica-gel using a gradient of MeOH/EtOAc (0-10% MeOH) to provide an oil (100 mg) that was dissolved in ethanol (10 mL). To the resulting solution was added HCl (1.25 M in EtOH, 0.7 mL). The mixture was stirred at RT for 20 min and then concentrated under reduced pressure. Drop-wise to the residue was added diethyl ether and after one hour, the formed solid was isolated by decantation. The solid was dried under vacuum for one hour and then at normal pressure at 70° C. for 2 h. There was obtained 97 mg (24%) of the title compound as a white solid with a m.p. of 120.3° C. $^1$H NMR (800 Mz, DMSO-$d_6$): δ 2.89 (s, 3H), 4.26 (m, 2H), 4.47 (m, 2H), 5.17 (m, 1H), 7.71 (m, 1H), 11.01 (s, 1H). LC MS m/z 236 [M+H]$^+$.

Example 39

1-ethyl-3-(2,3,5,6-tetrafluorophenoxy)azetidine hydrochloric acid salt

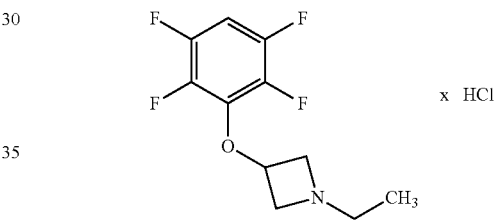

To a solution of 3-(2,3,5,6-tetrafluorophenoxy)azetidine (Preparation 7) (0.49 g, 2.21 mmol) and triethylamine (1.0 mL, 7.2 mmol) in dry THF (10 mL) was added iodoethane (0.25 mL, 3.1 mmol). The mixture was stirred for three days and then the volatiles were removed by evaporation. The residue was partitioned between MTBE (20 mL) and an aqueous solution of HCl (10%, 20 mL). The phases were separated and the aqueous solution was pH-adjusted to a pH over 10 by portion-wise addition of solid $Na_2CO_3$. The mixture was extracted with DCM (3×10 mL), the combined organic solutions were filtered through a phase-separator and then concentrated under reduced pressure. The resulting residue was purified by column chromatography on silica-gel using a gradient of MeOH/EtOAc (0-8% MeOH) to provide an oil (0.33 g) that was dissolved in ethanol (10 mL). To the resulting solution was added HCl (1.25 M in EtOH, 2 mL). The mixture was stirred at RT for 20 min and then concentrated under reduced pressure. Drop-wise to the residue was added diethyl ether and after one hour the formed solid was isolated by filtration. The filter cake was washed with diethyl ether and then dried under vacuum for one hour and then at normal pressure at 70° C. for 2 h. There was obtained 203 mg (32%) of the title compound as a white solid with a m.p. of 135.3° C. $^1$H NMR (800 Mz, DMSO-de): δ 1.14 (t, 3H), 3.24 (q, 2H), 4.25 (m, 2H), 4.45 (m, 2H), 5.18 (m, 1H), 7.70 (m, 1H), 11.20 (s, 1H). LC MS m/z 250 [M+H]$^+$.

Prophetic Example 40

3-methyl-3-(2,3,5,6-tetrafluorophenoxy)azetidine

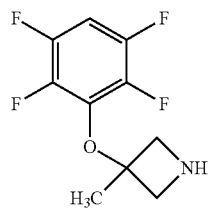 [SMILES: CC1(Oc2c(F)c(F)cc(F)c2F)CNC1]

Prophetic Example 41

1,3-dimethyl-3-(2,3,5,6-tetrafluorophenoxy)azetidine

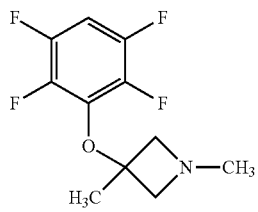 [SMILES: CN1CC(C)(Oc2c(F)c(F)cc(F)c2F)C1]

Prophetic Example 42

1-ethyl-3-methyl-3-(2,3,5,6-tetrafluorophenoxy)azetidine

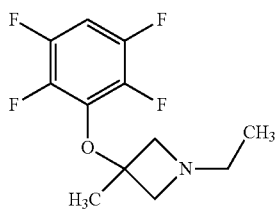 [SMILES: CCN1CC(C)(Oc2c(F)c(F)cc(F)c2F)C1]

Example 43

3-(2,3,4,5,6-pentafluoro-phenoxy)azetidine hydrochloric acid salt

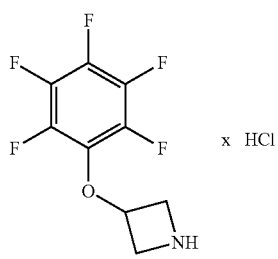 [SMILES: Fc1c(F)c(F)c(OC2CNC2)c(F)c1F]

To a solution of tert-butyl 3-(2,3,4,5,6-pentafluorophenoxy)azetidine-1-carboxylate (Preparation 8) (1.60 g, 4.72 mmol) in DCM (25 mL) was added TFA (4.0 mL, 52 mmol). The solution was stirred for 24 h. The volatiles were removed by evaporation and the residue was co-evaporated with DCM and then partitioned between DCM and an aqueous Na$_2$CO$_3$ solution (10%). The organic solution was filtered through a phase separator and then concentrated under reduced pressure. The resultant residue (1.0 g) was co-evaporated with ethanol and then dissolved in EtOH (20 mL) together with HCl (1.25 M in EtOH, 4 mL). The mixture was concentrated under reduced pressure and diisopropylether (15 mL) was added dropwise to the residue. The formed slurry was stirred at 0° C. for one hour and then the solid was isolated by filtration. The filter cake was dried under vacuum for one hour and then at normal pressure at 70° C. for 2 h. There was obtained 0.63 g (48%) of the title compound as an off-white solid with a m.p. of 135.5° C. $^1$H NMR (800 Mz, DMSO-d$_6$): δ 4.12 (m, 2H), 4.32 (m, 2H), 5.13 (m, 1H), 9.49 (s, 2H). LC MS m/z 240 [M+H]$^+$.

Prophetic Example 44

1-methyl-3-(2,3,4,5,6-pentafluorophenoxy)azetidine

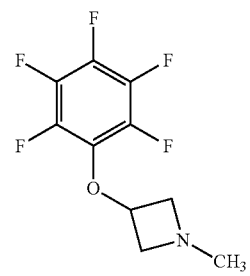

Prophetic Example 45

1-ethyl-3-(2,3,4,5,6-pentafluorophenoxy)azetidine

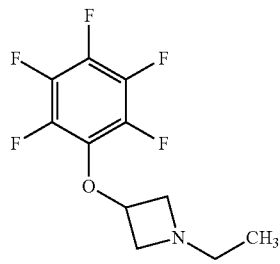 [SMILES: CCN1CC(Oc2c(F)c(F)c(F)c(F)c2F)C1]

Prophetic Example 46

3-methyl-3-(2,3,4,5,6-pentafluorophenoxy)azetidine

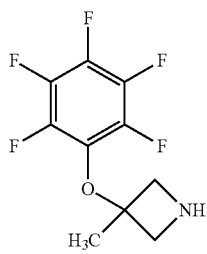 [SMILES: CC1(Oc2c(F)c(F)c(F)c(F)c2F)CNC1]

Prophetic Example 47

1,3-dimethyl-3-(2,3,4,5,6-pentafluorophenoxy)azetidine

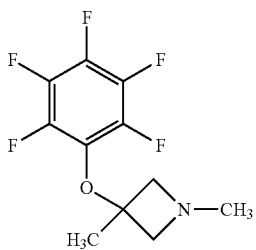 [SMILES: CN1CC(C)(Oc2c(F)c(F)c(F)c(F)c2F)C1]

Prophetic Example 48

1-ethyl-3-methyl-3-(2,3,4,5,6-pentafluorophenoxy)azetidine

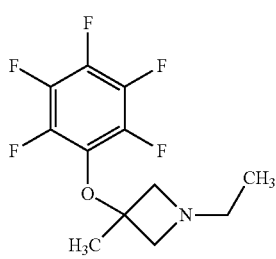 [SMILES: CCN1CC(C)(Oc2c(F)c(F)c(F)c(F)c2F)C1]

Example 49

3-(2,4,6-Trifluorophenoxy)azetidine hydrochloric acid salt

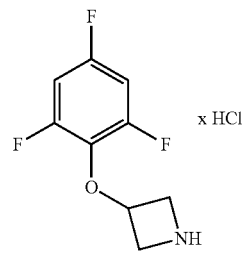 [SMILES: Fc1cc(F)c(OC2CNC2)c(F)c1]

To a solution of tert-butyl 3-(2,4,6-trifluorophenoxy)azetidine-1-carboxylate (Preparation 9) (1.50 g, 4.95 mmol) in DCM (25 mL) was added TFA (3.0 mL, 39 mmol). The solution was stirred for 24 h. The volatiles were removed by evaporation. The residue was co-evaporated with DCM and then partitioned between DCM and an aqueous $Na_2CO_3$ solution (10%). The organic solution was filtered through a phase separator and then concentrated under reduced pressure. The resultant residue, i.e. the non-salt form of 3-(2,4,6-trifluorophenoxy)azetidine, (800 mg) was dissolved in EtOH (20 mL) together with HCl (1.25 M in EtOH, 4 mL). The mixture was stirred for 20 min and then concentrated under reduced pressure. Dropwise to the residue was added diethyl ether (20 mL) and the resultant slurry was stirred at RT for one hour and then the solid was isolated by filtration. The filter cake was dried under vacuum for one hour and then at normal pressure at 70° C. for 2 h. There was obtained 0.55 g (46%) of the title compound as a pale grey solid with a m.p. of 131.5° C. $^1$H NMR (800 Mz, DMSO-$d_6$): δ 4.08 (m, 2H), 4.28 (m, 2H), 4.97 (m, 1H), 7.33 (m, 2H), 9.50 (s, 2H). LC MS m/z 204 [M+H]$^+$.

Example 50

3-(3,4,5-Trifluorophenoxy)azetidine hydrochloric acid salt

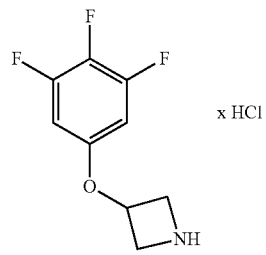 [SMILES: Fc1cc(OC2CNC2)cc(F)c1F]

To a solution of tert-butyl 3-(3,4,5-trifluorophenoxy)azetidine-1-carboxylate (Preparation 10) (0.55 g, 1.81 mmol) in DCM (10 mL) was added TFA (1.5 mL, 20 mmol). The solution was stirred for 24 h. The volatiles were removed by evaporation. The residue was co-evaporated with DCM and then partitioned between DCM and an aqueous $Na_2CO_3$ solution (10%). The organic solution was filtered through a phase separator and then concentrated under reduced pressure. The residue (330 mg) was dissolved in EtOH (10 mL)

together with HCl (1.25 M in EtOH, 2 mL). The mixture was stirred for 20 min and then concentrated under reduced pressure. Dropwise to the residue was added diethyl ether (10 mL) and after one hour the volatiles were again removed by evaporation. Diethyl ether was added drop-wise and the resultant solid was isolated by filtration. The filter cake was dried under vacuum for one hour and then at normal pressure at 70° C. for 2 h. There was obtained 0.22 g (51%) of the title compound as a white solid with a m.p. of 161.9° C. $^1$H NMR (800 Mz, DMSO-d$_6$): δ 3.96 (m, 2H), 4.45 (m, 2H), 5.07 (m, 1H), 6.99 (m, 2H), 9.44 (d, 2H). LC MS m/z 204 [M+H]$^+$.

Example 51

3-(2,4,5-Trifluorophenoxy)azetidine hydrochloric acid salt

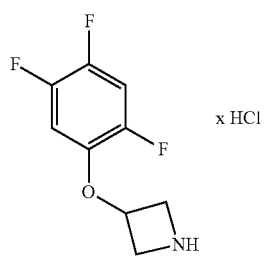 [SMILES: Fc1cc(F)c(OC2CNC2)cc1F]

To a solution of tert-butyl 3-(2,4,5-trifluorophenoxy)azetidine-1-carboxylate (Preparation 11) (0.53 g, 1.75 mmol) in DCM (15 mL) was added TFA (1.5 mL, 20 mmol). The solution was stirred for 24 h. The volatiles were removed by evaporation. The residue was co-evaporated with DCM and then partitioned between DCM and an aqueous Na$_2$CO$_3$ solution (10%). The organic solution was filtered through a phase separator and then concentrated under reduced pressure. The residue (248 mg) was dissolved in EtOH (10 mL) together with HCl (1.25 M in EtOH, 1 mL). The mixture was stirred for 10 min and then concentrated under reduced pressure. Dropwise to the residue was added diethyl ether (10 mL) and after one hour at 0° C. the resultant solid was isolated by filtration. The filter cake was dried under vacuum for one hour and then at normal pressure at 70° C. for 2 h. There was obtained 0.18 g (42%) of the title compound as a white solid with a m.p. of 141.8° C. $^1$H NMR (800 Mz, DMSO-d$_6$): δ 4.01 (m, 2H), 4.44 (m, 2H), 5.11 (m, 1H), 7.33 (dt, 1H), 7.69 (dt, 1H), 9.61 (s, 2H). LC MS m/z 204 [M+H]$^+$.

Example 52A 3-(3,5-difluorophenoxy)azetidine fumaric acid salt

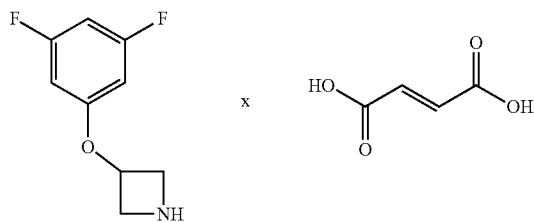 [SMILES: Fc1cc(F)cc(OC2CNC2)c1 ; O=C(O)/C=C/C(=O)O]

To a solution of tert-butyl 3-(3,5-difluorophenoxy)azetidine-1-carboxylate (Preparation 12) (2.38 g, 8.34 mmol) in DCM (40 mL) was added TFA (4 mL, 52 mmol). The solution was stirred over night and the volatiles were removed by evaporation. The residue was partitioned between DCM and an aqueous Na$_2$CO$_3$ solution (10%). The aqueous solution was further extracted with DCM and the combined organic solutions were dried (Na$_2$SO$_4$) and then concentrated under reduced pressure. The residue (1.2 g) was purified by column chromatography on silica-gel using a gradient of MeOH/EtOAc (0-50% MeOH) to provide 0.72 g of the non-salt form of 3-(3,5-difluorophenoxy)azetidine. A part of the residue (0.37 g, 1.98 mmol) was dissolved in MeOH together with fumaric acid (230 mg, 1.98 mmol). The solvent was removed by evaporation and the residue was re-dissolved in MeOH with heating. The evaporation and re-dissolving procedure was repeated once and then the solution was allowed to reach room temperature. Diethyl ether was added drop-wise and the mixture was allowed to stand overnight. The formed solid was isolated by filtration, washed with diethyl ether and then dried in the hood. The material was further dried in an oven at 70° C. for one hour. There was obtained 0.40 g (31%) of the title compound with a m.p. of 154° C. $^1$H NMR (800 Mz, methanol-d$_4$): δ 4.16 (m, 2H), 4.57 (m, 2H), 5.18 (m, 1H), 6.65 (m, 1H), 6.71 (s, 2H). LC MS m/z 115 [M−H]$^−$ and 186 [M+H]$^+$.

Example 52B 3-(3,5-difluorophenoxy)azetidine (+)-tartaric acid salt

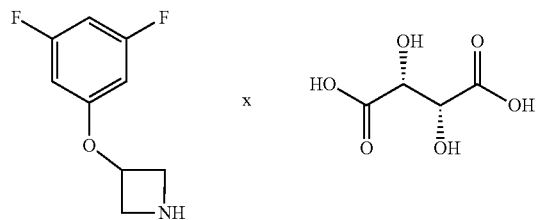 [SMILES: Fc1cc(F)cc(OC2CNC2)c1 ; O=C(O)[C@H](O)[C@@H](O)C(=O)O]

The non-salt form of 3-(3,5-difluorophenoxy)azetidine (0.35 g, 1.90 mmol) that had been obtained from tert-butyl 3-(3,5-difluorophenoxy)azetidine-1-carboxylate (Preparation 12) in a similar fashion as is described in Example 52, was dissolved in MeOH together with (+)-tartaric acid (286 mg, 1.90 mmol). The solvent was removed by evaporation and the residue was re-dissolved in MeOH with heating. The evaporation and re-dissolving procedure was repeated once and then the solution was allowed to reach room temperature. Diethyl ether was added drop-wise and the mixture was allowed to stand overnight. The formed solid was isolated by filtration, washed with diethyl ether and then dried in the hood. The material was further dried in an oven at 70° C. for one hour. There was obtained 200 mg (30%) of the title compound with a m.p. of 153.8° C. $^1$H NMR (800 Mz, DMSO-d$_6$): δ 3.79 (m, 2H), 3.90 (s, 2H), 4.18 (m, 2H), 5.07 (m, 1H), 6.65 (m, 2H), 6.85 (s, 1H). LC MS 186 [M+H]$^+$.

Example 52C

3-(3,5-difluorophenoxy)azetidine hydrochloric acid salt

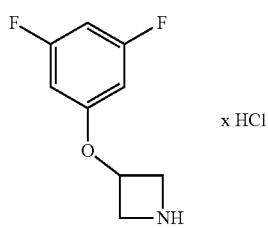 [SMILES: Fc1cc(F)cc(OC2CNC2)c1]

The non-salt form of 3-(3,5-difluorophenoxy)azetidine (1.15 g, 6.18 mmol) that had been obtained from Preparation 12 in a similar fashion as described in Example 52A was dissolved in an EtOH solution of HCl (1.25 M, 10 mL, 12.5 mmol). The volatiles were removed by evaporation and the residue was co-evaporated with EtOH. The residue was re-dissolved in hot EtOH and the resultant solution was allowed to reach room temperature. $Et_2O$ was added dropwise until the solution became cloudy and the mixture was allowed to stand at room temperature overnight. The product was isolated by filtration and the filter-cake was washed with $Et_2O$. After drying in the hood overnight and then in an oven at 70° C. for one hour, there was obtained 0.93 g (67%) of the title compound as a white solid with a m.p. of 161.6° C. LC MS m/z 186 $[M+H]^+$.

Example 53

3-(2,4,6-trifluorophenoxy)-1-ethylazetidine hydrochloric acid salt

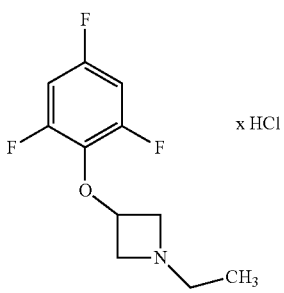 [SMILES: CCN1CC(Oc2c(F)cc(F)cc2F)C1]

The non-salt form of 3-(2,4,6-trifluorophenoxy)azetidine (160 mg, 0.79 mmol) that had been obtained from tert-butyl 3-(2,4,6-trifluorophenoxy)azetidine-1-carboxylate (Preparation 9) in a similar fashion as described in Example 49 was dissolved in dry THF (2 mL). To the solution was added triethylamine (0.4 mL, 2.9 mmol) and iodoethane (0.10 mL, 1.25 mmol). The mixture was stirred for three days and then the volatiles were removed by evaporation. The residue was partitioned between MTBE (20 mL) and an aqueous solution of HCl (10%, 20 mL). The phases were separated and the aqueous solution was pH-adjusted to a pH over 10 by portion-wise addition of solid $Na_2CO_3$. The mixture was extracted with DCM (3×25 mL) and the combined organic solutions were filtered through a phase separator and then evaporated. The residue was purified by column chromatography on silica-gel using a gradient of MeOH/EtOAc (0-15% MeOH) to provide the non-salt form of the title compound as an oil (40 mg). The residue was dissolved in ethanol (2 mL) and to the resulting solution was added an ethanol solution of HCl (1.2M, 0.3 mL, 0.36 mmol). The mixture was stirred for 10 min and then concentrated. Diethyl ether (2 mL) was added to the residue and after cooling with an ice-bath for one hour the product was isolated by decantation. The crystals were dried in vacuo for 30 min and then in an oven at 70° C. for 2 h. There was obtained 39 mg (18%) of title compound as a white solid with a m.p. of 134.1° C. $^1$H NMR (800 Mz, DMSO-$d_6$): δ 1.13 (t, 3H), 3.25 (m, 2H), 4.18 (s, 2H), 4.43 (s, 2H), 4.95 (m, 1H), 7.34 (m, 2H), 11.10 (s, 1H). LC MS m/z 232 $[M+H]^+$.

Example 54

3-(2,3,6-trifluorophenoxy)-1-propylazetidine

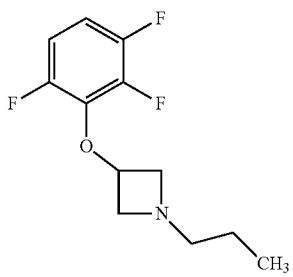 [SMILES: CCCN1CC(Oc2c(F)ccc(F)c2F)C1]

The non-salt form of 3-(2,3,6-difluorophenoxy)azetidine (0.20 g, 0.98 mmol) that had been obtained from tert-butyl 3-(2,3,6-trifluorophenoxy)azetidine-1-carboxylate (Preparation 6) in a similar fashion as described in Example 20 was dissolved in 1,2-dichloroethane (10 mL), together with acetic acid (0.11 mL, 2.0 mmol) and propionaldehyde (0.21 mL, 2.9 mmol). The mixture was stirred for 15 min at room temperature and then sodium triacetoxyborohydride (625 mg, 2.95 mmol) was added portion-wise. The mixture was stirred over night and then an aqueous solution of $Na_2CO_3$ (10%) was added. After extracting with DCM, the organic solution was dried ($Na_2SO_4$) and the volatiles were removed by evaporation. The residue (0.31 g) was purified by column chromatography on silica-gel using a gradient of MeOH/EtOAc (0-50% MeOH) to provide 27 mg (11%) of a contaminated preparation of the non-salt form of 3-(2,3,6-trifluorophenoxy)-1-propylazetidine. GC MS m/z (relative intensity, 70 eV). 246 (2), 245 (9), 244 (3), 217 (12), 216 (bp), 175 (5), 174 (44), 161 (3), 155 (3), 154 (7), 149 (4), 148 (52), 147 (8), 146 (8), 145 (31), 131 (3), 128 (3), 127 (3), 126 (4), 119 (18), 108 (6), 101 (2), 100 (16), 99 (10), 98 (50), 96 (2), 93 (2), 85 (14), 84 (13), 81 (7), 75 (3), 71 (4), 70 (44), 69 (10), 68 (13), 57 (3), 56 (8), 55 (4), 54 (4), 50 (2).

Example 55

3-(3,5-difluorophenoxy)-1-methylazetidine

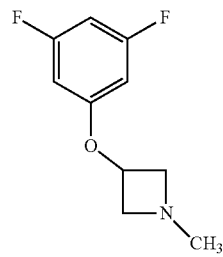

The non-salt form of 3-(3,5-difluorophenoxy)azetidine (0.30 g, 1.62 mmol) that had been obtained from Preparation 12 in a similar fashion as described in Example 52A was dissolved in dry DCM (10 mL) together with acetic acid (0.19 mL, 3.24 mmol). To the solution was added an aqueous solution of formaldehyde (37%, 0.36 mL, 4.86 mmol) and the mixture was stirred for 15 min at room temperature. Sodium triacetoxyborohydride (1.0 g, 4.86 mmol) was added portion-wise and the mixture was stirred for one hour. An aqueous solution of $Na_2CO_3$ (10%) was added and the mixture was extracted with DCM. The organic solution was dried ($Na_2SO_4$) and then the volatiles were removed by evaporation. The residue (0.29 g) was purified by column chromatography on silica-gel using a gradient of MeOH/EtOAc (0-50% MeOH) to provide 126 mg (39%) of the non-salt form of 3-(3,5-difluorophenoxy)-1-methylazetidine. GC MS m/z (relative intensity, 70 eV). 200 (2), 199 (15), 157 (9), 156 (95), 155 (11), 137 (3), 136 (4), 131 (2), 130 (32), 128 (20), 127 (bp), 115 (2), 114 (4), 113 (6), 109 (4), 108 (3), 102 (9), 101 (10), 99 (1), 94 (1), 93 (1), 82 (3), 81 (3), 75 (3), 70 (7), 68 (5), 63 (7), 58 (3), 57 (4), 52 (1), 51 (2).

Prophetic Example 56

3-(3,5-difluorophenoxy)-1-ethylazetidine

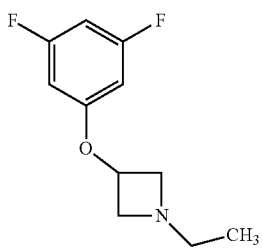

Prophetic Example 57

3-(3,5-difluorophenoxy)-3-methylazetidine

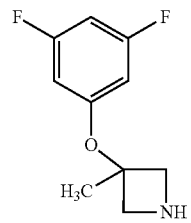

Prophetic Example 58

3-(3,5-difluorophenoxy)-1,3-dimethylazetidine

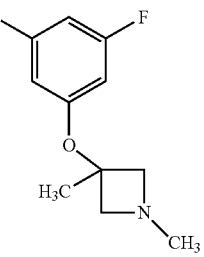

Prophetic Example 59

3-(3,5-difluorophenoxy)-1-ethyl-3-methylazetidine

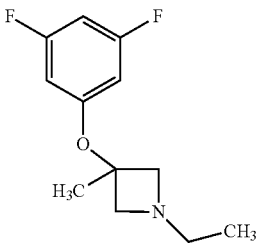 [SMILES: CCN1CC(C)(Oc2cc(F)cc(F)c2)C1]

Example 60

3-(2,3-difluorophenoxy)-1-($^2H_3$)methylazetidine

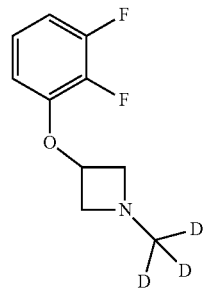 [SMILES: [2H]C([2H])([2H])N1CC(Oc2cccc(F)c2F)C1]

The non-salt form of 3-(2,3-difluorophenoxy)azetidine (0.35 g, 1.89 mmol) that had been obtained from Preparation 1 in a similar fashion as described in Example 1A, was dissolved in dry THF (10 mL). To the resultant solution was added triethylamine (0.8 mL, 5.75 mmol) and iodomethane-$d_3$ (0.12 mL, 2.00 mmol) in the given order. The mixture was stirred over night, diluted with EtOAc and then washed with an aqueous solution of $Na_2CO_3$ (10%). The organic solution was dried ($Na_2SO_4$) and the volatiles removed by evaporation. The residue was purified by column chromatography on silica-gel using a gradient of MeOH/EtOAc (0-35% MeOH) to provide 159 mg of a contaminated preparation of the non-salt form of 3-(2,3-difluorophenoxy)-1-($^2H_3$)methylazetidine. GC MS m/z (relative intensity, 70 eV). 202 (6), 157 (8), 156 (bp), 155 (14), 138 (2), 137 (18), 136 (20), 131 (5), 130 (75), 128 (15), 127 (80), 113 (6), 110 (3), 109 (6), 108 (13), 102 (4), 101 (15), 82 (11), 81 (4), 75 (7), 73 (21), 71 (5), 63 (10), 60 (6), 57 (3), 51 (3).

Prophetic Example 61

3-(2,3-difluorophenoxy)-1-[(1,1,2,2,2-$^2H_5$)ethyl]azetidine

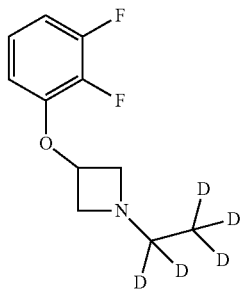 [SMILES: [2H]C([2H])([2H])C([2H])([2H])N1CC(Oc2cccc(F)c2F)C1]

Prophetic Example 62

3-(2,3-difluorophenoxy)(3-$^2H$)azetidine

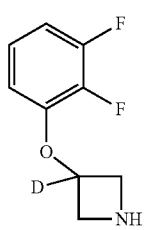 [SMILES: [2H]C1(Oc2cccc(F)c2F)CNC1]

Prophetic Example 63

3-(2,3-difluorophenoxy)(2,2,4,4-$^2H_4$)azetidine

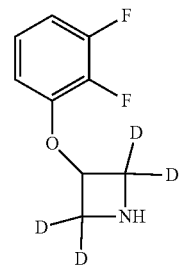 [SMILES: [2H]C1([2H])NC([2H])([2H])C1Oc1cccc(F)c1F]

Prophetic Example 64

3-(2,3-difluorophenoxy)(2,2,3,4,4-$^2H_5$)azetidine

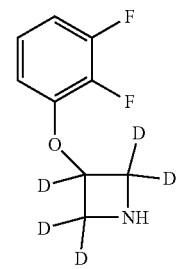 [SMILES: [2H]C1([2H])NC([2H])([2H])C1([2H])Oc1cccc(F)c1F]

Prophetic Example 65

3-[2,3-difluoro(4,6-$^2H_2$)phenoxy]azetidine

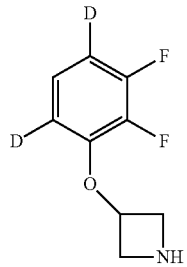

59

Prophetic Example 66

3-[2,3-difluoro(4,6-$^2H_2$)phenoxy](3-$^2H$)azetidine

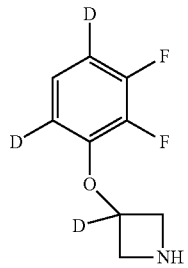 [SMILES: [2H]c1cc([2H])c(OC2([2H])CNC2)c(F)c1F]

Prophetic Example 67

3-[2,3-difluoro(4,6-$^2H_2$)phenoxy](2,2,4,4-$^2H_4$)azetidine

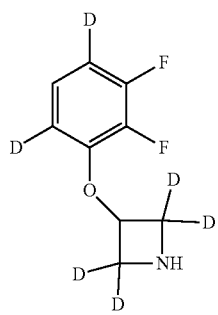 [SMILES: [2H]c1cc([2H])c(OC2C([2H])([2H])NC2([2H])[2H])c(F)c1F]

Prophetic Example 68

3-[2,3-difluoro(4,6-$^2H_2$)phenoxy](2,2,3,4,4-$^2H_5$)azetidine

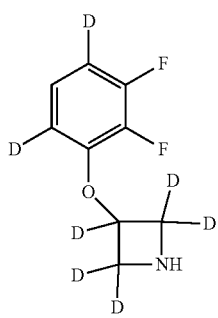 [SMILES: [2H]c1cc([2H])c(OC2([2H])C([2H])([2H])NC2([2H])[2H])c(F)c1F]

60

Example 69

3-(3,5-difluorophenoxy)-1-($^2H_3$)methylazetidine

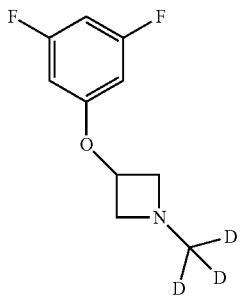 [SMILES: [2H]C([2H])([2H])N1CC(Oc2cc(F)cc(F)c2)C1]

The non-salt form of 3-(3,5-difluorophenoxy)azetidine (0.30 g, 1.62 mmol) that had been obtained from Preparation 12 in a similar fashion as described in Example 52A, was dissolved in dry THF (10 mL). To the resultant solution was added triethylamine (0.67 mL, 4.86 mmol) and iodomethane-d$_3$ (0.11 mL, 1.78 mmol) in the given order. The mixture was stirred over night and then diluted with EtOAc. The solution was washed with an aqueous solution of Na$_2$CO$_3$ (10%), dried (Na$_2$SO$_4$) and then the volatiles were removed by evaporation. The residue (0.31 g) was purified by column chromatography on silica-gel using a gradient of MeOH/EtOAc (0-50% MeOH) to provide 60 mg of a contaminated preparation of the non-salt form of 3-(3,5-difluorophenoxy)-1-($^2H_3$)methylazetidine. GC MS m/z (relative intensity, 70 eV). 203 (2), 202 (14), 157 (8), 156 (87), 155 (9), 137 (3), 136 (4), 131 (2), 130 (32), 127 (bp), 115 (2), 114 (4), 113 (7), 109 (4), 108 (3), 102 (9), 101 (11), 82 (2), 81 (3), 75 (3), 73 (7), 71 (4), 63 (8), 61 (4), 60 (2), 57 (3), 51 (2).

Prophetic Example 70

3-(3,5-difluorophenoxy)-1-[(1,1,2,2,2-$^2H_5$)ethyl]azetidine

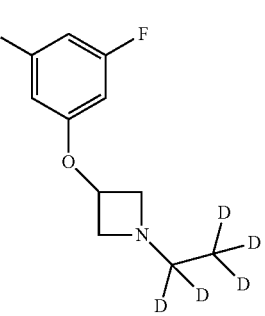

Prophetic Example 71

3-(3,5-difluorophenoxy)(3-²H)azetidine

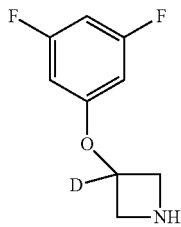 [SMILES: [2H]C1(Oc2cc(F)cc(F)c2)CNC1]

Prophetic Example 72

3-(3,5-difluorophenoxy)(2,2,4,4-²H₄)azetidine

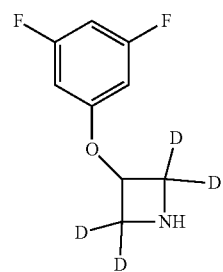 [SMILES: [2H]C1([2H])NC([2H])([2H])C1Oc1cc(F)cc(F)c1]

Prophetic Example 73

3-(3,5-difluorophenoxy)(2,2,3,4,4-²H₅)azetidine

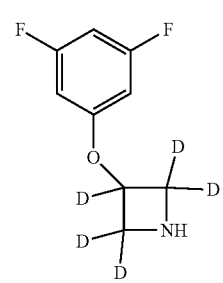 [SMILES: [2H]C1([2H])NC([2H])([2H])C1([2H])Oc1cc(F)cc(F)c1]

Example 74

3-[3,5-difluoro(2,4,6-²H₃)phenoxy]azetidine oxalic acid salt

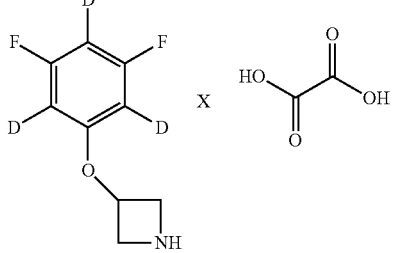

To a solution of tert-butyl 3-[3,5-difluoro(2,4,6-²H₃)phenoxy]azetidine-1-carboxylate (Preparation 13) (30 mg, 0.10 mmol) in DCM (1 mL) was added TFA (0.2 mL, 2.6 mmol). The solution was stirred for 16 h. The volatiles were removed by evaporation and the residue was partitioned between DCM and an aqueous solution of Na₂CO₃ (10%). The aqueous solution was extracted with DCM and the combined organic solutions were filtered through a phase-separator. Evaporation provided the title compound in non-salt form (10 mg). The residue was mixed with ethanol (1 mL) and oxalic acid dihydrate (7 mg, 0.055 mmol). After a couple of minutes, a precipitation was formed and to the suspension was slowly added diethyl ether (1 mL). The mixture was stirred with cooling for one hour and then the solid was isolated by decantation. After drying in vacuum and then in an oven at 70° C., there was obtained 11 mg (38%) of the title compound as a white solid with a m.p. of 177.2° C. ¹H NMR (800 Mz, DMSO-d₆): δ 3.16 (s, 2H), 3.98 (m, 2H), 4.44 (m, 2H), 5.09 (m, 1H) as well as traces at 6.70 (d) and 6.89 (t). LC MS m/z 188 [M+H]+ and 189 [M+H]⁺ in the ratio 4:10.

Prophetic Example 75

3-[3,5-difluoro(2,4,6-²H₃)phenoxy](3-²H)azetidine

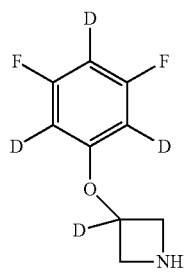

63

Prophetic Example 76

3-[3,5-difluoro(2,4,6-$^2$H$_3$)phenoxy](2,2,4,4-$^2$H$_4$)azetidine

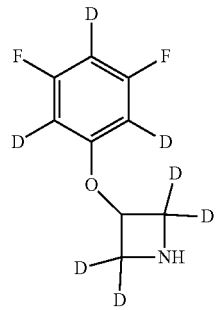

Prophetic Example 77

3-[3,5-difluoro(2,4,6-$^2$H$_3$)phenoxy](2,2,3,4,4-$^2$H$_5$)azetidine

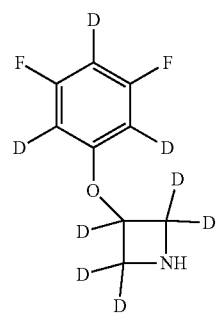 [SMILES: [2H]c1c(F)c([2H])c(OC2([2H])C([2H])([2H])NC2([2H])[2H])c([2H])c1F]

Prophetic Example 78

1-($^2$H$_3$)methyl-3-(2,3,5,6-tetrafluorophenoxy)azetidine

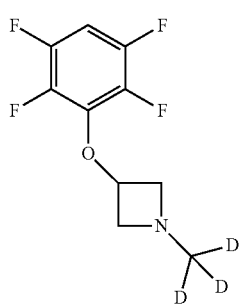 [SMILES: [2H]C([2H])([2H])N1CC(Oc2c(F)c(F)cc(F)c2F)C1]

64

Prophetic Example 79

1-[(1,1,2,2,2-$^2$H$_5$)ethyl]-3-(2,3,5,6-tetrafluorophenoxy)azetidine

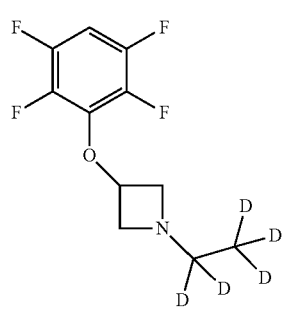 [SMILES: [2H]C([2H])([2H])C([2H])([2H])N1CC(Oc2c(F)c(F)cc(F)c2F)C1]

Prophetic Example 80

3-(2,3,5,6-tetrafluorophenoxy)(3-$^2$H)azetidine

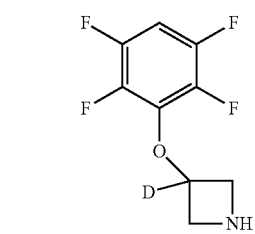

Prophetic Example 81

3-(2,3,5,6-tetrafluorophenoxy)(2,2,4,4-$^2$H$_4$)azetidine

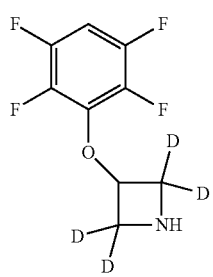

Prophetic Example 82
3-(2,3,5,6-tetrafluorophenoxy)(2,2,3,4,4-²H₅)azetidine
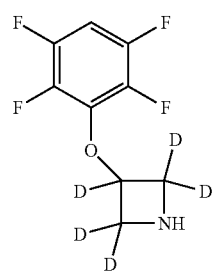 [SMILES: [2H]C1([2H])NC([2H])([2H])C1([2H])Oc1c(F)c(F)cc(F)c1F]
Prophetic Example 83
3-[2,3,5,6-tetrafluoro(4-²H)phenoxy]azetidine
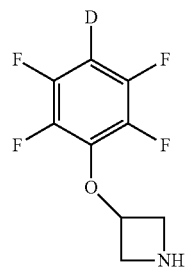 [SMILES: [2H]c1c(F)c(F)c(OC2CNC2)c(F)c1F]
Prophetic Example 84
3-[2,3,5,6-tetrafluoro(4-²H)phenoxy](3-²H)azetidine
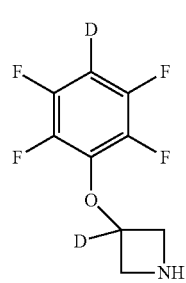 [SMILES: [2H]c1c(F)c(F)c(OC2([2H])CNC2)c(F)c1F]
Prophetic Example 85
3-[2,3,5,6-tetrafluoro(4-²H)phenoxy](2,2,4,4-²H₄)azetidine
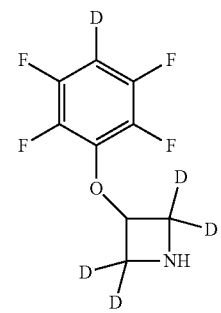
Prophetic Example 86
3-[2,3,5,6-tetrafluoro(4-²H)phenoxy](2,2,3,4,4-²H₅)azetidine
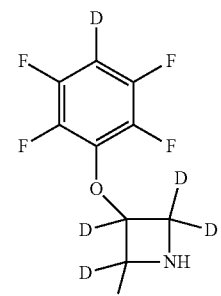
Prophetic Example 87
1-(²H₃)methyl-3-(2,3,6-trifluorophenoxy)azetidine
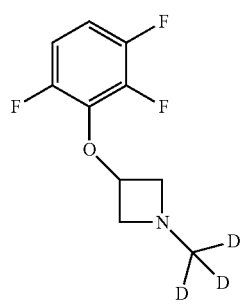 [SMILES: [2H]C([2H])([2H])N1CC(Oc2c(F)ccc(F)c2F)C1]

Example 88

1-[(1,1,2,2,2-²H₅)ethyl]-3-(2,3,6-trifluorophenoxy)azetidine oxalic acid salt

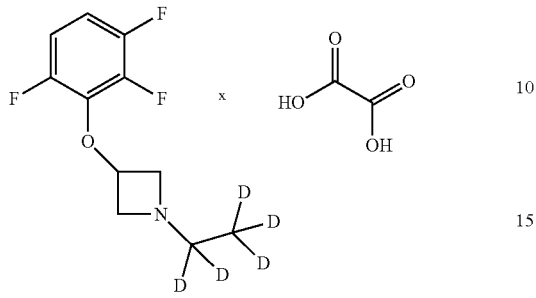

The non-salt form of 3-(2,3,6-trifluorophenoxy)azetidine (0.500 g, 2.46 mmol) that had been obtained from Preparation 6 in a similar fashion as described in Example 20 was dissolved in dry THF (10 mL). To the resultant solution was added triethylamine (1.0 mL, 7.38 mmol) and iodoethane-d₅ (0.25 mL, 3.2 mmol). The mixture was stirred for 22 h and then the volatiles were removed by evaporation. The residue was partitioned between MTBE (20 mL) and an aqueous solution of HCl (10%, 20 mL). The phases were separated and the aqueous solution was pH-adjusted to a pH over 10 by portion-wise addition of solid Na₂CO₃. The mixture was extracted with DCM (3×25 mL) and the combined organic solutions were dried (Na₂SO₄) and evaporated. The residue was purified by column chromatography on silica-gel using a gradient of MeOH/EtOAc (0-20% MeOH) to provide the non-salt form of the title compound as an oil (0.31 g). The residue was dissolved in ethanol and to the resulting solution was added oxalic acid dihydrate dissolved in EtOH (165 mg, 1.31 mmol). The mixture was concentrated and the residue was dissolved in hot methanol. After cooling to room temperature, diethyl ether was added drop-wise until the mixture became cloudy. On allowing to stand overnight a precipitate formed that was isolated by filtration. The crystals were washed with ether, air-dried in the hood and then in an oven at 70° C. for one hour. There was obtained 0.28 g (35%) of title compound as a white solid with a m.p. of 155.2° C. ¹H NMR (800 Mz, methanol-d₄): δ 4.37 (s, 2H), 4.62 (s, 2H), 5.15 (m, 1H), 7.09 (m, 2H). LC MS m/z 237 [M+H]⁺.

Prophetic Example 89

3-(2,3,6-trifluorophenoxy)(3-²H)azetidine

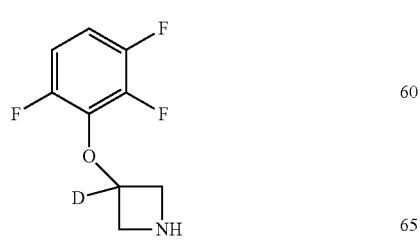

Prophetic Example 90

3-(2,3,6-trifluorophenoxy)(2,2,4,4-²H₄)azetidine

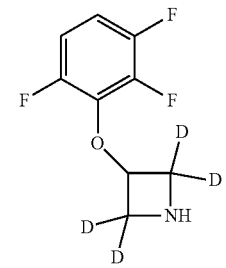 [SMILES: [2H]C1([2H])NC([2H])([2H])C1Oc1c(F)ccc(F)c1F]

Prophetic Example 91

3-(2,3,6-trifluorophenoxy)(2,2,3,4,4-²H₅)azetidine

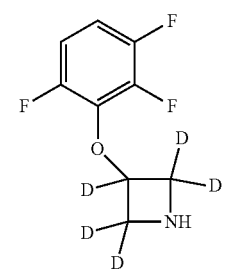 [SMILES: [2H]C1([2H])NC([2H])([2H])C1([2H])Oc1c(F)ccc(F)c1F]

Prophetic Example 92

3-[2,3,6-trifluoro(4-²H)phenoxy]azetidine

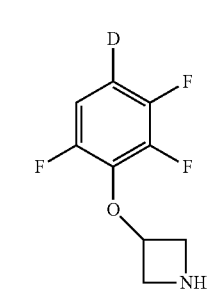

Prophetic Example 93
3[2,3,6-trifluoro(4-²H)phenoxy](3-²H)azetidine
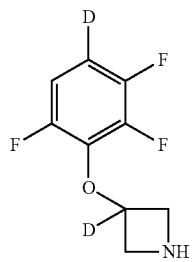
Prophetic Example 94
3[2,3,6-trifluoro(4-²H)phenoxy](2,2,4,4-²H₄)azetidine
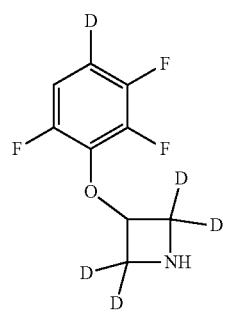
Prophetic Example 95
3[2,3,6-trifluoro(4-²H)phenoxy](2,2,3,4,4-²H₅)azetidine
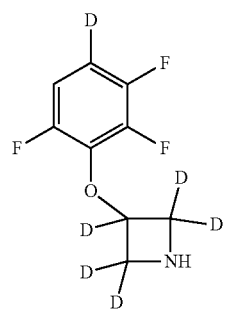
Prophetic Example 96
1-(²H₃)methyl-3-(2,3,5-trifluorophenoxy)azetidine
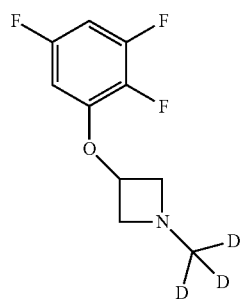 [SMILES: [2H]C([2H])([2H])N1CC(Oc2cc(F)cc(F)c2F)C1]
Prophetic Example 97
1-[(1,1,2,2,2-²H₅)ethyl]-3-(2,3,5-trifluorophenoxy)azetidine
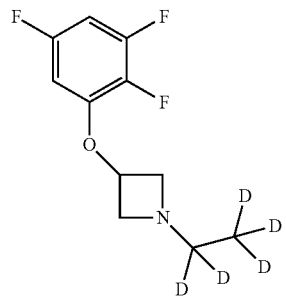 [SMILES: [2H]C([2H])([2H])C([2H])([2H])N1CC(Oc2cc(F)cc(F)c2F)C1]
Prophetic Example 98
3-(2,3,5-trifluorophenoxy)(3-²H)azetidine
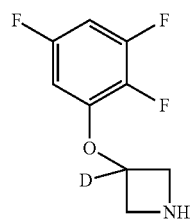 [SMILES: [2H]C1(Oc2cc(F)cc(F)c2F)CNC1]

Prophetic Example 99

3-(2,3,5-trifluorophenoxy)(2,2,4,4-$^2$H$_4$)azetidine

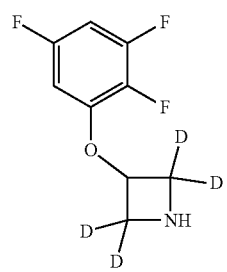

Prophetic Example 100

3-(2,3,5-trifluorophenoxy)(2,2,3,4,4-$^2$H$_5$)azetidine

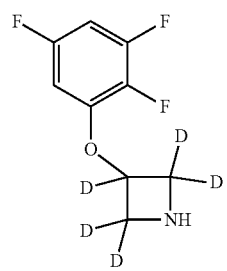

Prophetic Example 101

3-[2,3,5-trifluoro(4,6-$^2$H$_2$)phenoxy]azetidine

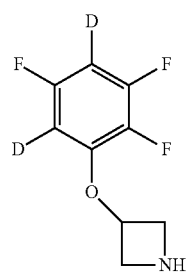

Prophetic Example 102

3-[2,3,5-trifluoro(4,6-$^2$H$_2$)phenoxy](3-$^2$H)azetidine

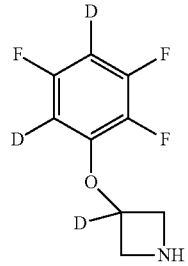

Prophetic Example 103

3-[2,3,5-trifluoro(4,6-$^2$H$_2$)phenoxy](2,2,4,4-$^2$H$_4$) azetidine

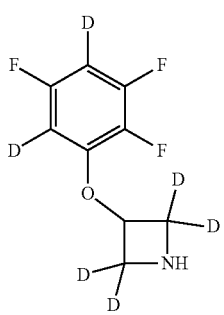

Prophetic Example 104

3-[2,3,5-trifluoro(4,6-$^2$H$_2$)phenoxy](2,2,3,4,4-$^2$H$_5$) azetidine

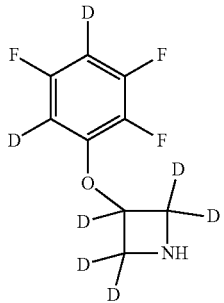

Preparation 1

TERT-BUTYL 3-(2,3-DIFLUOROPHENOXY)AZETIDINE-1-CARBOXYLATE (Intermediate to Example 1A and Example 1B)

Triphenylphosphine (7.11 g, 27.1 mmol) was dissolved in dry THF (100 mL) and the solution was flushed with nitrogen for 10 min. DEAD (10.8 g, 24.9 mmol) was added dropwise (5 min) whereupon tert-butyl 3-hydroxyazetidine-1-carboxylate (3.99 g, 22.6 mmol) and 2,3-difluorophenol (3.00 g, 22.6 mmol) were added in small portions in the given order. The reaction mixture was stirred at 70° C. for 20 h and then partitioned between water and MTBE. The aqueous solution was extracted with another portion of MTBE and the combined organic solutions were washed with aqueous KOH (10%), water and with brine. After drying ($Na_2SO_4$) and filtration, the volatiles were removed by evaporation. Purification by chromatography on silica gel eluting with a mixture of isooctane and EtOAc (gradient, 30-100% EtOAc) provided 5.9 g (91%) of the title compound. $^1$H NMR (400 Mz, methanol-$d_4$): δ 1.49 (s, 9H), 3.99 (m, 2H), 4.38 (m, 2H), 5.07 (m, 1H), 6.70 (m, 1H), 6.92 (m, 1H), 7.09 (m, 1H).

Preparation 2

TERT-BUTYL 3-(2,3,5-TRIFLUOROPHENOXY)AZETIDINE-1-CARBOXYLATE (Intermediate to Example 2)

A mixture of tert-butyl 3-(methanesulfonyloxy)azetidine-1-carboxylate (1.00 g, 3.98 mmol), 2,3,5,-trifluorophenol (0.60 g, 4.00 mmol) and $Cs_2CO_3$ (1.55 g, 4.78 mmol) in DMF (30 mL) was stirred at 110° C. for 24 h. After cooling to room temperature, the mixture was filtered and the solvent removed by evaporation. The residue was dissolved in EtOAc (75 mL) and the solution washed with water (3×50 mL), dried ($Na_2SO_4$) and evaporated. Purification by chromatography on silica gel eluting with a mixture of isooctane and EtOAc (gradient, 0-17% EtOAc) provided 0.80 g (66%) of the title compound as an oil. GC MS m/z (relative intensity, 70 eV) 354 (5), 281 (6), 247 (22), 230 (6), 207 (24), 203 (6), 175 (5), 174 (46), 161 (9), 154 (6), 148 (20), 145 (11), 126 (7), 119 (7), 100 (6), 82 (11), 81 (6), 73 (7), 58 (6), 57 (bp), 56 (16), 55 (7), 54 (5).

Preparation 3

TERT-BUTYL 3-(2,3,5,6-TETRAFLUOROPHENOXY)AZETIDINE-1-CARBOXYLATE (Intermediate to Example 3)

A mixture of tert-butyl 3-(methanesulfonyloxy)azetidine-1-carboxylate (1.00 g, 3.98 mmol), 2,3,5,6-tetrafluorophenol (0.65 g, 3.91 mmol) and $Cs_2CO_3$ (1.55 g, 4.78 mmol) in DMF (30 mL) was stirred at 110° C. for 20 h. After cooling to room temperature, the mixture was filtered and the solvent of the filtrate removed by evaporation. The residue was dissolved in EtOAc (75 mL) and the solution washed with water (3×50 mL), dried ($Na_2SO_4$) and evaporated. Purification by chromatography on silica gel eluting with a mixture of isooctane and EtOAc (gradient, 0-17% EtOAc) provided 0.60 g (47%) of the title compound. GC MS m/z (relative intensity, 70 eV) 266 (5), 265 (13), 248 (16), 221 (6), 207 (15), 192 (28), 179 (8), 172 (5), 166 (21), 163 (7), 149 (5), 118 (9), 99 (8), 82 (8), 58 (7), 57 (bp), 56 (28), 55 (12), 54 (9).

Preparation 4

1-(DIPHENYLMETHYL)-3-METHYL-3-(2,3,5-TRIFLUOROPHENOXY)AZETIDINE (Intermediate to Example 4)

A mixture of 2,3,5-trifluorophenol (0.65 g, 4.39 mmol) and triphenyl phosphine (1.30 g, 5.00 mmol) in toluene (16 mL) was heated to 95° C. A solution of 1-(diphenylmethyl)-3-methylazetidin-3-ol—for preparation, see US 2006/0160786—(1.00 g, 3.94 mmol) and diisopropyl azodicarboxylate (1.00 mL, 5.08 mmol) in toluene (10 mL) was added dropwise at 95° C. during a period of 15 min. The mixture was stirred at 95° C. for 4 h and then at 80° C. overnight. The volatiles were removed by evaporation and the residue purified by chromatography on silica gel using a mixture of isooctane and EtOAc as eluent (gradient, 0-50% EtOAc). There was obtained 1.30 g (86%) of the title compound as an oil. LC MS m/z 384 [M+H]+, GC MS m/z (relative intensity, 70 eV) 236 (6), 208 (4), 207 (10), 168 (15), 167 (bp), 166 (12), 165 (27), 152 (13), 148 (9), 119 (5), 91 (6), 77 (4), 69 (4).

Preparation 5 (Intermediate to Example 10)

tert-Butyl 3-(2,3,4-trifluorophenoxy)azetidine-1-carboxylate 2,3,4-Trifluorophenol (0.68 g, 4.6 mmol) was dissolved in DCM (20 mL) together with tert-butyl 3-hydroxyazetidine-1-carboxylate (1.00 g, 5.8 mmol) and triphenyl phosphine (1.6 g, 6.1 mmol). Diisopropyl azodicarboxylate (1.2 mL, 6.1 mmol) was then added dropwise to the resultant solution at 0° C. The mixture was stirred with cooling for one hour and then at RT for 20 h. After dilution with DCM, the solution was washed with brine, dried over $Na_2SO_4$ and then concentrated under reduced pressure. The resulting residue was purified by column chromatography on silica-gel using a gradient of isooctane/EtOAc (0-18% EtOAc) to provide 0.66 g (48%) of the title compound as an oil. GC MS m/z (relative intensity, 70 eV). 355 (5), 354 (6), 352 (4), 281 (11), 247 (19), 230 (15), 207 (33), 175 (9), 174 (bp), 148 (70), 147 (15), 145 (36), 119 (13), 100 (30), 99 (9), 81 (15), 57 (68), 56 (28), 55 (11), 54 (11).

Preparation 6 (Intermediate to Example 20)

tert-Butyl 3-(2,3,6-trifluorophenoxy)azetidine-1-carboxylate 2,3,6-Trifluorophenol (0.95 g, 6.4 mmol) was dissolved in DCM (25 mL) together with tert-butyl 3-hydroxyazetidine-1-carboxylate (1.45 g, 8.4 mmol) and triphenyl phosphine (2.2 g, 8.4 mmol). Diisopropyl azodicarboxylate (1.7 mL, 8.6 mmol) was then added dropwise to the resultant solution at 0° C. The mixture was stirred with cooling for one hour and then at RT for three days. After dilution with DCM, the solution was washed with brine, dried over $Na_2SO_4$ and then concentrated under reduced pressure. The resulting residue was purified by column chromatography on silica-gel using a gradient of isooctane/EtOAc (0-17% EtOAc) to provide 1.40 g (72%) of the title compound as an oil. $^1$H NMR (800 Mz, $CDCl_3$): δ 1.46 (s, 9H), 4.12 (m, 2H), 4.23 (m, 2H), 4.97 (m, 1H), 6.85 (m, 2H).

Preparation 7 (Intermediate to Example 38 and Example 39 Using a Synthesis Analogous to the One Described for Example 3)

3-(2,3,5,6-tetrafluorophenoxy)azetidine

To a solution of tert-butyl 3-(2,3,5,6-tetrafluorophenoxy)azetidine-1-carboxylate (1.40 g, 4.36 mmol) in DCM (25 mL) was added TFA (4 mL, 20 mmol). The solution was stirred for 16 h. The volatiles were removed by evaporation.

The residue was co-evaporated with DCM and then partitioned between DCM and an aqueous Na$_2$CO$_3$ solution (10%). The aqueous solution was extracted with DCM and the combined organic extracts were filtered through a phase separator and evaporated. There was obtained 0.85 g (88%) of the title compound as an oil that gradually crystallized. LC MS m/z 222 [M+H]$^+$.

Preparation 8 (Intermediate to Example 43)

tert-Butyl 3-(2,3,4,5,6-pentafluorophenoxy)azetidine-1-carboxylate 2,3,4,5,6-Pentafluorophenol (1.38 g, 7.5 mmol) was dissolved in DCM (30 mL) together with tert-butyl 3-hydroxyazetidine-1-carboxylate (1.68 g, 9.7 mmol) and triphenyl phosphine (2.6 g, 9.7 mmol). Diisopropyl azodicarboxylate (1.9 mL, 9.7 mmol) was then added dropwise to the resultant solution at 0° C. The mixture was stirred with cooling for one hour and then at RT for 20 h. After dilution with DCM, the solution was washed with brine, dried over Na$_2$SO$_4$ and then concentrated under reduced pressure. The resulting residue was purified by column chromatography on silica-gel using a gradient of isooctane/EtOAc (0-16% EtOAc) to provide 2.16 g (85%) of the title compound as an oil that gradually crystallized. $^1$H NMR (800 Mz, CDCl$_3$): δ 1.46 (s, 9H), 4.11 (m, 2H), 4.24 (m, 2H), 4.93 (m, 1H).

Preparation 9 (Intermediate to Example 49)

tert-Butyl 3-(2,4,6-trifluorophenoxy)azetidine-1-carboxylate 2,4,6-Trifluorophenol (0.91 g, 6.1 mmol) was dissolved in DCM (20 mL) together with tert-butyl 3-hydroxyazetidine-1-carboxylate (1.40 g, 8.1 mmol) and triphenyl phosphine (2.1 g, 8.0 mmol). Diisopropyl azodicarboxylate (1.6 mL, 7.9 mmol) was then added dropwise to the resultant solution at 0° C. The mixture was stirred with cooling for one hour and then at RT for 20 h. After dilution with DCM, the solution was washed with brine, dried over Na$_2$SO$_4$ and then concentrated under reduced pressure. The resulting residue was purified by column chromatography on silica-gel using a gradient of isooctane/EtOAc (0-18% EtOAc) to provide 1.5 g (80%) of the title compound as an oil. GC MS m/z (relative intensity, 70 eV). 354 (9), 281 (11), 247 (19), 230 (15), 207 (33), 175 (9), 174 (bp), 148 (70), 147 (15), 145 (36), 119 (13), 100 (30), 99 (9), 81 (15), 57 (68), 56 (28), 55 (11), 54 (11).

Preparation 10 (Intermediate to Example 50)

tert-Butyl 3-(3,4,5-trifluorophenoxy)azetidine-1-carboxylate 3,4,5-Trifluorophenol (0.85 g, 5.7 mmol) was dissolved in DCM (20 mL) together with tert-butyl 3-hydroxyazetidine-1-carboxylate (1.30 g, 7.5 mmol) and triphenyl phosphine (2.0 g, 7.6 mmol). Diisopropyl azodicarboxylate (1.5 mL, 7.6 mmol) was then added dropwise to the resultant solution at 0° C. The mixture was stirred with cooling for one hour and then at RT for 20 h. After dilution with DCM, the solution was washed with brine, dried over Na$_2$SO$_4$ and then concentrated under reduced pressure. The resulting residue was purified by column chromatography on silica-gel using a gradient of isooctane/EtOAc (0-22% EtOAc) to provide 0.55 g (32%) of the title compound as a yellow oil. GC MS m/z (relative intensity, 70 eV). 354 (7), 352 (7), 247 (5), 207 (24), 186 (9), 175 (11), 174 (bp), 161 (5), 154 (8), 148 (65), 145 (46), 141 (5), 139 (5), 131 (11), 128 (7), 127 (7), 126 (6), 125 (5), 120 (20), 119 (28), 110 (6), 102 (5), 101 (7), 99 (8), 98 (5), 94 (6), 91 (9), 82 (8), 81 (14), 79 (5) 78 (7), 77 (7), 76 (6), 75 (16), 74 (8), 71 (6), 70 (8), 69 (6), 68 (7), 65 (7), 63 (8), 57 (44), 56 (13), 55 (8), 54 (9), 51 (13).

Preparation 11 (Intermediate to Example 51)

tert-Butyl 3-(2,4,5-trifluorophenoxy)azetidine-1-carboxylate 2,4,5-Trifluorophenol (0.53 g, 3.6 mmol) was dissolved in DCM (20 mL) together with tert-butyl 3-hydroxyazetidine-1-carboxylate (0.80 g, 4.6 mmol) and triphenyl phosphine (1.25 g, 4.8 mmol). Diisopropyl azodicarboxylate (0.9 mL, 4.6 mmol) was then added dropwise to the resultant solution at 0° C. The mixture was stirred with cooling for one hour and then at RT for 20 h. After dilution with DCM, the solution was washed with brine, dried over Na$_2$SO$_4$ and then concentrated under reduced pressure. The resulting residue was purified by column chromatography on silica-gel using a gradient of isooctane/EtOAc (0-18% EtOAc) to provide 0.53 g (49%) of the title compound as an oil. GC MS m/z (relative intensity, 70 eV). 354 (3), 352 (5), 281 (5), 278 (3), 269 (3), 255 (3), 253 (5), 253 (5), 247 (9), 230 (8), 209 (3), 207 (20), 191 (4), 175 (11), 174 (bp), 167 (4), 161 (6), 156 (6), 155 (3), 154 (3), 149 (7), 148 (69), 146 (5), 145 (29), 130 (3), 128 (7), 127 (3), 126 (8), 120 (6), 119 (13), 115 (3), 111 (4), 101 (5), 100 (18), 99 (8), 98 (3), 91 (3), 88 (3), 83 (3), 82 (6), 81 (10), 80 (3), 78 (3), 77 (5), 74 (3), 73 (3), 70 (6), 69 (4), 68 (3), 63 (3), 61 (5), 59 (3), 58 (4), 57 (60), 56 (15), 55 (6), 54 (8), 52 (4), 51 (5), 50 (5).

Preparation 12 (Intermediate to Example 52A and Example 52B)

tert-Butyl 3-(3,5-difluorophenoxy)azetidine-1-carboxylate 3,5-Difluorophenol (4.00 g, 30.7 mmol) was dissolved in DCM (100 mL) together with tert-butyl 3-hydroxyazetidine-1-carboxylate (6.92 g, 40.0 mmol) and triphenyl phosphine (10.4 g, 39.7 mmol). Diisopropyl azodicarboxylate (7.8 mL, 39.7 mmol) was then added dropwise to the resultant solution at 0° C. The mixture was stirred with cooling for one hour and then at RT for 17 h. After dilution with DCM, the solution was washed with an aqueous solution of Na$_2$CO$_3$, brine, and then dried over Na$_2$SO$_4$. The solvent was removed by evaporation. The product was purified in three portions by column chromatography using 100 g silica-gel each time with a gradient of isooctane/EtOAc (0-8% EtOAc) to provide 2.38 g (27%) of the title compound as an oil that was slightly contaminated with the starting phenol. GC MS m/z (relative intensity, 70 eV). 230 (9), 229 (64), 212 (10), 185 (2), 169 (2), 167 (2), 157 (10), 156 (bp), 144 (2), 143 (23), 141 (3), 130 (13), 128 (7), 127 (36), 115 (3), 114 (2), 113 (4), 102 (5), 101 (9), 82 (14), 75 (2), 63 (4), 58 (6), 57 (98), 56 (13), 55 (5), 54 (5).

Preparation 13 (Intermediate to Example 74)

tert-Butyl 3-[3,5-difluoro(2,4,6-$^2$H$_3$)phenoxy]azetidine-1-carboxylate 3,5-difluorophenol (0.134 g, 1.03 mmol) was placed in a vial together with deuterated TFA (5 g, 43 mmol) and the vial was heated to 80-85° C. over night. The volatiles were removed by evaporation and the residue was partitioned between DCM and an aqueous bicarbonate solution. The organic solution was removed by evaporation and the solid residue (33 mg) was dissolved in DCM (1 mL) together with tert-butyl 3-hydroxyazetidine-1-carboxylate (60 mg, 0.35 mmol) and triphenyl phosphine (90 mg, 0.34 mmol). Diisopropyl azodicarboxylate (0.07 mL, 0.35 mmol) was added and the mixture was stirred at RT for four days. The product was purified by column chromatography on silica-gel using a gradient of isooctane/EtOAc (0-18% EtOAc) to provide 30 mg (10%) of the title compound. GC MS m/z (relative intensity, 70 eV). 233 (5), 232 (40), 231 (12), 215 (8), 160 (6), 159 (69), 158 (23), 157 (6), 146 (13), 145 (6), 133 (11), 130 (21), 129 (14), 104 (6), 82 (13), 58 (6), 57 (bp), 56 (13), 55 (6), 54 (6).

The following tests were used for evaluation of compounds as disclosed herein.

In Vivo Test: Behaviour

Behavioural activity was measured using eight Digiscan activity monitors (RXYZM (16) TAO, Omnitech Electronics, Columbus, Ohio, USA), connected to an Omnitech Digiscan analyzer and an Apple Macintosh computer equipped with a digital interface board (NB D10-24, National Instruments, USA). Each activity monitor consisted of a quadratic metal frame (W×L=40 cm×40 cm) equipped with photo beam sensors. During measurements of behavioural activity, a rat was put in a transparent acrylic cage (W×L×H, 40×40×30 cm) which in turn was placed in the activity monitor. Each activity monitor was equipped with three rows of infrared photo beam sensors, each row consisting of 16 sensors. Two rows were placed along the front and the side of the floor of the cage, at a 90° angle, and the third row was placed 10 cm above the floor to measure vertical activity. Photo beam sensors were spaced 2.5 cm apart. Each activity monitor was fitted in an identical sound and light attenuating box containing a weak house light and a fan.

The computer software was written using object oriented programming (LabVIEW™, National instruments, Austin, Tex., USA).

Behavioural data from each activity monitor, representing the position (horizontal center of gravity and vertical activity) of the animal at each time, were recorded at a sampling frequency of 25 Hz and collected using a custom written LABView™ application. The data from each recording session were stored and analyzed with respect to distance traveled. Each behavioural recording session lasted 60 min, starting approximately 5 min after the injection of test compound.

Compounds disclosed herein have been tested for effects on spontaneous locomotor activity in non-pre-treated Sprague-Dawley rats (based on accumulated distance traveled 0-60 min post dosing), and with doses up to 100 µmol/kg (s.c.).

No increase in locomotor activity was observed over a wide dose range of the compounds disclosed herein, if anything there was a significant reduction for some of them, such as compound of example 2 at all tested doses and compound of example 3 at the two highest doses and compound of example 39 at the highest tested dose. For the reference compound a significant increase in locomotor activity was observed at the highest dose.

Some of the compounds of this disclosure have no effect on locomotor activity, when locomotor activity is measured in an assay as described herein and locomotor activity is expressed as of control means and the control means is saline solution. Some embodiments of this disclosure reduce locomotor activity, when locomotor activity is measured in an assay as described herein and locomotor activity is expressed as % of control means and the control means is saline solution. Some embodiments of this disclosure reduce locomotor activity in a dose dependent manner when locomotor activity is measured in an assay as described herein and locomotor activity is expressed as % of control means and the control means is saline solution. At low dosages, such as about 11 µmol/kg some of the compounds of this disclosure have no effect on locomotor activity, when locomotor activity is measured in an assay as described herein and locomotor activity is expressed as % of control means and the control means is saline solution.

At low dosages, such as about 11 µmol/kg some compounds according to this disclosure reduce the locomotor activity to about 95% or less, when locomotor activity is measured in an assay as described herein and locomotor activity is expressed as % of control means and the control means is saline solution. At low dosages, such as about 11 µmol/kg some compounds according to this disclosure reduce the locomotor activity to about 70% or less, when locomotor activity is measured in an assay as described herein and locomotor activity is expressed as of control means and the control means is saline solution.

At medium dosages, such as about 33 µmol/kg some of the compounds of this disclosure have no effect on locomotor activity, when locomotor activity is measured in an assay as described herein and locomotor activity is expressed as % of control means and the control means is saline solution. At medium dosages, such as about 33 µmol/kg some compounds according to this disclosure reduce the locomotor activity to about 75% or less, when locomotor activity is measured in an assay as described herein and locomotor activity is expressed as % of control means and the control means is saline solution. At medium dosages, such as about 33 µmol/kg some compounds according to this disclosure reduce the locomotor activity to about 60% or less, when locomotor activity is measured in an assay as described herein and locomotor activity is expressed as % of control means and the control means is saline solution. At medium dosages, such as about 33 µmol/kg some compounds according to this disclosure reduce the locomotor activity to about 35% or less, when locomotor activity is measured in an assay as described herein and locomotor activity is expressed as % of control means and the control means is saline solution.

At high dosages, such as about 100 µmol/kg some of the compounds of this disclosure have no effect on locomotor activity, when locomotor activity is measured in an assay as described herein and locomotor activity is expressed as % of control means and the control means is saline solution. At high dosages, such as about 100 µmol/kg some of the compounds of this disclosure have no effect on locomotor activity, when locomotor activity is measured in an assay as described herein and locomotor activity is expressed as % of control means and the control means is saline solution, however show a reduces locomotor activity when compared to the reference compound 3-(3,4-dichlorophenoxy)azetidine hydrochloric acid. At high dosages, such as about 100 µmol/kg some compounds according to this disclosure reduce the locomotor activity to about 80-90% or less, when locomotor activity is measured in an assay as described herein and locomotor activity is expressed as % of control means and the control means is saline solution. At high dosages, such as about 100 µmol/kg some compounds according to this disclosure reduce the locomotor activity to about 70% or less, when locomotor activity is measured in an assay as described herein and locomotor activity is expressed as % of control means and the control means is saline solution. At high dosages, such as about 100 µmol/kg some compounds according to this disclosure reduce the locomotor activity to about 55% or less, when locomotor activity is measured in an assay as described herein and locomotor activity is expressed as % of control means and the control means is saline solution. At high dosages, such as about 100 µmol/kg some compounds according to this disclosure reduce the locomotor activity to about 26% or less, when locomotor activity is measured in an assay as described herein and locomotor activity is expressed as % of control means and the control means is saline solution.

The term "about" as used herein means in reasonable vicinity of the stated numerical value, such as plus or minus 10%.

The increase in locomotor activity is a hall mark of psychostimulants like amphetamine and cocaine and can be used as a predictor for potential abuse liability. The significant affinity of the reference compound for DAT correlates well with the observed increase in locomotor activity. (Table 1).

TABLE 1

Effects of compounds disclosed herein on locomotor activity in drug-naïve rats.

| Example | 11 µmol/kg (% of control means[a]) | 33 µmol/kg (% of control means[a]) | 100 µmol/kg (% of control means[a]) |
|---|---|---|---|
| Reference Compound* | 132 ± 10 | 108 ± 23 | 323 ± 50** |
| Example 1A | 135 ± 17 | 163 ± 17* | 121 ± 23 |
| Example 2 | 66 ± 8** | 57 ± 5*** | 21 ± 5*** |
| Example 3 | 114 ± 18 | 71 ± 26 | 44 ± 8* |
| Example 39 | 132 ± 14 | 103 ± 18 | 78 ± 19 |
| Example 52B | 93 ± 15 | 30 ± 5* | 46 ± 8 |
| Example 52C | 128 ± 25 | 74 ± 24 | 73 ± 15 |

[a]Control group treated with saline solution.
*Reference Compound: 3-(3,4-dichlorophenoxy)azetidine hydrochloric acid.

The animals were placed in the motility meters immediately after drug administration and locomotor activity was recorded for 60 minutes (counts/60 min). Results are presented as percent of control means. Statistical significance was assessed using Student's t-test (2 tailed) vs controls. * denotes $p<0.05$,  $p<0.01$, * $p<0.001$, n=5.

In Vivo Test: Neurochemistry

After the behavioural activity sessions, the rats were decapitated and their brains rapidly taken out and put on an ice-cold petri-dish. The brains were dissected into a right and a left part of which the right part was analyzed for neurochemicals with HPLC and the left part was analyzed for gene expression. The limbic forebrain, the striatum, the frontal cortex, the hippocampus and the remaining hemispheral parts of each rat were dissected and frozen. Each brain part was subsequently analyzed with respect to its content of monoamines and their metabolites.

The monoamine transmitter substances (NA (noradrenaline), DA (dopamine), 5-HT (serotonin)) as well as one corresponding acid, (DOPAC (3,4-dihydroxyphenylacetic acid), were quantified in brain tissue homogenates by HPLC separations and electrochemical detection.

The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18 (2), dp 3 µm, 50*2 mm i.d., Phenomenex) and electrochemical detection is accomplished at two potentials on glassy carbon electrodes (MF-1000, Bioanalytical Systems, Inc.). The column effluent is passed via a T-connection to the detection cell or to a waste outlet. This is accomplished by two solenoid valves, which block either the waste or detector outlet. By preventing the chromatographic front from reaching the detector, better detection conditions are achieved. The aqueous mobile phase (0.4 ml/min) for the acid system contains citric acid 14 mM, sodium citrate 10 mM, Methanol 15% (v/v) and EDTA 0.1 mM. Detection potentials relative to Ag/AgCl reference are 0.45 and 0.60V. The aqueous ion pairing mobile phase (0.5 ml/min) for the amine system contains citric acid 5 mM, sodium citrate 10 mM, Methanol 9% (v/v), MeCN 10.5% v/v), decane sulfonic acid 0.45 mM, and EDTA 0.1 mM. Detection potentials relative to Ag/AgCl reference are 0.45 and 0.65V.

Compounds disclosed herein have been shown to increase the DOPAC levels with a regional preference for the cortex (Table 2).

Some of the compounds of this disclosure increase the levels of DOPAC in the cortex to about 120% of control means, when measured in an assay as disclosed herein, wherein the concentration of each tested compound is 100 µmol/kg and wherein the control means is treatment with saline solution. Some of the compounds of this disclosure increase the levels of DOPAC in the cortex to about 200% of control means, when measured in an assay as disclosed herein, wherein the concentration of each tested compound is 100 µmol/kg and wherein the control means is treatment with saline solution. Some of the compounds of this disclosure increase the levels of DOPAC in the cortex to about 230% of control means, when measured in an assay as disclosed herein, wherein the concentration of each tested compound is 100 µmol/kg and wherein the control means is treatment with saline solution. Some of the compounds of this disclosure increase the levels of DOPAC in the cortex to about 300% of control means, when measured in an assay as disclosed herein, wherein the concentration of each tested compound is 100 µmol/kg and wherein the control means is treatment with saline solution. Some of the compounds of this disclosure increase the levels of DOPAC in the striatum to about 200% or about 300% of control means, when measured in an assay as disclosed herein, wherein the concentration of each tested compound is 100 µmol/kg and wherein the control means is treatment with saline solution. Some of the compounds of this disclosure increase the levels of DOPAC in the cortex up to about 300% of control means, when measured in an assay as disclosed herein, wherein the concentration of each tested compound is 100 µmol/kg and wherein the control means is treatment with saline solution. Some of the compounds of this disclosure increase the levels of DOPAC in the cortex to about 300% or more of control means, when measured in an assay as disclosed herein, wherein the concentration of each tested compound is 100 µmol/kg and wherein the control means is treatment with saline solution.

Some of the compounds of this disclosure increase the levels of DOPAC in the striatum and cortex, when measured in an assay as disclosed herein, wherein the concentration of each tested compound is 100 µmol/kg. Some of the compounds of this disclosure have no effect on the levels of DOPAC in the striatum or cortex, when measured in an assay as disclosed herein, wherein the concentration of each tested compound is 100 µmol/kg. Some of the compounds of this disclosure have no effect on the levels of DOPAC in the striatum and cortex, when measured in an assay as disclosed herein, wherein the concentration of each tested compound is 100 µmol/kg. Some of the compounds of this disclosure have no effect on the levels of DOPAC in the striatum and/or cortex, however increase levels of DOPAC in the striatum and/or cortex when compared to the reference compound 3-(3,4-dichlorophenoxy)azetidine hydrochloric acid, when measured in an assay as disclosed herein, wherein the concentration of each tested compound is 100 µmol/kg.

TABLE 2

Effects on tissue levels of DOPAC in two different brain regions after subcutaneous administration to rats (100 µmol/kg)

| Compound | DOPAC striatum ± SEM (% of control means[a]) | DOPAC cortex ± SEM (% of control means[a]) |
| --- | --- | --- |
| Reference Compound* | 89 ± 2.5 | 86 ± 5.6 |
| Example 1A | 53 ± 2*** | 300 ± 26*** |
| Example 2 | 96 ± 4 | 121 ± 5.6 |
| Example 3 | 158 ± 3.4*** | 201 ± 11*** |
| Example 39 | 247 ± 13*** | 191 ± 18** |
| Example 52B | 72 ± 1.7*** | 229 ± 4.6*** |

[a]Control group treated with saline solution.
*Reference Compound: 3-(3,4-dichlorophenoxy)azetidine hydrochloric acid.

Each compound or saline solution (control) indicated in the above table was administered subcutaneously (s.c.) 65 min before sacrificing the animals. DOPAC results are presented as percent of control means±SEM (standard error of the mean). Statistical significance was assessed using Student's t-test (2 tailed) vs controls. * denotes $p<0.05$,  $p<0.01$, * $p<0.001$, n=5.

In Vivo Test: Oral Bioavailability

Experiments are performed 48 hours after implantation of arterial and venous catheters. Test compound is administered orally at 12.5 µmol/kg or intravenously at 5 µmol/kg using the venous catheters, n=3 per group. Arterial blood samples are then taken during six hours at 0, 3, 9, 27, 60, 120, 180, 240, 300 and, 360 minutes after administration of the test compound. The oral bioavailability was calculated as the ratio of the AUC (Area under curve) obtained after oral administration over the AUC obtained after intravenous administration for each rat. The parameter AUC was calculated according to the following:

AUC: the area under the plasma concentration versus time curve from time zero to the last concentration measured (Clast), calculated by the log/linear trapezoidal method.

The levels of test compound are measured by means of liquid chromatography-mass spectrometry (LC-MS) (Hewlett-Packard 1100MSD Series). The LC-MS module includes a quaternary pump system, vacuum degasser, thermostatted autosampler, thermostatted column compartment, diode array detector and API-ES spray chamber. Data handling was performed with a HP ChemStation rev.A.06.03. system. Instrument settings: MSD mode: Selected ion monitoring (SIM) MSD polarity: Positiv Gas temp: 350° C. Drying gas: 13.0 l/min Nebulizer gas: 50 psig Capillary voltage: 5000 V Fragmentor voltage: 70 V Analytical column: ACE EXCEL 3 C18-PFP (3.0*100 mm, 3.0 µm) at 20° C. The mobile phase was acetic acid (0.03%) (solvent A) and acetonitrile (solvent B). The flow rate of the mobile phase was 0.5 ml/min. The elution was starting at 5% of solvent B, then increasing linearity to 70% over 7 min.

Extractions Procedure:

100 µl of plasma samples are mixed with 400 µl ACN containing internal standard. After mixing, the samples are centrifuged 10 min, 4° C., 14000 rpm. The supernatants are transferred to other tubes and evaporated under a stream of nitrogen. The residue was then dissolved in 150 µl 0.1% HAc, centrifuged and transferred to 100 µl glass vials for LC-MS analysis (10 µl injected). The selective ion (MH+) was monitored. A standard curve over the range of 1-500 µmol is prepared by adding appropriate amounts of test compounds to blank plasma samples.

In Vitro Test: Metabolic Stability in Rat Liver Microsomes

Pooled male rat liver microsomes (RLM) (20 mg/ml) was bought from BD Bioscience (#452501).

Pooled male dog liver microsomes (DLM) (20 mg/ml) was bought from BD Bioscience (#452601).

Pooled human liver microsomes (HLM) (20 mg/ml) was bought from BD Bioscience (#452161). 1 µL of, 0.2 or 1 mM test substance diluted in water, and 10 µl 20 mg/mL rat liver microsomes were mixed with 149 µl 37° C. buffer 1 and the reaction was started by addition of 40 µL 4.1 mg/mL NADPH. After 15 or 60 minutes incubation at 37° C. in a heating block (LAB-LINE, MULTI-BLOK Heater or lab4you, TS-100 Thermo shaker at 700 rpm) the reaction was stopped by addition of 100 µl pure acetonitrile. The protein precipitation was then removed by rejecting the pellet after centrifugation at 10.000 g for 10 minutes (Heraeus, Biofuge fresco) in 4° C. The test compound was analyzed using HPLC-MS (Hewlett-Packard 1100MSD Series) with a Zorbax SB-C18 column (2.1*150 mm, 5 µm) using 0.03% formic acid and acetonitrile as mobile phase (gradient) or an ACE EXCEL 3 C18-PFP (3.0*100 mm, 3.0 µm) using 0.03% acetic acid and acetonitrile as mobile phase (gradient). The 15 min turnover was calculated as the fraction of test compound eliminated after 15 minutes, expressed in percent of 0 min levels, i.e. 100*[conc. test compound at 0 min—concentration at 15 min]/conc. at 0 min. Protocols for incubation with liver microsomes are referred in Crespi CL and Stresser D M, J Pharm Tox Meth, 2000, 44; 325-31 and Renwick A B et al., Xenobiotica, 2001, 31(4); 187-204.

Microdialysis

Male Sprague-Dawley rats weighing 280-320 g were used throughout the experiments. Before the experiment the animals were housed in groups, maximum five animals in each cage, with free access to water and food. The animals were housed at least one week prior to surgery and use in the experiments.

A modified version (Waters et al., J Neural Transm Gen Sect, 1994, 98(1); 39-55) of the !-shaped probe (Santiago and Westerink, N-S Arch Pharmacol, 1990, 342; 407-14) with the AN69 polyacrylonitrile/sodium methyl sulfonate copolymer (HOSPAL; o.d/i.d. 310/220 µm: dialysis membrane (Gambro, Lund, Sweden) was used in the microdialysis experiments. In the dorsal striatum, probes with an exposed length of 3 mm of dialysis membrane were used and in the prefrontal cortex the corresponding length was 2.5 mm. The rats were operated under isoflurane inhalation anesthesia while mounted into a Kopf stereotaxic instrument. Coordinates were calculated relative to bregma; dorsal striatum AP+1.0, ML±2.6, DV 6.2; Pf cortex, AP+3.2, ML±1.2, DV −4.0 8°, according to Paxinos and Watson (New York, Academic Press, 1986; FIG. 8 and FIG. 14). The dialysis probe was positioned in a burr hole under stereotaxic guidance and cemented with phosphatine dental cement (DAB Dental).

The rats were housed individually in cages for 48 h before the dialysis experiments, allowing them to recover from surgery and minimizing the risk of drug interactions with the anesthetics during the following experiments. During this period the rats had free access to food and water. On the day of the experiment the rats were connected to a microperfusion pump via a swivel and were replaced in the cage where they could move freely within its confinements. The perfusion medium was a Ringer's solution containing (in mmol/l): NaCl; 140, CaCl$_2$); 1.2, KCl; 3.0, MgCl2; 1.0 (Moghaddam and Bunney. Neurochem., 1989, 53; 652-4). The pump was set to a perfusion speed of 2 µl/min and 40 µl sample volume were collected every 20 min.

The rats were perfused for at least 40 min before sampling began. Five fractions of each 20 min were collected and the last three were used for the establishment of the baseline. After collection of baseline fractions, the pharmacological challenge to the dialysis experiment started. Test compounds were administered by injection (s.c.) in a volume of 5 ml/kg, with 0.9% NaCl (saline) as vehicle.

The analytical method were based on two chromatographic separations dedicated for amines or acids. Two chromatographic systems shared a common auto injector with a 10-port valve and two sample loops for simultaneous injection on the two systems.

The acids were separated by reversed phase chromatography while the amines were separated by reversed phase ion pairing chromatography preceded by a reverse phase separation in a column switching configuration. Three separation columns (Luna C18 (2), dp 3 µm, 2 mm i.d., Phenomenex) of different lengths were used. Electrochemical detection was accomplished on glassy carbon electrodes (MF-1000, Bioanalytical Systems, Inc.)

The aqueous mobile phase (0.6 ml/min) for the acid system contained citric acid (40 mM, dipotassium hydrogen phosphate 10 mM, methanol 8-11% (v/v) and EDTA 0.1 mM. Column length was 30 mm and detection potential relative to Ag/AgCl reference was 0.74V.

The aqueous ion pairing mobile phase (0.4 ml/min) for the amine system contained citric acid 5 mM, sodium citrate 10 mM, acetone 9% (v/v), tetrahydrofurane 3% (v/v), dodecane sulphonic acid 0.025 mM, and EDTA 0.1 mM. Column length was 50 mm and the preceding column was 20 mm. Detection potentials relative to Ag/AgCl were 0.45 and 0.65V. The aqueous mobile phase for the coupled reversed phase separation was identical to the ion pairing mobile phase, except that no dodecane sulphonic acid was added.

After the experiment the rats were uncoupled from the perfusion pump, put to death with pentobarbital vet. and decapitated. The rat brains were rapidly taken out and stored in −20° C. for about 30 min before subsequent inspection of probe localization. The Animal Ethics Committee in Gothenburg, Sweden approved the procedures applied in these experiments.

Data analysis: Only results from rats with correctly positioned dialysis probes, as verified by visual examination of brain tissue post mortem, were included in the statistical analyses. Pre-drug baseline values for each analyte and region were calculated by averaging the levels measured in three consecutive fractions collected immediately before administration of test compound. Monoamine dialysate content at each time-point after dosing was then calculated as the percentage of baseline levels. The data from all rats were then averaged, for each time-point. In the tables presented herein, the maximal increases observed after dosing, i.e. the maximal value of the mean percentages of the pre-drug baseline, are shown. The number of rats used for the calculation of mean percentages for each analyte and region are also given in the tables.

Using in vivo brain microdialysis, compounds disclosed herein have been shown to increase the extracellular levels of dopamine and norepinephrine (noradrenaline) with a regional preference for the frontal cortex (FC) over striatum (Stri). In some cases serotonin is also increased across brain regions (Table 3). Some of the compounds of this disclosure have shown and increase level of extracellular dopamine and norephinephrine in either the frontal cotex or the striatum, or both, in addition to the reported decreased affinity to SERT, NET and/or DAT when compared to the control group treated with saline solution. Some of the compounds of this disclosure have shown and increase level of extracellular dopamine and norephinephrine in either the frontal cotex or the striatum, or both, in addition to the reported decreased affinity to SERT, NET and/or DAT when compared to the control group treated with saline solution, wherein the SERT, NET and/or DAT levels are lower than the reference Compound: 3-(3,4-dichlorophenoxy)azetidine hydrochloric acid.

Some of the compounds of this disclosure have shown and increase level of extracellular dopamine and norephinephrine in either the frontal cotex or the striatum, or both, in addition to the reported decreased affinity to SERT, NET and/or DAT when compared to the control group treated with saline solution, wherein the SERT, NET and/or DAT levels are between below 0% and up to 60% relative to controls, which is lower than the reference Compound: 3-(3,4-dichlorophenoxy)azetidine hydrochloric acid levels of between about 89 to about 95% relative to controls.

Some compounds as disclosed herein increase the extracellular levels of dopamine in the striatum (Stri) to between about 100% to about 150% relative to control groups treated with saline when measured in accordance with assays disclosed herein. Some compounds as disclosed herein increase the extracellular levels of dopamine in the striatum (Stri) to between about 150% to about 220% relative to control groups treated with saline when measured in accordance with assays disclosed herein. Some compounds as disclosed herein increase the extracellular levels of dopamine in the striatum (Stri) to about 220% relative to control groups treated with saline when measured in accordance with assays disclosed herein. Some compounds as disclosed herein increase the extracellular levels of dopamine in the striatum (Stri) up to about 220% relative to control groups treated with saline when measured in accordance with assays disclosed herein. Some compounds as disclosed herein increase the extracellular levels of dopamine in the striatum (Stri) to about 220% relative to control groups or more relative to control groups treated with saline when measured in accordance with assays disclosed herein.

Some compounds as disclosed herein increase the extracellular levels of dopamine in the striatum (Stri) in addition to the reported decreased affinity to SERT, NET and/or DAT relative to the control group. Some compounds as disclosed herein increase the extracellular levels of dopamine in the striatum (Stri) level in addition to the reported unchanged or decreased locomotor activity relative to the control group. Some compounds as disclosed herein increase the extracellular levels of dopamine in the striatum (Stri) in addition to the reported unchanged or decreased locomotor activity and/or to the reported decreased affinity to SERT, NET and/or DAT, relative to the control group. Some compounds as disclosed herein increase the extracellular levels of dopamine in the striatum (Stri) in addition to the reported unchanged or increased Arc level in the Striatum or Frontal Cortex, relative to the control group.

Some compounds as disclosed herein increase the extracellular levels of norepinephrine in the striatum (Stri) to between about 150 to about 200% relative to control groups treated with saline when measured in accordance with assays disclosed herein. Some compounds as disclosed herein increase the extracellular levels of norepinephrine in the striatum (Stri) to between about 200% to 300% relative to control groups treated with saline when measured in accordance with assays disclosed herein. Some compounds as disclosed herein increase the extracellular levels of norepinephrine in the striatum (Stri) to between about 400% to about 500% relative to control groups treated with saline when measured in accordance with assays disclosed herein. Some compounds as disclosed herein increase the extracellular levels of norepinephrine in the striatum (Stri) to about 500% relative to control groups treated with saline when measured in accordance with assays disclosed herein. Some compounds as disclosed herein increase the extracellular levels of norepinephrine in the striatum (Stri) up to about 500% relative to control groups treated with saline when measured in accordance with assays disclosed herein. Some compounds as disclosed herein increase the extracellular levels of norepinephrine in the striatum (Stri) to about 500% or more relative to control groups treated with saline when measured in accordance with assays disclosed herein.

Some compounds as disclosed herein increase the extracellular levels of norepinephrine in the striatum (Stri) in addition to the reported decreased affinity to SERT, NET and/or DAT relative to the control group. Some compounds as disclosed herein increase the extracellular levels of dopamine in the striatum (Stri) level in addition to the reported unchanged or decreased locomotor activity relative to the control group. Some compounds as disclosed herein increase the extracellular levels of dopamine in the striatum (Stri) in addition to the reported unchanged or decreased locomotor activity and/or to the reported decreased affinity to SERT, NET and/or DAT, relative to the control group. Some compounds as disclosed herein increase the extracellular levels of dopamine in the striatum (Stri) in addition to the reported unchanged or increased Arc level in the Striatum or Frontal Cortex, relative to the control group.

Some compounds as disclosed herein increase the extracellular levels of dopamine in the frontal cortex (FC) to between about 350% to 400% relative to control groups treated with saline when measured in accordance with assays disclosed herein.

Some compounds as disclosed herein increase the extracellular levels of dopamine in the frontal cortex (FC)) to between about 400% to 600% relative to control groups treated with saline when measured in accordance with assays disclosed herein.

Some compounds as disclosed herein increase the extracellular levels of dopamine in the frontal cortex (FC) to between about 600% to 800% relative to control groups treated with saline when measured in accordance with assays disclosed herein. Some compounds as disclosed herein increase the extracellular levels of dopamine in the frontal cortex (FC) to about 1600% relative to control groups treated with saline when measured in accordance with assays disclosed herein. Some compounds as disclosed herein increase the extracellular levels of dopamine in the frontal cortex (FC) up to about 1600% relative to control groups treated with saline when measured in accordance with assays disclosed herein. Some compounds as disclosed herein increase the extracellular levels of dopamine in the frontal cortex (FC) to about 1600% or more relative to control groups treated with saline when measured in accordance with assays disclosed herein.

Some compounds as disclosed herein increase the extracellular levels of norepinephrine in the frontal cortex (FC) to between about 400% to 800% relative to control groups treated with saline when measured in accordance with assays disclosed herein.

Some compounds as disclosed herein increase the extracellular levels of dopamine in the frontal cortex (FC)) to between about 800% to 1000% relative to control groups treated with saline when measured in accordance with assays disclosed herein.

Some compounds as disclosed herein increase the extracellular levels of dopamine in the frontal cortex (FC) to between about 1000% to 1400% relative to control groups treated with saline when measured in accordance with assays disclosed herein. Some compounds as disclosed herein increase the extracellular levels of dopamine in the frontal cortex (FC) to between about 1400% to 2000% relative to control groups treated with saline when measured in accordance with assays disclosed herein. saline when measured in accordance with assays disclosed herein. Some compounds as disclosed herein increase the extracellular levels of dopamine in the frontal cortex (FC) to between about 2000% to 3600% relative to control groups treated with saline when measured in accordance with assays disclosed herein.

Some compounds as disclosed herein increase the extracellular levels of dopamine in the frontal cortex (FC) up to about 3600% relative to control groups treated with saline when measured in accordance with assays disclosed herein. Some compounds as disclosed herein increase the extracellular levels of dopamine in the frontal cortex (FC) to about 3600% or more relative to control groups treated with saline when measured in accordance with assays disclosed herein.

TABLE 3

Maximum effect compared to baseline values
(percent of control ± SEM) at 50 µmol/kg s.c.

| Compound | NA Stri (% of control*) ± SEM | DA Stri (% of control*) ± SEM | 5-HT Stri (% of control*) ± SEM | NA FC (% of control*) ± SEM | DA FC (% of control*) ± SEM | 5-HT FC (% of control*) ± SEM |
|---|---|---|---|---|---|---|
| Reference compound** | 987 ± 425 | 136 ± 48 | 1326 ± 13 | 2252 ± 687 | 1023 ± 141 | 682 ± 14 |
| Example 1A | 155 ± 33$^a$ | 155 ± 9.6$^a$ | 217 ± 21$^a$ | 2089 ± 530 | 1584 ± 070$^a$ | 207 ± 49$^a$ |
| Example 2 | — | 134 ± 13$^a$ | 202 ± 5.6$^a$ | 1415 ± 267$^a$ | 600 ± 5.8$^a$ | 160 ± 32$^a$ |
| Example 3 | — | 196 ± 22$^a$ | 197 ± 80$^a$ | 3642 ± 168$^a$ | 735 ± 18$^a$ | 205 ± 78$^a$ |
| Example 10 | — | 126 ± 10$^a$ | 1073 ± 557$^a$ | 799 ± 137$^a$ | 466 ± 161$^a$ | 709 ± 139$^a$ |
| Example 20 | — | 146 ± 4$^a$ | 141$^b$ | 1077 ± 203$^a$ | 441 ± 35$^a$ | 164 ± 36$^a$ |

TABLE 3-continued

Maximum effect compared to baseline values
(percent of control ± SEM) at 50 μmol/kg s.c.

| Compound | NA Stri (% of control*) ± SEM | DA Stri (% of control*) ± SEM | 5-HT Stri (% of control*) ± SEM | NA FC (% of control*) ± SEM | DA FC (% of control*) ± SEM | 5-HT FC (% of control*) ± SEM |
|---|---|---|---|---|---|---|
| Example 38 | 306 ± 146$^a$ | 203 ± 8$^a$ | 205 ± 20$^a$ | 422 ± 102$^a$ | 467 ± 20$^a$ | 148 ± 12$^a$ |
| Example 39 | 334 ± 10$^a$ | 218 ± 18$^a$ | 281$^b$ | 414$^b$ | 359$^b$ | 256$^b$ |
| Example 49 | 353$^b$ | 135 ± 2$^a$ | 573 ± 1$^a$ | 862 ± 437$^a$ | 391 ± 131$^a$ | 1234 ± 105$^a$ |
| Example 50 | — | 139 ± 20$^a$ | 574 ± 45$^a$ | 1516 ± 292$^a$ | 787 ± 131$^a$ | 752 ± 235$^a$ |
| Example 51 | 475$^b$ | 144 ± 4$^a$ | 663 ± 63$^a$ | 910 ± 389$^a$ | 389 ± 134$^a$ | 998 ± 470$^a$ |
| Example 52B*** | 151$^b$ | 120 ± 6$^c$ | 146 ± 18$^a$ | 968 ± 176$^c$ | 638 ± 106$^c$ | 213 ± 86$^a$ |
| Example 52C | 196 ± 26$^a$ | 147 ± 6$^a$ | 1053 ± 572$^a$ | 1850 ± 216$^a$ | 2138 ± 65$^a$ | 424 ± 119$^a$ |

$^a$n = 2, $^b$n = 1, $^c$n = 3
*.Compared to base line
**Reference Compound: 3-(3,4-dichlorophenoxy)azetidine hydrochloric acid.
***Dose 16.7 μmol/kg s.c m-RNA Analysis Animals were killed 60 min after the injection of the drugs by decapitation and the brains were dissected into four different areas: Limbic system (containing nucleus accumbens, most parts of the olfactory tubercle, ventral pallidum), striatum, frontal cortex, hippocampus and the remaining cortex.

Total RNA was prepared by the guanidin isothiocyanate method (Chomczynski P and Sacchi N, Anal Biochem, 1987, 162(1); 156-9). RNA pellets were solved in RNAse-free water and stored at −80° C. The sample concentration was determined spectrophotometrically by a NanoDrop ND1000 (Saveen Werner). A quality indicator number and an integrity number of r-RNA were measured with an Experion (Bio-rad).

A two-step reversed transcription was performed by using a SuperScript III kit (Invitrogen). 1 μg of total RNA was reverse transcribed with 5 μl 2XRT Reaction Mix, 1 μl RT Enzyme Mix, in a total volume adjusted to 10 μl with DEPC-treated water. 1 U of E. coli RNase H was added. c-DNA was diluted 40 times and stored at −20° C.

Three sequences (one gene of interest and two reference genes) were amplified together in a triplex PCR-reaction. For real-time PCR measurements: 5 μl of c-DNA reaction was amplified in a 20 μl reaction mixture containing 10 μl PerfeCta Multiplex qPCR Supermix (Quanta, VWR), 3.5 μl RNAse-free water, 0.15 μM of each primer and 0.1 μM of each probe. Real-time PCR was measured on CFX96 (Bio-rad) using the following settings for all genes: 3 min pre-incubation at 95° C. followed by 40 cycles of denaturation at 95° C. for 15 s, annealing and elongation at 60° C. for 1 minute.

Reference genes are HPRT and cyclophilin.

A recent human genetic study (Landgren et al., 2012) has shown that a particular sequence variant in the 3′UTR of Arc (activity-regulated cytoskeleton-associated protein) mRNA leads to a decreased likelihood of developing Alzheimer's disease Some of the compounds disclosed herein have been shown to increase the Arc mRNA in striatum and the frontal cortex and some with regional preference for the frontal cortex (Table 3).

Some compounds of this disclosure have no effect on the Arc levels compared to the control group in the Striatum or the Frontal Cortex, when levels of Arc was measured in an assay as disclosed herein, and wherein the concentration of each tested compound was 33_μmol/kg and the control group was treated with saline solution. Some compounds of this disclosure have no effect on the Arc levels compared to the control group in the Striatum however increase levels of Arc in the Frontal Cortex, when levels of Arc was measured in an assay as disclosed herein, and wherein the concentration of each tested compound was 33_μmol/kg and the control group was treated with saline solution.

Some compounds of this disclosure increase the level of Arc in the Striatum relative to the control group to about 140% of the control group, when levels of Arc was measured in an assay as disclosed herein, and wherein the concentration of each tested compound was 33_μmol/kg and the control group was treated with saline solution. Some compounds of this disclosure increase the level of Arc in the Striatum relative to the control group up to about 150% of the control group, when levels of Arc was measured in an assay as disclosed herein, and wherein the concentration of each tested compound was 33_μmol/kg and the control group was treated with saline solution. Some compounds of this disclosure increase the level of Arc in the Striatum relative to the control group to about 150% of the control group or more, when levels of Arc was measured in an assay as disclosed herein, and wherein the concentration of each tested compound was 33 μmol/kg and the control group was treated with saline solution.

Some compounds of this disclosure increase the level of Arc in the Frontal Cortex relative to the control group to about 150% of the control group, when levels of Arc was measured in an assay as disclosed herein, and wherein the concentration of each tested compound was 33 μmol/kg and the control group was treated with saline solution. Some compounds of this disclosure increase the level of Arc in the Frontal Cortex relative to the control group to about 150% to about 200% of the control group, when levels of Arc was measured in an assay as disclosed herein, and wherein the concentration of each tested compound was 33_μmol/kg and the control group was treated with saline solution. Some compounds of this disclosure increase the level of Arc in the Striatum relative to the control group to about 240% of the control group, when levels of Arc was measured in an assay as disclosed herein, and wherein the concentration of each tested compound was 33 μmol/kg and the control group was treated with saline solution. Some compounds of this disclosure increase the level of Arc in the Striatum relative to the control group up to about 240% of the control group, when levels of Arc was measured in an assay as disclosed herein, and wherein the concentration of each tested compound was 33 µmol/kg and the control group was treated with saline solution. Some compounds of this disclosure increase the level of Arc in the Striatum relative to the control group to about 240% of the control group or more when levels of Arc was measured in an assay as disclosed herein, and wherein the concentration of each tested compound was 33 µmol/kg and the control group was treated with saline solution.

Some of the compounds of the present invention show increased Arc mRNA level in addition to the reported decreased affinity to SERT, NET and/or DAT relative to the control group. Some of the compounds of the present invention show increased Arc mRNA level in addition to the reported unchanged or decreased locomotor activity relative to the control group. Some of the compounds of the present invention show increased Arc mRNA level in addition to the reported unchanged or decreased locomotor activity and/or to the reported decreased affinity to SERT, NET and/or DAT, relative to the control group.

TABLE 4

Effects on tissue levels of Arc in two different brain regions after subcutaneous administration to rats (33 µmol/kg).

| Compound | Arc striatum (% of means$^a$) ± SEM | Arc frontal cortex control (% of control means$^a$) ± SEM |
| --- | --- | --- |
| Example 1A | 149 ± 11* | 236 ± 9*** |
| Example 2 | 104 ± 12 | 96 ± 20 |
| Example 3 | 141 ± 9.0** | 149 ± 11** |
| Example 52B | 106 ± 7.1 | 148 ± 6.9** |

$^a$Control group treated with saline solution

Compounds and saline solution (control) as indicated above were administered s.c. 65 min before sacrificing the animals. Results are presented as percent of control means±SEM. Statistical significance was assessed using Student's t-test (2 tailed) vs controls. * denotes p<0.05,  p<0.01, n=5, * p<0.001, n=5.

SEQUENCE LISTING

The primer and probe sequences are as follows for measuring of arc:
Activity-Regulated Gene (Arc) (Accession Number 019866)
Sense: 5'-GGA GTT CAA GAA GGA GTT TC-3' (SEQ ID NO:1)
Antisense 5'-CCA CAT ACA GTG TCT GGT A-3' (SEQ ID NO:2)
Probe: CCG CTT ACG CCA GAG GAA CT (SEQ ID NO:3)
Dye: 5'FAM Quencher: 3'BHQ1
Product size: 149
Hypoxantine Phosphoribosyl Transferase (HPRT) (Accession Number AF001282)
Sense: 5'-AGG GAT TTG AAT CAT GTT TG-3' (SEQ ID NO:4)
Antisense 5'-CTG CTA GTT CTT TAC TGG C-3' (SEQ ID NO:5)
Probe: TGT AGA TTC AAC TTG CCG CTG TC (SEQ ID NO:6)
Dye: 5'HEX Quencher: 3'BHQ1
Product size: 121
Cyclophilin A (Cyclo) (Accession Number M19533)
Sense: 5'-CTG GAC CAA ACA CAA ATG-3' (SEQ ID NO:7)
Antisense 5'-ATG CCT TCT TTC ACC TTC-3' (SEQ ID NO:8)
Probe: TTG CCA TCC AGC CAC TCA GT (SEQ ID NO:9)
Dye: 5'Texas red Quencher: 3'BHQ2
Product size: 100

The primer and probe sequences are as follows for measuring of bdnf, cfos, gad, glud, penk:
Brain Derived Neurotrophic Factor (Bdnf) (Accession Number NM_012513)
Sense: 5'-AAA TTA CCT GGA TGC CGC AAA C-3' (SEQ ID NO:10)
Antisense 5'-TGT GAC CCA CTC GCT AAT ACT G-3' (SEQ ID NO:11)
Probe: CAC ACA CGC TCA GCT CCC CAC GG (SEQ ID NO:12)
Dye: 5'FAM Quencher: 3'BHQ1
Product size: 106
Rattus norvegicus Proto-Oncogen (c-Fos) (Accession Number DQ089699)
Sense: 5'-CAG AGC ATC GGC AGA AGG-3' (ref N Zoric) (SEQ ID NO:13)
Antisense 5'-AGT TGA TCT GTC TCC GCT TGG-3' (SEQ ID NO:14)
Probe: TCT GTC AGC TCC CTC CTC CGA TTC CG (SEQ ID NO:15)
Dye: 5'FAM Quencher: 3'BHQ1
Product size: 155
Glutamic Acid Decarboxylase (GAD 67) (Accession Number 34445)
Sense: 5'-CTG TTT ATG GAG CGT TTG ATC C-3' (SEQ ID NO:16)
Antisense: 5'-GAC TGA GAC TGA CCT TTC TAT G-3' (SEQ ID NO:17)
Probe: GAC TGA ATT GGC CCT TTC TAT G (SEQ ID NO:18)
Dye: 5'FAM Quencher: 3'BHQ1
Product size: 153
Glutamate Dehydrogenase (Glud) (Accession Number NM_012570)
Sense: 5'-AGC CTC TCC TTC CCC ATC C-3' (SEQ ID NO:19)
Antisense 5'-CGC CTT CAC CTC ATC CAC AC-3' (SEQ ID NO:20)
Probe: AGC ACA GCC AGC ACC GCA CGC (SEQ ID NO:21)
Dye: 5'FAM Quencher: 3'BHQ1
Product size: 141
Preproenkephalin (Penk) (Accession Number NM_017139.1)
Sense: 5'-CAT GTG CTG CTT GTG CTG T-3' (SEQ ID NO:22)
Antisense 5'-CAG TTG GGT TCA CGG GTT T-3' (SEQ ID NO:23)
Probe: TGC CCT CGT GGT CTG GAT AAC TGC (SEQ ID NO:24)
Dye: 5'FAM Quencher: 3'BHQ1
Product size: 228
Hypoxantine Phosphoribosyl Transferase (HPRT) (Accession Number AF001282)
Sense: 5'-GGC CAG ACT TTG TTG GAT TTG-3' (SEQ ID NO:25)
Antisense 5'-CCG CTG TCT TTT AGG CTT TG-3' (SEQ ID NO:26)
Probe: TTT CCA CTT TCG CTG ATG ACA CAA ACA T (SEQ ID NO:27)
Dye: 5'HEX Quencher: 3'BHQ1
Product size: 144

Cyclophilin A (Cyclo) (Accession Number M19533)
Sense: 5'-GTC TCT TTT CGC CGC TTG CT-3' (SEQ ID NO:28)
Antisense 5'-TCT GCT GTC TTT GGA ACT TTG TCT G-3' (SEQ ID NO:29)
Probe: ATG GTC AAC CCC ACC GTG TTC TTC GAC A (SEQ ID NO:30)
Dye: 5'Texas Red Quencher: 3'BHQ2
Product size: 127

Correct PCR products are confirmed by agarose gel electrophoresis (2%) PCR products are purified with PCR purification kit from Qiagen (Valencia, Calif., USA). All genes are sequenced at MWG, Germany. The amounts of gene of interests are normalized with the two reference genes HPRT and cyclophilin A with the equation delta-delta CT.

In Vitro Binding Assay and Data

The binding affinity of the compounds described herein was determined by competition binding assays similar to those described in references mentioned below, to evaluate the ability of a test compound to compete with the radioligand when binding to a transporter or receptor.

Human 5-HT Transporter (The measurement was performed as described in Tatsumi, M., Jansen, K., Blakely, R. D. and Richelson, E. (1999), Pharmacological profile of neuroleptics at human monoamine transporters, Eur. J. Pharmacol. 368: 277.)

Cell membrane homogenates (12 µg protein) are incubated for 60 min at 22° C. with 2 nM [3H]imipramine in the absence or presence of the test compound in a buffer containing 50 mM Tris-HCl (pH 7.4), 120 mM NaCl, 5 mM KCl and 0.1% BSA.

Nonspecific binding is determined in the presence of 10 µM imipramine.

Following incubation, the samples are filtered rapidly under vacuum through glass fiber filters (GF/B, Packard) presoaked with 0.3% PEI and rinsed several times with an ice-cold buffer containing 50 mM Tris-HCl and 150 mM NaCl using a 96-sample cell harvester (Unifilter, Packard). The filters are dried then counted for radioactivity in a scintillation counter (Topcount, Packard) using a scintillation cocktail (Microscint 0, Packard).

The results are expressed as a percent inhibition of the control radioligand specific binding Human Norepinephrine Transporter (The measurement was performed as described in Pacholczyk, T., Blakely, R. D. and Amara, S. G. (1991), Expression cloning of a cocaine- and antidepressant-sensitive human noradrenaline transporter, Nature, 350: 350)

Cell membrane homogenates (20 µg protein) are incubated for 120 min at 4° C. with 1 nM [3H]nisoxetine in the absence or presence of the test compound in a buffer containing 50 mM Tris-HCl (pH 7.4), 120 mM NaCl and 5 mM KCl. Nonspecific binding is determined in the presence of 1 µM desipramine. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard).

The results are expressed as a percent inhibition of the control radioligand specific binding.

Human Dopamine Transporter (The measurement was performed as described in Pristuba, Z. B., Wilson, J. M., Hoffman, B. J., Kish, S. J. and Nisnik, H. B. (1994), Pharmacological heterogeneity of the cloned and native human dopamine transporter: disassociation of [3H]WIN 35,428 and [3H]GBR 12,935 binding, Mol. Pharmacol., 45: 125)

Cell membrane homogenates (20 µg protein) are incubated for 120 min at 4° C. with 4 nM [3H]BTCP in the absence or presence of the test compound in a buffer containing 50 mM Tris-HCl (pH 7.4) and 100 mM NaCl. Nonspecific binding is determined in the presence of 10 µM BTCP. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard).

The results are expressed as a percent inhibition of the control radioligand specific binding.

Human Adrenergic Alpha 2A Receptor (The measurement was performed as described in Langin, D., Lafontan, M., Stilling, M. R. and Paris, H. (1989), [3H]RX821002: a new tool for the identification of alpha2A-adrenoceptors, Eur. J. Pharmacol. 167: 95.)

Cell membrane homogenates (48 µg protein) were incubated for 60 min at 22° C. with 1 nM [3H]RX 821002 in the absence or presence of the test compound in a buffer containing 50 mM Tris-HCl (pH 7.4), 2 mM MgCl2 and 1 mM EDTA. Nonspecific binding was determined in the presence of 100 µM (−)epinephrine. Following incubation, the samples were filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters were dried then counted for radioactivity in a scintillation counter (Topcount, Packard) using a scintillation cocktail (Microscint 0, Packard).

The results are expressed as a percent inhibition of the control radioligand specific binding.

Non-Selective Adrenergic Alpha 2 Receptor (antagonist radioligand). Membrane homogenates (rat) of cerebral cortex (160 µg protein) were incubated for 60 min at 22° C. with 0.5 nM [3H]RX 821002 in the absence or presence of the test compound in a buffer containing 50 mM Tris-HCl (pH 7.4), 2 mM MgCl2 and 1 mM EDTA. Nonspecific binding was determined in the presence of 100 µM (−)epinephrine. Following incubation, the samples were filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters were dried then counted for radioactivity in a scintillation counter (Topcount, Packard) using a scintillation cocktail (Microscint 0, Packard). The results are expressed as a percent inhibition of the control radioligand specific binding. The standard reference compound was yohimbine, which was tested in each experiment at several concentrations to obtain a competition curve from which its IC50 was calculated.

Table 5: Percent Inhibition from Radioligand Binding Assays Using Cells Expressing Human Transporters and Receptors Each compound was tested in a single concentration at 1.0 E-5 M and in duplicate. Reported values are mean values.

Table 5 shows test data from different radioligand binding assays for some of the compounds of the invention as well as for a structurally related compound in the prior art named in Table 5 as Reference Compound. Said compound is described in WO 2004/113297 where it is stated to be useful as a monoamine neurotransmitter re-uptake inhibitor. The IUPAC name of the Reference Compound is 3-(3,4-dichlorophenoxy)azetidine hydrochloric acid salt and its structure is shown below.

| Example | SERT (h) (% inhibition) | NET (h) (% inhibition) | DAT (h) (% inhibition) |
|---|---|---|---|
| 1A | 59% | 37% | 49% |
| 2 | 12% | 25% | 12% |
| 3 | 11% | 25% | 10% |
| 10 | 29% | −2% | 15% |
| 20 | 6% | 10% | 25% |
| 38 | −11% | 6% | 11% |
| 39 | 1.5% | 11% | 17% |
| 43 | −7.6% | −1% | 11% |
| 49 | 10% | 6% | 12% |
| 50 | 28% | 3% | 17% |
| 51 | 25% | 5% | 10% |
| 52C | 29% | 25% | 25% |
| Reference Compound* | 92% | 84% | 79% |

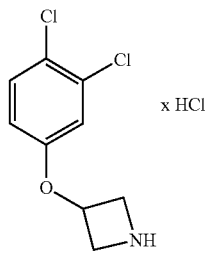 [SMILES: Clc1ccc(OC2CNC2)cc1Cl]

As can be seen from Table 5, the binding affinities of the compounds of the invention at each of the different monoamine transporters (SERT, NET, DAT) are much lower than about 75% whereas the Reference Compound binds with an affinity higher than about 75% at all the three monoamine transporters (SERT, NET, DAT).

Table 6: $IC_{50}$ Values for Example 1 and the Reference Compound 3-(3,4-Dichlorophenoxy)Azetidine Hydrochloric Acid Salt Employing Radioligand Binding Assays Using Cells Expressing Human Transporters and Receptors In another binding study employing the same assays for the three monoamine transporters as described herein above, one of the compounds of the invention (Example 1A) was tested at different concentrations in order to obtain dose-response curves. Furthermore, the above mentioned Reference Compound was tested in the same assays at different concentrations and the $IC_{50}$ values of both of the compounds are presented in Table 6.

| Example | SERT (h) $IC_{50}$ | NET (h) $IC_{50}$ | DAT (h) $IC_{50}$ |
|---|---|---|---|
| 1A | 34 µM | 79 µM | 21 µM |
| Reference Compound* | 1.3 µM | 2.2 µM | 3.5 µM |

*Reference Compound: 3-(3,4-dichlorophenoxy)azetidine hydrochloric acid.

As can be seen from Table 6, the Reference Compound is 26, 36 and 6-fold more potent than Example 1A at SERT, NET and DAT, respectively.

In Vitro Binding Studies Employing the Human Alpha 2A Adrenergic Receptor and/or the Non-Selective Adrenergic Alpha 2 Receptor In vitro binding studies employing the human alpha 2A adrenergic receptor and/or the non-selective adrenergic alpha 2 receptor surprisingly showed that the compounds according to Example 1A, Example 3, Example 20 and Example 52C inhibited the binding of a radioactively labeled ligand to more than 93% at a concentration of 10 µM.

REFERENCES

1. Hamon et al. (Prog Neuro-Psychopharm & Bio Psych, 2013, 45, 54-63)
2. Arnsten (Biol Psych, 2011, 69(12); 89-99)
3. Wang (Front Cell Neurosci, 2015, 9; 1-23)
4. Trillo et al. (Neurosci & Biobehav Rev, 2013, 37; 1363-79)
5. Harrison et al., Mol Psych, 2005, 10; 40-68
6. Abi-Dargham et al., Eur Psych, 2005, 20; 15-27
7. WO 2004/113297
8. EP 2754653
9. WO 2010/022055
10. WO 2011/103196
11. WO 2007148185
12. WO 2010084438
13. Claffey et al. J Med Chem, 2012, 55, 9055-9068
14. WO 2010/058018
15. WO 2016/185032
16. WO 2106/073420
17. WO 2010/058017
18. WO 2016/030310
19. Devoto et al, Molecular Psychiatry (2001), 6(6), 657-664
20. Rautio et al., Nat Rev Drug Discov, 2008, 7(3); 255-70
21. Paulekuhn G S et al., J Med Chem, 2007, 50; 6665-72
22. Berge S M et al., J Pharm Sci, 1977, 66; 1-19
23. Ungerstedt, J Int Med, 1991, 230; 365-73
24. Sesack et al. (Anatom Substr Glut-Dopamine Inter. Annals of NY AcadSci, 2003, 1003; 36-52
25. Link W et al., Proc Natl Acad Sci, USA, 1995, 92; 5734-8
26. Lyford G L et al., Neuron, 1995, 14; 433-45
27. Steward and Worley, Neuron, 2001, 30; 227-40
28. Kawashima et al., PNAS, 2009, 106(1); 316-21
29. Bramham et al., Exp Brain Res, 2010, 200; 125-40)
30. Perrin et al., J. Am. Chem. Soc. 2007, 129, 4490-4497
31. WO 2012/168817
32. WO 2017/045648
33. Crespi CL and Stresser D M, J Pharm Tox Meth, 2000, 44; 325-31
34. Renwick A B et al., Xenobiotica, 2001, 31(4); 187-204
35. Waters et al., J Neural Transm Gen Sect, 1994, 98(1); 39-55
36. Santiago and Westerink, N-S Arch Pharmacol, 1990, 342; 407-14
37. Paxinos and Watson (New York, Academic Press, 1986; FIG. 8 and FIG. 14)
38. Moghaddam and Bunney. Neurochem., 1989, 53; 652-4
39. Chomczynski P and Sacchi N, Anal Biochem, 1987, 162(1); 156-9
40. Landgren et al, J. Neural Transm. 2012, 119; 833-842
41. Tatsumi, M., Jansen, K., Blakely, R. D. and Richelson, E., Eur. J. Pharmacol. 1999, 368: 277.)
42. Pacholczyk, T., Blakely, R. D. and Amara, S. G. Nature, 1991, 350: 350
43. Pristuba, Z. B., Wilson, J. M., Hoffman, B. J., Kish, S. J. and Nisnik, H. B. Mol. Pharmacol., 1994, 45: 125
44. Langin, D., Lafontan, M., Stilling, M. R. and Paris, H. Eur. J. Pharmacol. 1989, 167: 95

The invention claimed is:

1. A pharmaceutical composition comprising a compound of Formula I:

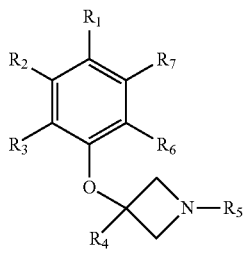

Formula I or an isotope labelled analog thereof, or a pharmaceutically acceptable salt thereof,
wherein:
each of $R_1$, $R_2$, $R_3$, $R_6$ and $R_7$ represents H or F,
$R_4$ represents H or $CH_3$
$R_5$ represents H or $C_1$-$C_4$alkyl,
wherein at least two of $R_1$, $R_2$, $R_3$, $R_6$ and $R_7$ represent F, together with at least one pharmaceutically acceptable carrier, excipient and/or diluent,
wherein the compound of Formula I is not:
3-(2,3-difluorophenoxy)azetidine in non-salt form, or
3-(2,3,4-trifluorophenoxy)azetidine in non-salt form, or
3-(2,3,4,5,6-pentafluorophenoxy)azetidine in non-salt form, or
3-(2,4-difluorophenoxy)azetidine in non-salt form, or
3-(2,4-difluorophenoxy)azetidine hydrochloric acid salt, or
3-(2,5-difluorophenoxy)azetidine in non-salt form, or
3-(2,6-difluorophenoxy)azetidine in non-salt form, or
3-(2,6-difluorophenoxy)azetidine hydrochloric acid salt, or
3-(3,4-difluorophenoxy)azetidine in non-salt form, or
3-(3,4-difluorophenoxy)azetidine hydrochloric acid salt, or
3-(3,5-difluorophenoxy)azetidine in non-salt form, or
3-(3,5-difluorophenoxy)azetidine hydrochloric acid salt, or
3-(2,4,6-trifluorophenoxy)azetidine in non-salt form, or
3-(2,4,5-trifluorophenoxy)azetidine in non-salt form.

2. The pharmaceutical composition according to claim 1, wherein:
at least one of $R_1$, $R_2$, $R_3$, and $R_7$ represents F, and
$R_6$ represents F.

3. The pharmaceutical composition according to claim 1, wherein:
at least one of $R_1$, $R_2$, $R_3$, and $R_6$ represents F, and
$R_7$ represents F.

4. The pharmaceutical composition according to claim 1, wherein:
$R_4$ is H.

5. The pharmaceutical composition according to claim 1, wherein:
$R_4$ is $CH_3$.

6. The pharmaceutical composition according to claim 1, wherein:
$R_5$ is H.

7. The pharmaceutical composition according to claim 1, wherein:
$R_5$ is $C_1$-$C_4$ alkyl.

8. The pharmaceutical composition according to claim 1, wherein the compound of Formula I is a pharmaceutically acceptable salt of 3-(2,3-difluorophenoxy)azetidine.

9. A compound of Formula I:

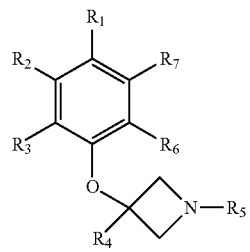

Formula I or an isotope labelled analog thereof, or a pharmaceutically acceptable salt thereof,
wherein:
each of $R_1$, $R_2$, $R_3$, $R_6$ and $R_7$ represents H or F,
$R_4$ represents H or $CH_3$
$R_5$ represents H or C1-C4alkyl,
wherein at least two of $R_1$, $R_2$, $R_3$, $R_6$ and $R_7$ represent F, with the proviso that the compound of Formula I is not:
3-(2,3-difluorophenoxy)azetidine in non-salt form, or
3-(2,3,4-trifluorophenoxy)azetidine in non-salt form, or
3-(2,3,4,5,6-pentafluorophenoxy)azetidine in non-salt form, or
3-(2,4-difluorophenoxy)azetidine in non-salt form, or
3-(2,4-difluorophenoxy)azetidine hydrochloric acid salt, or
3-(2,5-difluorophenoxy)azetidine in non-salt form, or
3-(2,6-difluorophenoxy)azetidine in non-salt form, or
3-(2,6-difluorophenoxy)azetidine hydrochloric acid salt, or
3-(3,4-difluorophenoxy)azetidine in non-salt form, or
3-(3,4-difluorophenoxy)azetidine hydrochloric acid salt, or
3-(3,5-difluorophenoxy)azetidine in non-salt form, or
3-(3,5-difluorophenoxy)azetidine hydrochloric acid salt, or
3-(2,4,6-trifluorophenoxy)azetidine in non-salt form, or
3-(2,4,5-trifluorophenoxy)azetidine in non-salt form.

10. The compound of Formula I according to claim 9 which is an isotope labelled analog of 3 (2,3-difluorophenoxy)azetidine.

11. The compound of Formula I according to claim 9 which is an isotope labelled analog of or a pharmaceutically acceptable salt of 3-(3,5-difluorophenoxy)azetidine
with the proviso that the compound of Formula I is not 3-(3,5-difluorophenoxy)azetidine hydrochloric acid salt.

12. The compound of Formula I according to claim 9 which is 3-(2,3,5,6-tetrafluorophenoxy)-azetidine, or an isotope labelled analog thereof, or a pharmaceutically acceptable salt thereof.

13. The pharmaceutical composition according to claim 1, wherein the compound of Formula I is an isotope labelled analog of 3-(2,3-difluorophenoxy)azetidine.

14. The pharmaceutical composition according to claim 1, wherein the compound of Formula I is 3-(2,3,5,6-tetrafluorophenoxy)azetidine, or an isotope labelled analog thereof, or a pharmaceutically acceptable salt thereof.

15. The pharmaceutical composition according to claim 1, wherein the compound of Formula I is an isotope labelled analog or a pharmaceutically acceptable salt of 3-(2,3,5,6-tetrafluorophenoxy)azetidine.

16. The pharmaceutical composition according to claim 1, wherein the compound of Formula I is an isotope labelled analog of or a pharmaceutically acceptable salt of 3-(3,5-difluorophenoxy)azetidine with the proviso that the compound of Formula I is not 3-(3,5-difluorophenoxy)azetidine hydrochloric acid salt.

17. The pharmaceutical composition according to claim 1, wherein the compound of Formula I is an isotope labelled analog of 3-(3,5-difluorophenoxy)azetidine.

18. The compound of Formula I according to claim 9 which is a pharmaceutically acceptable salt of 3-(2,3-difluorophenoxy)azetidine.

19. The compound of Formula I according to claim 9 which is a pharmaceutically acceptable salt of an isotope labelled analog of 3-(2,3-difluorophenoxy)azetidine.

20. The pharmaceutical composition according to claim 1, wherein the compound of Formula I is a pharmaceutically acceptable salt of an isotope labelled analog of 3-(2,3-difluorophenoxy)azetidine.

* * * * *